United States Patent
Rothstein et al.

(10) Patent No.: US 11,395,697 B2
(45) Date of Patent: Jul. 26, 2022

(54) DEVICES AND METHODS FOR PREPARING A VALVE FOR A TRANSCATHETER VALVE REPLACEMENT PROCEDURE

(71) Applicant: Medtronic, Inc., Minneapolis, MN (US)

(72) Inventors: Paul T. Rothstein, Elk River, MN (US); Jeffrey D. Sandstrom, Scandia, MN (US); Joel Racchini, Minneapolis, MN (US); James R. Keogh, Maplewood, MN (US); Martin T. Rothman, Bodega Bay, CA (US)

(73) Assignee: Medtronic, Inc., Minneapolis, MN (US)

( * ) Notice: Subject to any disclaimer, the term of this patent is extended or adjusted under 35 U.S.C. 154(b) by 47 days.

(21) Appl. No.: 16/682,110

(22) Filed: Nov. 13, 2019

(65) Prior Publication Data

US 2020/0146690 A1    May 14, 2020

Related U.S. Application Data

(60) Provisional application No. 62/829,234, filed on Apr. 4, 2019, provisional application No. 62/767,025, filed
(Continued)

(51) Int. Cl.
*A61B 17/12* (2006.01)
*A61B 18/14* (2006.01)
(Continued)

(52) U.S. Cl.
CPC .... *A61B 18/1492* (2013.01); *A61B 17/00234* (2013.01); *A61B 17/12122* (2013.01);
(Continued)

(58) Field of Classification Search
CPC ........ A61B 17/12136; A61B 17/00234; A61B 17/12122; A61B 2017/00243;
(Continued)

(56) References Cited

U.S. PATENT DOCUMENTS

| 4,655,216 A | 4/1987 | Tischer |
| 5,342,357 A | 8/1994 | Nardella |

(Continued)

FOREIGN PATENT DOCUMENTS

| EP | 2110151 | 10/2009 |
| WO | 2009121017 A1 | 10/2009 |

(Continued)

OTHER PUBLICATIONS

PCT Search Report and Written Opinion for PCT/US2014/050338, dated Oct. 23, 2014, 11 pages.
(Continued)

*Primary Examiner* — Vi X Nguyen
(74) *Attorney, Agent, or Firm* — Dicke, Billig & Czaja, PLLC

(57) ABSTRACT

The disclosure relates to methods, systems and devices for severing and optionally removing at least a portion of heart valve leaflets. Leaflets can be partially removed or entirely removed or otherwise, the leaflets can be severed or splayed in such a way as to avoid coronary blockage, LVOT obstruction, or access challenges in procedures where a prosthetic valve is to be implanted within a previously implanted prosthetic valve. The disclosure also relates to numerous devices for and methods of disabling one or more valve ligating devices to provide an unobstructed valve opening so that a prosthetic heart valve can be implanted within the opening. The ligation device(s) is disabled either by removing the ligation device(s) or severing one leaflet so that ligated leaflets can be separated. In some embodiments, the ligation device(s) are severed to disable the ligation device(s).

19 Claims, 54 Drawing Sheets

Related U.S. Application Data on Nov. 14, 2018, provisional application No. 62/767,026, filed on Nov. 14, 2018.

(51) Int. Cl.
    *A61B 17/00*      (2006.01)
    *A61B 17/32*      (2006.01)
    *A61B 18/00*      (2006.01)

(52) U.S. Cl.
CPC ........ *A61B 17/32* (2013.01); *A61B 17/12136* (2013.01); *A61B 2017/00243* (2013.01); *A61B 2017/00292* (2013.01); *A61B 2018/0022* (2013.01); *A61B 2018/00369* (2013.01)

(58) Field of Classification Search
CPC .. A61B 2017/00292; A61B 2018/0022; A61B 2018/00267; A61B 2018/00273; A61B 2018/00285; A61B 2018/00369; A61B 2018/1455; A61B 18/1492; A61B 18/1445; A61B 2018/1412; A61B 2018/1415; A61B 2018/1417; A61B 2018/1497; A61B 17/12; A61B 17/12022; A61B 17/1205; A61B 17/12109; A61B 17/00; A61F 2/2418; A61F 2/2427; A61F 2/2412; A61F 2/2466; A61F 2/2436
See application file for complete search history.

(56) References Cited

U.S. PATENT DOCUMENTS

| | | | |
|---|---|---|---|
| 5,383,874 A | 1/1995 | Jackson et al. | |
| 5,437,664 A | 8/1995 | Cohn et al. | |
| 5,496,311 A | 3/1996 | Abele et al. | |
| 5,599,350 A | 2/1997 | Schulze et al. | |
| 5,601,580 A | 2/1997 | Goldberg et al. | |
| 5,807,395 A | 9/1998 | Mulier et al. | |
| 5,984,939 A | 11/1999 | Yoon | |
| 6,009,877 A | 1/2000 | Edwards | |
| 6,027,501 A | 2/2000 | Goble et al. | |
| 6,033,398 A | 3/2000 | Farley et al. | |
| 6,036,689 A | 3/2000 | Tu et al. | |
| 6,047,700 A | 4/2000 | Eggers et al. | |
| 6,117,101 A | 9/2000 | Diederich et al. | |
| 6,254,598 B1 | 7/2001 | Edwards et al. | |
| 6,258,087 B1 | 7/2001 | Edwards et al. | |
| 6,292,701 B1 | 9/2001 | Prass et al. | |
| 6,514,250 B1 | 2/2003 | Jahns et al. | |
| 6,758,830 B1* | 7/2004 | Schaer ............... A61B 18/1492 604/528 |
| 6,764,494 B2 | 7/2004 | Menz et al. | |
| 6,830,584 B1 | 12/2004 | Seguin | |
| 6,939,359 B2 | 9/2005 | Tu et al. | |
| 7,255,706 B2 | 8/2007 | Rosengart | |
| 7,377,916 B2 | 5/2008 | Rudko et al. | |
| 8,083,736 B2 | 12/2011 | McClurken et al. | |
| 8,337,492 B2 | 12/2012 | Kunis et al. | |
| 8,808,237 B2 | 8/2014 | Thielen et al. | |
| 2002/0087156 A1 | 7/2002 | Maguire et al. | |
| 2002/0087208 A1 | 7/2002 | Koblish et al. | |
| 2002/0115992 A1 | 8/2002 | Utley et al. | |
| 2004/0260276 A1 | 12/2004 | Rudko et al. | |
| 2005/0154386 A1 | 7/2005 | West et al. | |
| 2005/0203549 A1 | 9/2005 | Realyvasquez | |
| 2007/0078459 A1 | 4/2007 | Johnson et al. | |
| 2008/0004568 A1 | 1/2008 | Jeffrey et al. | |
| 2008/0015563 A1 | 1/2008 | Hoey et al. | |
| 2008/0125772 A1 | 5/2008 | Stone et al. | |
| 2008/0188912 A1 | 8/2008 | Stone et al. | |
| 2008/0275445 A1 | 11/2008 | Kelly et al. | |
| 2008/0294161 A1 | 11/2008 | Wolf, Jr. et al. | |
| 2009/0209955 A1 | 8/2009 | Forster et al. | |
| 2009/0234355 A1 | 9/2009 | Edwards et al. | |
| 2009/0299355 A1 | 12/2009 | Bencini et al. | |
| 2010/0100087 A1* | 4/2010 | Mazzone ............... A61B 18/02 606/21 |
| 2010/0268226 A1* | 10/2010 | Epp ........................ A61B 18/14 606/48 |
| 2011/0009818 A1* | 1/2011 | Goff .................. A61M 25/0108 604/96.01 |
| 2012/0004654 A1 | 1/2012 | Jackson et al. | |
| 2012/0029512 A1 | 2/2012 | Willard et al. | |
| 2012/0203300 A1 | 8/2012 | Utley et al. | |
| 2013/0085493 A1 | 4/2013 | Bloom et al. | |
| 2013/0150881 A1 | 6/2013 | Wang et al. | |
| 2013/0158536 A1 | 6/2013 | Bloom | |
| 2013/0165914 A1* | 6/2013 | Satake ............... A61B 18/1492 606/33 |
| 2013/0172715 A1 | 7/2013 | Just et al. | |
| 2013/0172877 A1 | 7/2013 | Subramaniam et al. | |
| 2013/0184702 A1 | 7/2013 | Neal, II et al. | |
| 2014/0046323 A1* | 2/2014 | Payne ................. A61B 18/1445 606/45 |
| 2015/0005762 A1* | 1/2015 | Belk ................... A61B 18/1492 606/41 |
| 2015/0141917 A1* | 5/2015 | Tilson ..................... A61F 2/958 604/103.07 |
| 2016/0051321 A1* | 2/2016 | Salahieh .................. A61B 8/12 600/439 |
| 2016/0367311 A1* | 12/2016 | Gerrans ................. A61B 10/02 |
| 2017/0014183 A1 | 1/2017 | Gifford, III et al. | |
| 2017/0105762 A1 | 4/2017 | Bloom et al. | |
| 2018/0008298 A1 | 1/2018 | Drochner et al. | |
| 2018/0028258 A1 | 2/2018 | Zamarripa et al. | |
| 2018/0185049 A1 | 7/2018 | Gowski | |
| 2018/0280084 A1 | 10/2018 | Hancock et al. | |
| 2019/0029790 A1 | 1/2019 | Bak-Boychuk et al. | |
| 2019/0104933 A1* | 4/2019 | Stern ..................... A61B 1/307 |

FOREIGN PATENT DOCUMENTS

| | | |
|---|---|---|
| WO | 2010118064 A1 | 10/2010 |
| WO | 2012099979 | 7/2012 |

OTHER PUBLICATIONS

PCT/US2019/061139, The International Search Report and Written Opinion, dated Jul. 7, 2020, 18pages.

Kleman, Mandi E. et al., "How to perform combined cutting balloon and high pressure balloon valvuloplasty for dogs with subaortic stenosis," Journal of Veterinary Cardiology, vol. 14, pp. 351-361 (2012).

Dvir, Danny et al., "Transcatheter Laceration of Aortic Leaflets to Prevent Coronary Obstructions During TAVR, Concepts to First-in-Human Basilica Procedures," Cardiovascular Research Foundation, tct 2017, pp. 1-51 (2017).

Raizner, Albert E. et al., "Clinical experience with a spiral balloon centering catheter for the delivery of intracoronary radiation therapy," Cardiovascular Radiation Medicine, vol. 1, Issue 3, pp. 214-219 (Jul.-Sep. 1999).

\* cited by examiner

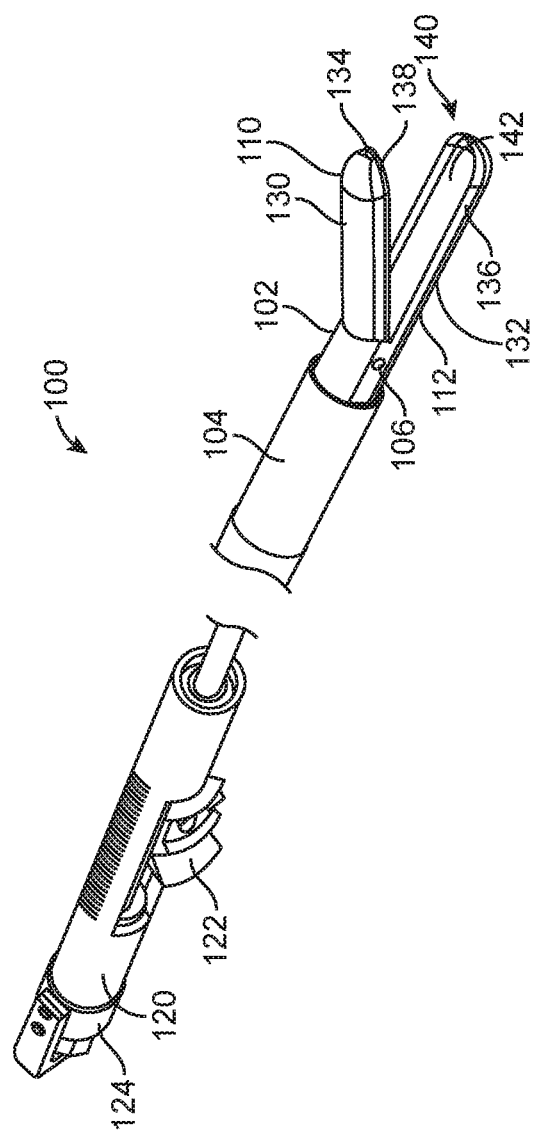

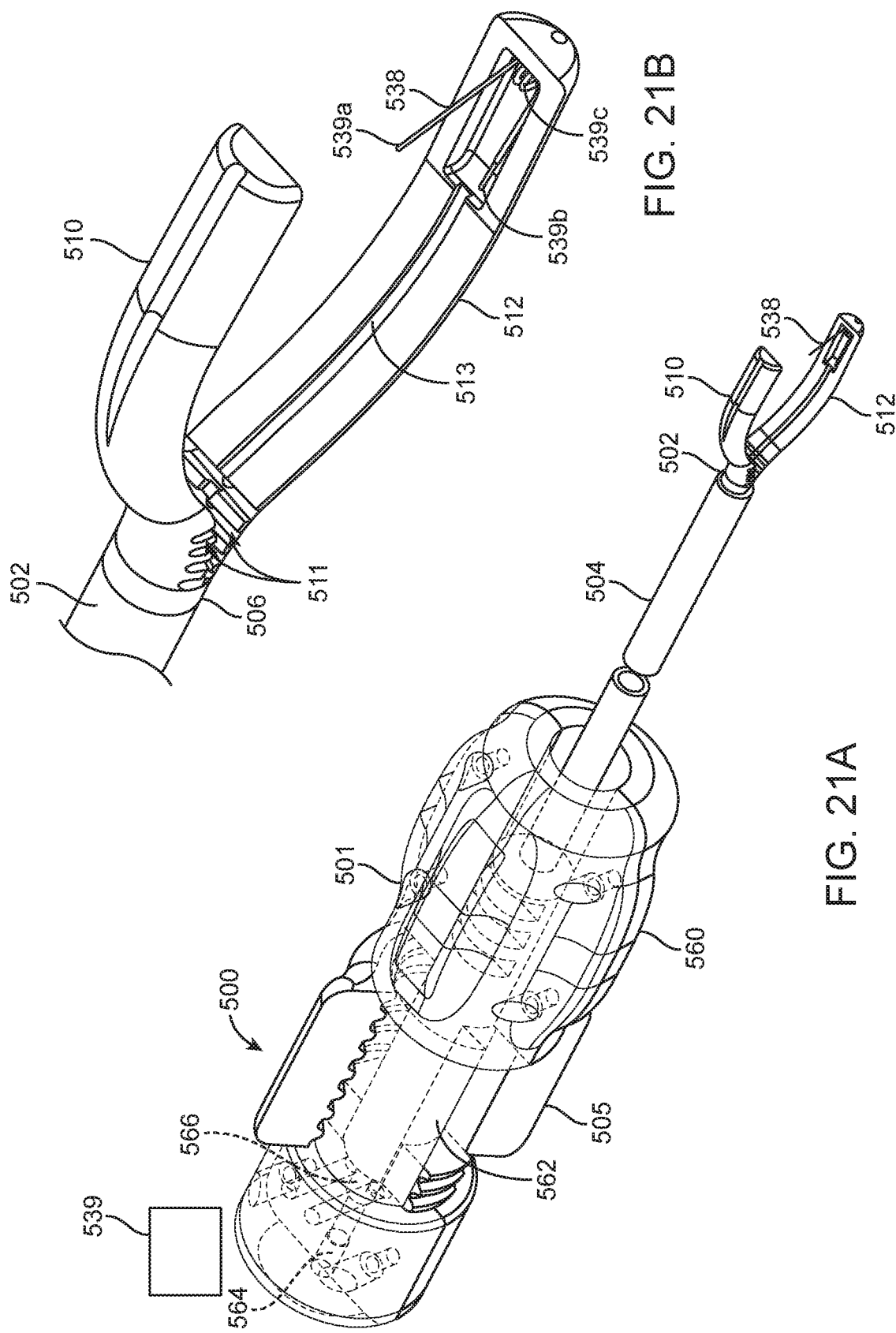

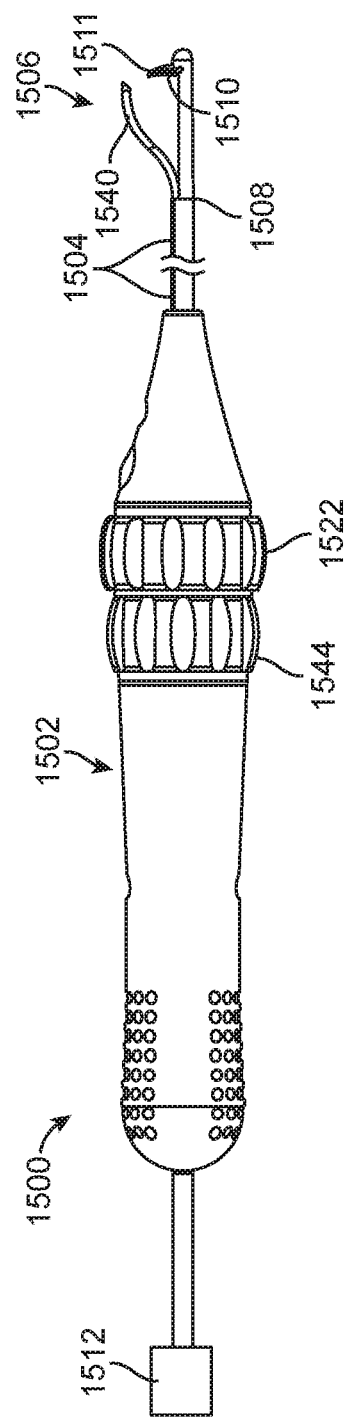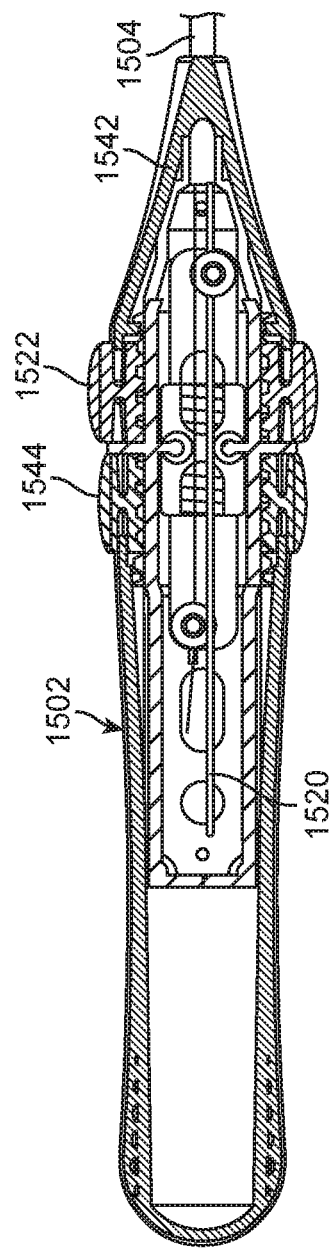

DEVICES AND METHODS FOR PREPARING A VALVE FOR A TRANSCATHETER VALVE REPLACEMENT PROCEDURE

CROSS-REFERENCE TO RELATED APPLICATION

This Non-Provisional patent application claims the benefit of the filing dates of U.S. Provisional Patent Application Ser. No. 62/829,234, filed Apr. 4, 2019; U.S. Provisional Patent Application Ser. No. 62/767,025, filed Nov. 14, 2018; and U.S. Provisional Patent Application Ser. No. 62/767,026, filed Nov. 14, 2018, the entire teachings of which are incorporated herein by reference.

FIELD

The present technology is generally related to devices for and methods for severing and optionally removing at least a portion of one or more heart valve leaflets, including the disabling and/or removal of one or more valve ligating devices, if present, so that, if desired, the valve is prepared for a subsequent procedure, such as implanting of a stented prosthetic heart valve within an opening of the treated valve.

BACKGROUND

Prior to implanting a surgical aortic valve implant, native aortic leaflets are surgically removed. In a transcatheter aortic valve (TAV) procedure, however, the native leaflets (or index valve leaflets in a prosthetic valve-in-prosthetic valve procedure) remain. The remaining leaflets are folded up into the aortic wall when a TAV is placed in position. Depending upon the particular patient anatomy (e.g., coronary height), valve placement and other factors, the displaced leaflets may become positioned against the aorta such that they block the coronary ostia and either acutely impede flow or provide challenging access to coronaries for future percutaneous coronary intervention procedures. In addition, or alternatively, the bulk of the native leaflets (or index valve leaflets in a prosthetic valve-in-prosthetic valve procedure) can reduce the Effective Orface Area (EOA) of the TAV and thus can adversely affect gradients across the valve, particularly for small annulus patients.

Clinicians have begun to address this problem by slitting the displaced leaflets so that they splay open when pinned up against the aorta, thereby allow the full opening of the native valve for replacement.

Prior to implanting a surgical mitral valve implant, native mitral leaflets are surgically removed. In a transcatheter mitral valve (TMV) procedure, however, the native leaflets (or index valve leaflets in a prosthetic valve-in-prosthetic valve procedure) remain. The remaining anterior mitral leaflet, especially if the leaflet is unusually long, can fold anteriorly into the left ventricular outflow tract (LVOT) causing obstruction with systolic anterior motion (SAM), or posteriorly under the TMV device affecting valve performance (trans-valvular flow obstruction). Various means of cutting and/or removing the leaflet or a portion thereof to manage this issue are described herein.

Various types of clips and surgical sutures (e.g. an Alfieri stitch) are utilized to provide an edge-to-edge mitral valve repair. These techniques are used to reduce the regurgitation of a diseased mitral valve by clipping the anterior and posterior leaflets together in one or more locations. Although such devices and methods are typically clinically successful in reducing regurgitation, there are cases where they do not sufficiently reduce the regurgitation or where the devices fail over time and a subsequent intervention is required. As transcatheter mitral valve replacement (TMVR) progresses and becomes approved by regulatory bodies and thus is more widely available, there will be cases where a repair patient will benefit by placement of a TMVR. However, before a TMVR is placed, the previously implanted clip or surgical repair suturing would need to be removed or disabled to allow the full opening of the native valve for replacement.

The present disclosure provides devices and methods of severing and optionally removing at least a portion of one or more heart valve leaflets in preparation of a transcatheter valve replacement procedure. In addition, the present disclosure provides devices and methods of disabling and/or removing valve ligating devices in preparation of a transcatheter valve replacement procedure. Further, the present disclosure addresses problems and limitations associated with the related art.

SUMMARY

Aspects of this disclosure generally relate to valve preparation devices, systems and methods suitable for severing and optionally removing cusp or leaflet tissue in preparation for implantation of a prosthetic heart valve. The leaflet can be severed and remain, be partially removed or be entirely removed or otherwise, the leaflet can be severed or splayed in such a way as to avoid coronary blockage, LVOT obstruction, or access challenges in procedures where a prosthetic valve is to be implanted within a native or previously implanted prosthetic valve. Such devices and methods are believed to reduce the obstruction of coronary flow or the LVOT once a prosthetic heart valve is implanted within leaflets prepared by the disclosed devices and methods.

Aspects of this disclosure also generally relate to valve preparation devices, systems and methods suitable for removing/disabling valve ligating devices and/or releasing ligated valve leaflets. In this way, a prosthetic heart valve can be implanted within an opening of the previously ligated valve (or another interventional procedure can be performed), between the released leaflets.

One aspect of the disclosure includes a valve preparation device including an outer catheter, an inner catheter coaxially slidable within the outer catheter, a balloon secured to the inner catheter and an electrode extending along a length of the balloon. In one embodiment, the device further includes a plurality of electrodes extending along a length of the balloon.

Aspects of the disclosure further include methods of preparing a heart valve having a plurality of leaflets and a valve opening. The method includes providing a valve preparation device including an outer catheter, an inner catheter coaxially slidable within the outer catheter, a balloon secured to the inner catheter and an electrode extending along a length of the balloon. The method includes delivering the valve preparation device to a first leaflet of the plurality of leaflets and aligning the electrode with an area of the first leaflet to be severed. The balloon is at least partially inflated and the electrode is actuated to create a first slit in the first leaflet.

Another aspect of the disclosure includes a valve preparation device including an inner catheter coaxially aligned and positioned at least partially within the outer catheter and a first jaw pivotally connected to a second jaw. The first and second jaws extend from the inner catheter. Each jaw defines an edge. The first and second jaws have a closed arrangement in which the edges are in contact and an open arrangement in which the first and second jaws are splayed open with respect to each other. The device further includes a first severing element connected to the second jaw.

Aspects of the disclosure further include a method of preparing a heart valve of a patient, the heart valve having a plurality of leaflets and a valve opening. The method includes providing a valve preparation device including an outer catheter, an inner catheter coaxially aligned and positioned at least partially within the outer catheter and a first jaw pivotally connected to a second jaw. The first and second jaws extending from the inner and each jaw defining an edge. The first and second jaws have a closed arrangement in which the edges are in contact and an open arrangement in which the first and second jaws are splayed open with respect to each other. The device further includes a severing element connected to the second jaw. The method further includes delivering the valve preparation device to the heart valve and then proximally retracting the outer catheter and transitioning the first and second jaws to the open arrangement. The method includes inserting one of the first and second jaws into the valve opening to position a first leaflet of the plurality of leaflets between the first and second jaws and severing at least a portion of the first leaflet with the severing element.

In one aspect, the present disclosure provides valve preparation devices and methods for grasping and severing the anterior mitral leaflet, or a portion thereof, prior to, or following, the deployment of a TMVR.

In one aspect, the present disclosure provides a valve preparation device including an outer catheter, an inner catheter coaxially aligned and positioned at least partially within the outer catheter and a first jaw pivotally connected to a second jaw. The first and second jaws extend from the inner catheter and each jaw defines an edge. The first and second jaws have a closed arrangement in which the edges are in contact and an open arrangement in which the first and second jaws are splayed open with respect to each other.

In another aspect, the disclosure provides a valve preparation device comprising a catheter, a U-hook positioned within the catheter and an electrode assembly positioned at least partially within the catheter. The electrode assembly includes a first arm and a second arm; each arm including a bend portion and an electrode positioned at the bend portion.

In another aspect, the disclosure provides a valve preparation device including a catheter having a distal end. In addition, the device includes a plurality of loops used to locate and orient the severing elements relative to the leaflets to be cut. The loops have a delivery arrangement in which the loops have a first diameter. The loops also have a deployed arrangement in which the loops have a second diameter and extend from the distal end. The device further includes a plurality of feelers, allowing multiple simultaneous cuts to be made in each leaflet. The feelers have a delivery arrangement in which the feelers are positioned proximal with respect to the distal end and a deployed arrangement in which the feelers extend distal with respect to the distal end. Each feeler is a tube in which a severing element is positioned.

In yet another aspect, the disclosure provides methods of removing a portion of at least one leaflet of a heart valve. The methods can include providing a device as disclosed herein and directing the device to the leaflet. In some embodiments, a grasper is used to direct a catheter of the device. Once the device is in position, the method includes severing the leaflet. The method can further include implanting a stented prosthetic heart valve within the treated valve.

In yet another aspect, the disclosure relates to a valve preparation device including a catheter having distal and proximal ends, the catheter further including an inflation lumen. The device further includes balloon positioned at the distal end of the catheter and in fluid communication with the inflation lumen. The balloon has one or more electrodes for cutting leaflet tissue.

In yet another aspect, the disclosure relates to a method of treating calcified leaflets. The method includes providing a valve preparation device including a catheter having distal and proximal ends, the catheter further including an inflation lumen. The device further includes balloon positioned at the distal end of the catheter and in fluid communication with the inflation lumen. The balloon has one or more electrodes for cutting leaflet tissue. The method includes delivering the balloon in a deflated arrangement to a valve, at least partially inflating the balloon and energizing the electrode to create a slit in at least one leaflet of the valve. The method can further include implanting a stented prosthetic heart valve within the treated valve.

In yet another aspect, the disclosure provides a valve preparation device including a catheter including a first lumen, second lumen, third lumen and fourth lumen. The device further includes a first positioning arm extending within the first lumen and distally out of the catheter and a second positioning arm extending within the second lumen and distally out of the catheter. The device further includes a wire extending through both of the third and fourth lumens, wherein the lumen maintains an electrode positioned distal to the catheter. The disclosure includes numerous other devices suitable for severing leaflet tissue to either release the ligating device or remove the ligating device from a body of a patient.

In yet another aspect, the disclosure provides methods of treating a patient having a ligating device, such as a clip or suture, interconnecting a pair of heart valve leaflets, for example an anterior mitral leaflet and a posterior mitral leaflet of a mitral valve. The method includes providing a device comprising a catheter from which a severing element extends and directing the severing element proximate the ligating device. The valve is severed with the severing element proximate the ligating device until the ligating device no longer obstructs the opening. In some embodiments the ligating device remains secured to one leaflet within the patient and in other embodiments, the ligating device is removed from the patient. The method can further include implanting a stented prosthetic heart valve within the opening.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1A is a partial, perspective view of a valve preparation device.

FIG. 21A is a perspective view of an alternate valve preparation device.

FIGS. 21B-21C are perspective views of the distal end of the valve preparation device of FIG. 21B.

FIG. 42 is a perspective view of an alternate device including a handle assembly and two jaws, one of which includes a severing element.

FIG. 43 is a cross-sectional view of the handle assembly of FIG. 42.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1B:
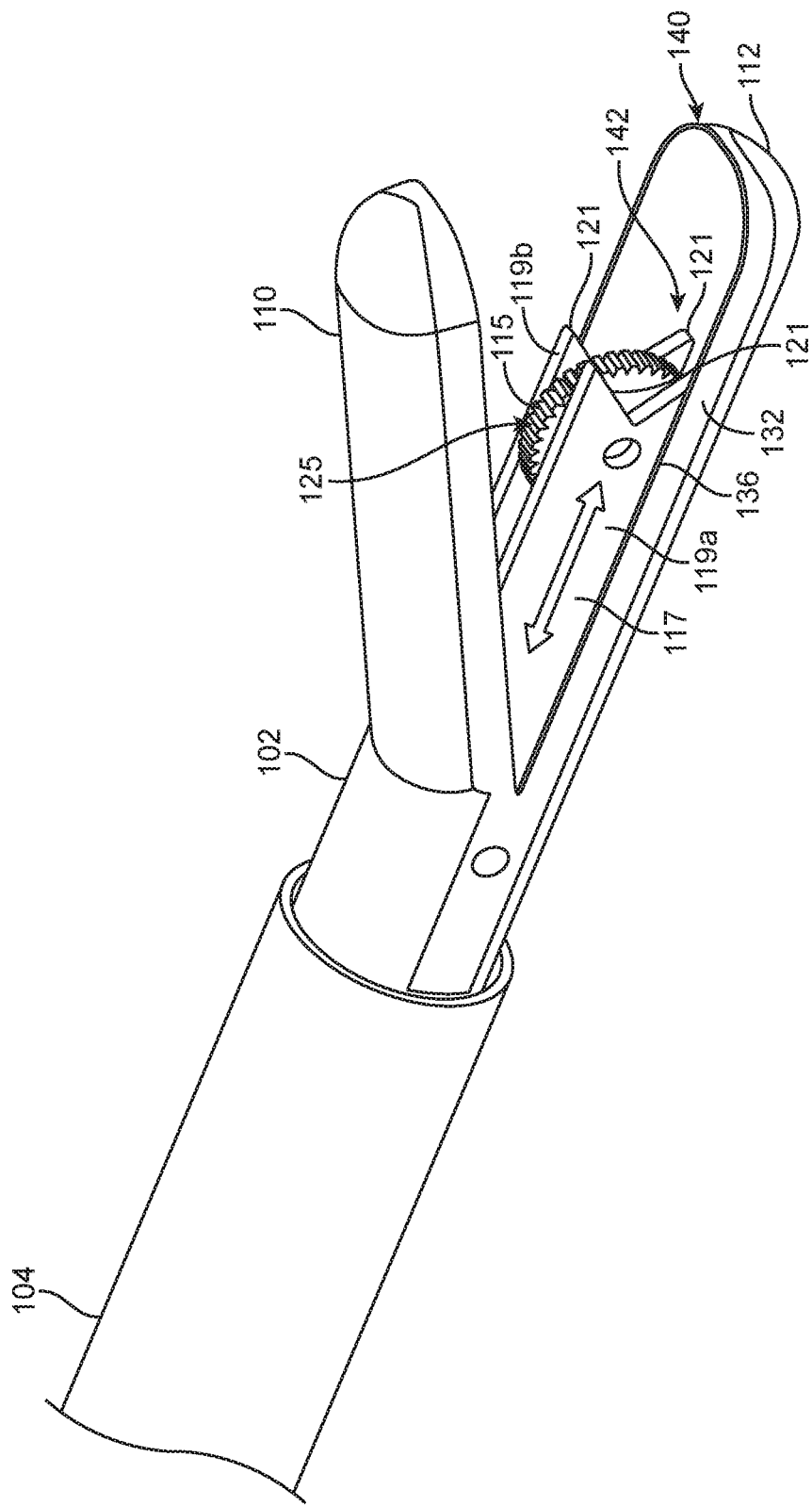
FIG. 1B is a partial, perspective view of the valve preparation device of FIG. 1A including an optional rotary cutting mechanism.
Figure 1C:
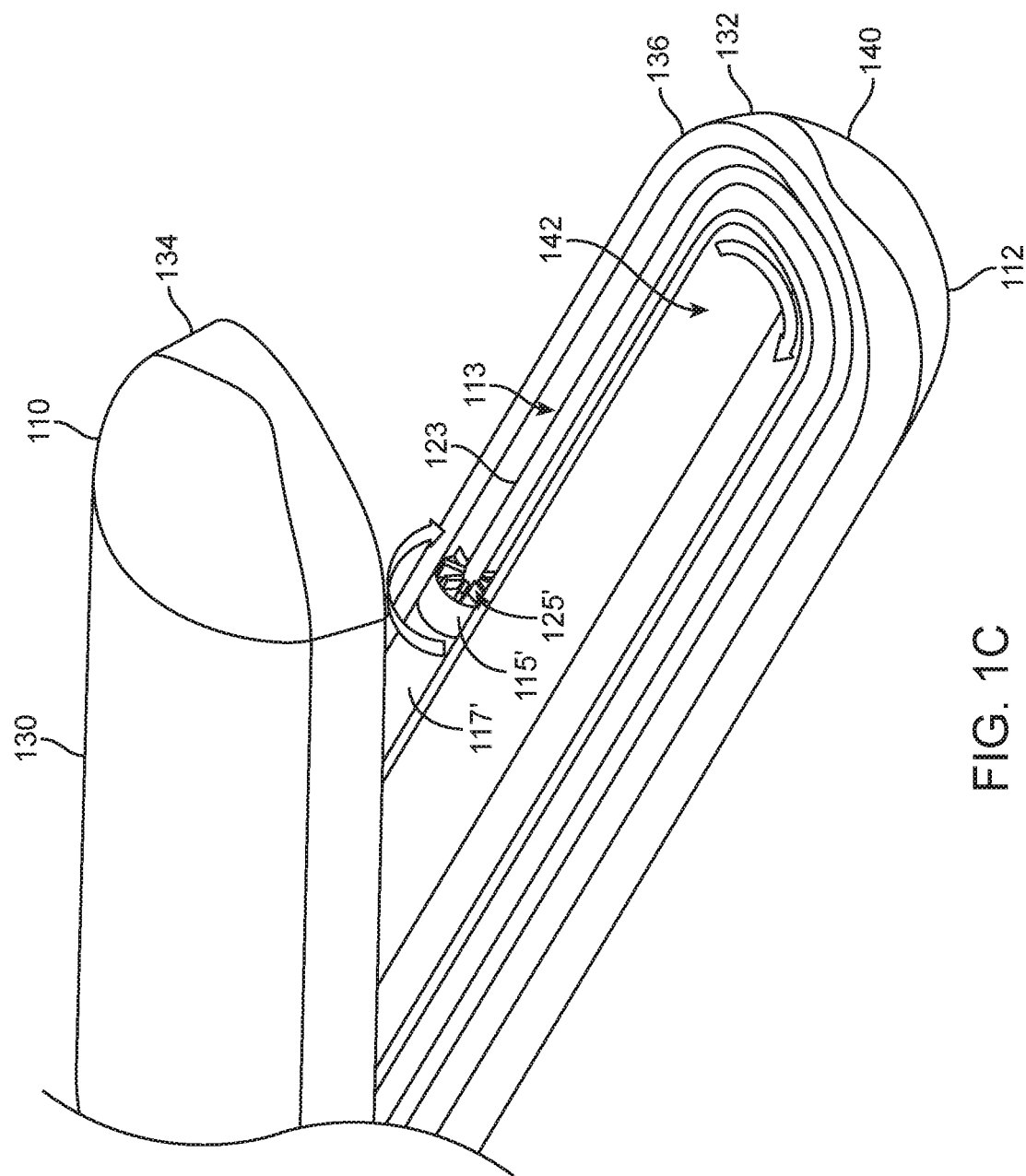
FIG. 1C is a partial, perspective view of the valve preparation device of FIG. 1A having an optional U-shaped channel for receiving a rotary cutting mechanism.
Figure 2:
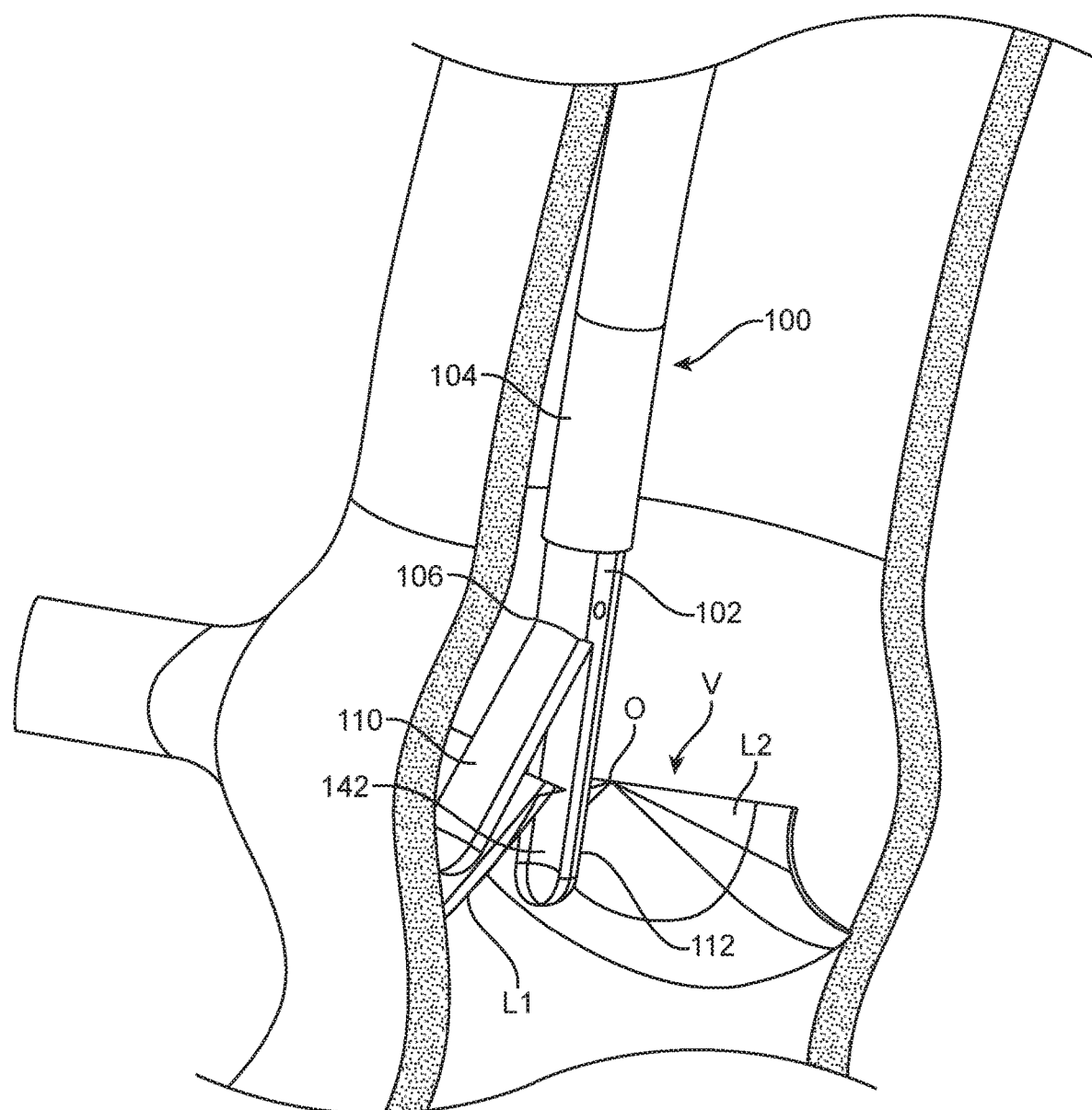
FIG. 2 is a partial, perspective view of the device of FIG. 1A delivered to an aortic valve.

One valve preparation device 100 and variations thereof are collectively illustrated in FIGS. 1A-2. The valve preparation device 100 includes an inner catheter 102 and an outer catheter 104 coaxially arranged to slide over the inner catheter 102. At a distal end 106 of the inner catheter 102, first and second jaws 110, 112 are provided. The first jaw 110 is pivotally connected to the second jaw 112 so that the jaws 110, 112 can selectively transition from an open arrangement to a closed arrangement. In the open arrangement, the first jaw 110 is pivoted away from the second jaw 112 as is shown in FIG. 1A. In the closed arrangement, the first jaw 110 is oriented generally parallel to the second jaw 112, minimizing the profile of the collective jaws 110, 112. Actuation of the first jaw 110 to the open arrangement can be accomplished in a variety of manners. For example, the first jaw 110 can be biased into the open arrangement with a spring or the like (not shown). An elongated member (e.g., suture, wire of the like, not shown) can be connected to the first jaw 110 to pull the first jaw 110 into the closed arrangement. Upon release of tension in the elongated member, the first jaw 110 transitions to the open arrangement due to the bias. The catheters 102, 104 are connected to a handle assembly 120 opposite the distal end 106. The handle assembly 120 can take a variety of forms capable for directing the catheters 102, 104 during a vascular access procedure and includes one or more actuators 122, 124 for controlling movement of the valve preparation device 100 (e.g., jaws 110/112, catheters 102/104, elongated members, or other elements of the device 100), as desired.

To assist the valve preparation or disabling device 100 in severing heart valve leaflets or cusps (referenced as L, L1, L2, AL or PL herein), each jaw 110, 112 includes a body 130, 132 defining an edge 134, 136 having a severing element 138, 140. In some embodiments, the edge 134, 136 and jaws 110, 112 collectively form a clamshell shape defining a receiving area 142 therebetween. The severing element 138, 140 can span all or a portion of the respective edge 134, 136, as desired. In various embodiments, in the closed arrangement, the severing elements 138, 140 are in contact. Each severing element 138, 140 may be an electrode, plasma electrode, high frequency ultrasound, resistive heating element, cryoablation element or microwave energy element or could be a mechanical cutter such as a blade or the like. Optionally, to reduce the profile of the device 100, the body 130, 132 of one or more jaws 110, 112 can be made of a memory-shape collapsible material (e.g., nitinol wire mesh) and the respective edge 134, 136 can be comprised of a wire (e.g., nitinol wire).

In some embodiments (partially shown in FIG. 1B and identical to FIG. 1A unless explicitly stated), mechanical energy-driven grinding of the leaflet captured within the receiving area 142 can be used as an alternative to removing larger chunks of the leaflet. For example, within the receiving area 142, a rotary cutter 115 can disposably slide distally and proximally within the receiving area 142 via actuation of a pusher 117 having first and second plates 119a, 119b supporting the rotary cutter 115. When the jaws 110, 112 are in a closed arrangement, the rotary cutter 115 is in contact with the leaflet and rotary actuation coupled with traversing by way of the pusher 117 results in grinding of the leaflet. Optionally, the plates 119a, 119b can terminate at one or V-shaped sections 121. In one example, the rotary cutter 115 can include a plurality of cutting teeth 125 (generally referenced) extending about its circumference.

Alternately, in FIG. 1C a channel 113 of the second jaw 112 forms a U-shape within the body 132, generally mirroring the path of the edge 136. Rotational and longitudinal movement of the rotary cutter 115'/pusher 117' grinds out a section of leaflet that is retained with the jaws 110, 112. In one example, the rotary cutter 115' is positioned around a track 123, which serves to guide the rotary cutter 115' around the channel 113 as the rotary cutter 115' is pushed. In this embodiment, the rotary cutter 115'/pusher 117' are directed within the channel 113. Leaflet grindings can be pulled into one catheter 102, 104 via suction applied from the inner or outer catheters 102, 104 or can be captured by a filter (not shown) mounted on the periphery of one catheter 102, 104. In some embodiments, the portion of leaflet removed can then be removed with removal of the jaws 110, 112. In one example, the rotary cutter 115' includes cutting teeth 125' (generally referenced) on its face as compared to around its circumference as in the embodiment of FIG. 1B. It will be understood that the embodiment of FIG. 1C is identically configured to that of FIG. 1A except as explicitly stated.

Use of the valve preparation device 100 of FIG. 1A, as well as any of the modified devices of FIG. 1B or 1C, can be accomplished as follows. The device 100 is delivered with the jaws 110, 112 in the closed arrangement to a heart valve V including a plurality of leaflets L1, L2, etc. via a retrograde approach. The heart valve V can be an aortic valve having three leaflets L1, L2, etc., for example, as illustrated in FIG. 2 (only two valve leaflets L1, L2 are visible for ease of illustration). The first jaw 110 is pivoted away from the second jaw 112 to the open arrangement. The second jaw 112 is then inserted through an opening O of the heart valve V, past the leaflets L1 and L2, while the first jaw 110 remains on the opposing side of the leaflet L1. In this way, the first jaw 110 and the second jaw 112 are positioned on opposing sides of the leaflet L1 so that the leaflet L1 is positioned in the receiving area 142. In various embodiments, the first and second jaws 110, 112 collectively define the receiving area 142, which is the area of leaflet L1 to be removed, as the electrodes or severing elements 138, 140 span the entire respective edges 134, 136. Therefore, the first and second jaws 110, 112 are positioned around the leaflet L1 accordingly. Once in position, the jaws 110, 112 are brought together into the closed arrangement with the handle assembly 120 or otherwise. If necessary, the severing element 138, 140 is energized or otherwise actuated to effectuate cutting/severing of the leaflet L1 at the severing element(s) 138, 140 or area at which the first and second jaws 110, 112 come into contact. In some embodiments, where applicable, the rotary cutter 115/pusher 117 (or 115', 117') are actuated to grind the leaflet L1. Then, the device 100 can be withdrawn from the patient in the closed arrangement having a severed portion of the leaflet L1 secured between the two jaws 110, 112 in the same way the device 100 was delivered. The process can be repeated until the leaflet(s) L1, L2, etc. are sufficiently removed, as desired. In some optional embodiments, a guide wire (not shown) is provided along with the device 100 to stabilize and/or capture the edge of the leaflet L1 being severed during use of the device 100.

Figure 3:
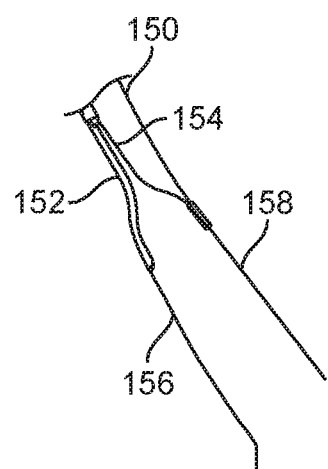
FIG. 3 is a partial, front view of a grasper that can be used to deliver various devices disclosed herein.
Figure 4:
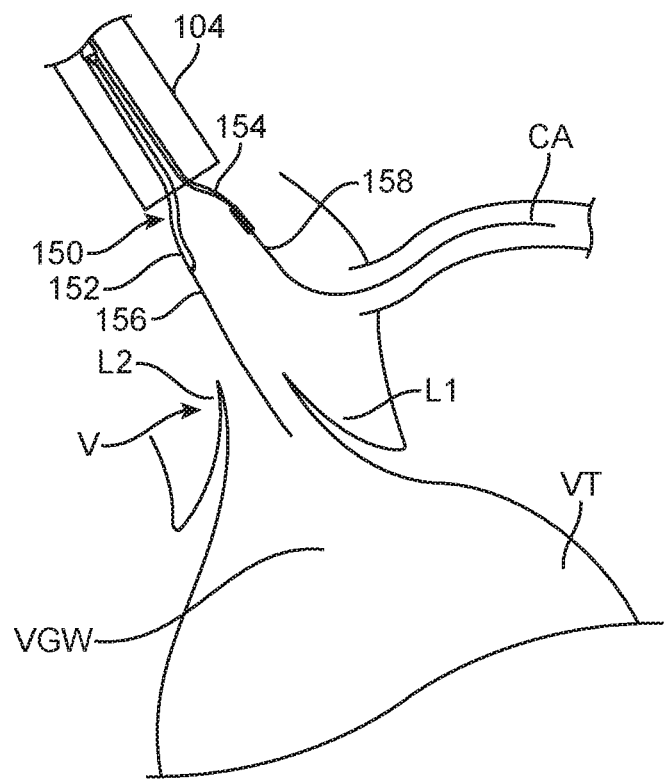
FIG. 4 is a partial, image of the grasper of FIG. 3 operatively positioned proximate a leaflet of the heart valve.
Figure 5:
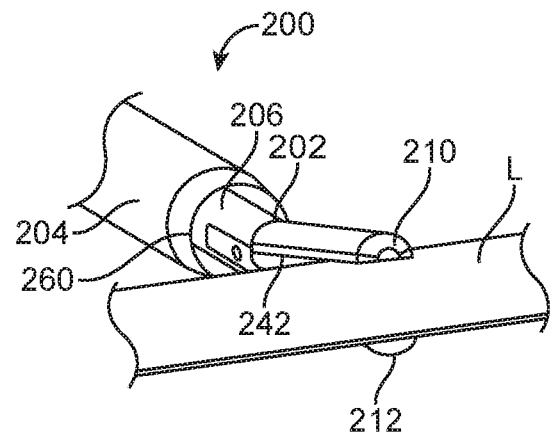
FIG. 5 is a partial, perspective view of an alternate valve preparation device in an open arrangement to engage one leaflet.

Optionally, the valve preparation device 100 can be delivered to the heart valve V with a grasper or positioning device 150 including two jaws/arms 152, 154 that are each respectively associated with a guide wire 156, 158 as is depicted in FIGS. 3-4 (the arms 152/154 otherwise function the same as jaws 110, 112 or any other jaws disclosed herein with respect to alternate embodiments). The two wires 156 and 158 operate as positioning rails on which the outer catheter 104 slides. The first arm 152 has a through lumen (not visible) from a proximal end (not shown) of the outer catheter 104 to a distal end of the first arm 152 that accepts the first guide wire 156. The second arm 154 is associated with a rapid exchange lumen (not visible) that is mounted on the second arm 154 and extends along a portion of the second arm 154 and accepts the second guide wire 158. Alternately, the second arm 154 is associated with a through lumen like the first arm 152. In one embodiment, to use the grasper 150, the first guide wire 156 is advanced across the heart valve V and lodged into a ventricle VGW. The second guide wire 158 is placed in a coronary artery CA associated with the leaflet L1 to be severed. The outer catheter 104 (shown as transparent in FIG. 4 for ease of illustration) is then advanced over the first and second guide wires 156, 158 and guides the outer catheter 104 such that the leaflet L1 is disposed between the two arms 152, 154 of the grasper 150. By actuating the grasper 150, the leaflet L1 is captured and ready for manipulation (e.g., removal and/or severing) by the device as disclosed with respect to any valve preparation and disabling device embodiment of the present disclosure. Use of the grasper 150 in the methods of the disclosure is advantageous in that use of the first and second arms 152, 154 with wires 156, 158 allows alignment of the device with the leaflet L1 and ensures grasping of the leaflet with minimal reliance on imaging technology. The positioning of the wire 158 in the coronary artery CA further assures that the associated slit or removed leaflet material is rotationally aligned with the associated coronary ostium of the associated coronary artery CA. In addition, a slight proximal tug on the outer catheter 204 by the clinician after the respective leaflet L1 is grasped with the grasper 150 can provide tactile feedback to the clinician that the leaflet L1 is, in fact, captured.

Referring now also to FIGS. 5-8, which illustrate an alternate valve preparation or disabling device 200 including an inner catheter 202 and an outer catheter 204 coaxially arranged to slide over the inner catheter 202. Similar to the prior embodiment, at a distal end 206 of the inner catheter 202, first and second jaws 210, 212 are provided defining a receiving area 242 therebetween. The first jaw 210 is pivotally connected to the second jaw 212 so that the jaws 210, 212 can selectively transition from an open arrangement (FIG. 5) to a closed arrangement (FIG. 6A). In the open arrangement, the first jaw 210 is pivoted away from the second jaw 212 so that a leaflet L can be received between the jaws 210, 212. In the closed arrangement, the first jaw 210 is oriented generally parallel to the second jaw 212. Actuation of the first jaw 210 to the open arrangement can be accomplished in a variety of manners including those described with respect to the prior embodiment of FIGS. 1A-2. Optionally, the first and/or second jaws 210, 212 can include a plurality of teeth for engaging the leaflet L and can each include a severing element (not visible) that can be similarly configured to severing elements 138, 140. The outer catheter 204 includes a severing element 260 or the like at the distal end 206. The severing element 260 can include a mechanical cutter such as a cork borer edge (as shown), electrode, or any of the severing elements disclosed with respect to prior embodiments. Distal advancement of the outer catheter 204 with respect to the inner catheter 202 can sever tissue as will be discussed in greater detail below.

In one example, use of the valve preparation or disabling device 200 can be accomplished as follows. The device 200 is delivered in the closed arrangement to the heart valve V including the plurality of leaflets L via a retrograde approach in a manner similar to that of FIG. 2. The first jaw 210 is pivoted away from the second jaw 212 to the open arrangement. The second jaw 212 is then inserted through the valve opening O, past the leaflets L, while the first jaw 210 remains on the opposing side of the leaflets L. In this way, the first jaw 210 and the second jaw 212 are positioned on opposing sides of one single leaflet L (see also, FIG. 2). The first and second jaws 210, 212 are positioned proximate a section of leaflet L to be severed or removed. Once in position, the jaws 210, 212 are brought together into the closed arrangement. If the desired amount of tissue to be removed exceeds that positioned between the first and second jaws 210, 212, the inner catheter 202, and thus the first and second jaws 210, 212, are rotated to wrap the leaflet L around an outer surface of the jaws 210, 212. In one embodiment, the inner catheter 202 is rotated about a central axis of the device 200 at least 1 degree to 360 degrees. In another embodiment, the inner catheter 202 is rotated about a central axis of the device 200 in the range of 10 degrees to 180 degrees. Once the desired amount of leaflet L to be removed is wrapped around the first and second jaws 210, 212, the outer catheter 204 is distally advanced over the inner catheter 202 and the jaws 210, 212 so that the severing element passes through the leaflet L, thus severing the leaflet L along that path. If necessary or in situations where the leaflet L is not wrapped around the jaws 210, 212, the severing element(s) 138, 140 is actuated to effectuate cutting of the leaflet L at the severing element(s) 138, 140 or joint at which the first and second jaws 210, 212 come into contact. Then, the device 200 can be withdrawn from the patient having the severed leaflet L secured around the jaws 210, 212 and/or within the receiving area 242 in the same way the device 200 was delivered. The process can be repeated until the leaflet(s) L are sufficiently removed and/or severed, as desired. In some optional embodiments, a guide wire (e.g., see other embodiments disclosed herein) is provided along with the valve preparation device 200 to stabilize and/or capture the edge of the leaflet L being severed during use of the device 200. In other embodiments, the valve preparation device 200 is provided with and used in combination with the grasper 150 as discussed above.

Figure 6A:
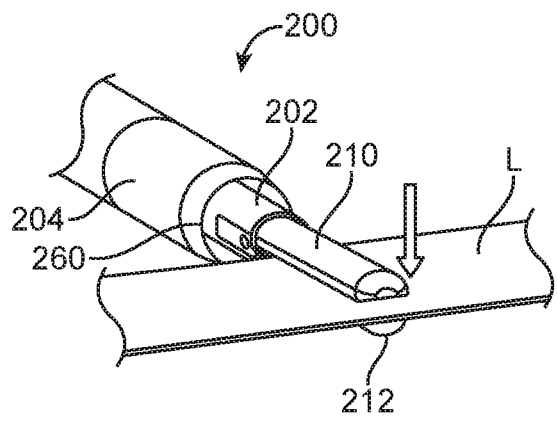
FIG. 6A is a partial, perspective view of the device of FIG. 5 in a closed arrangement, engaging the leaflet.
Figure 6B:
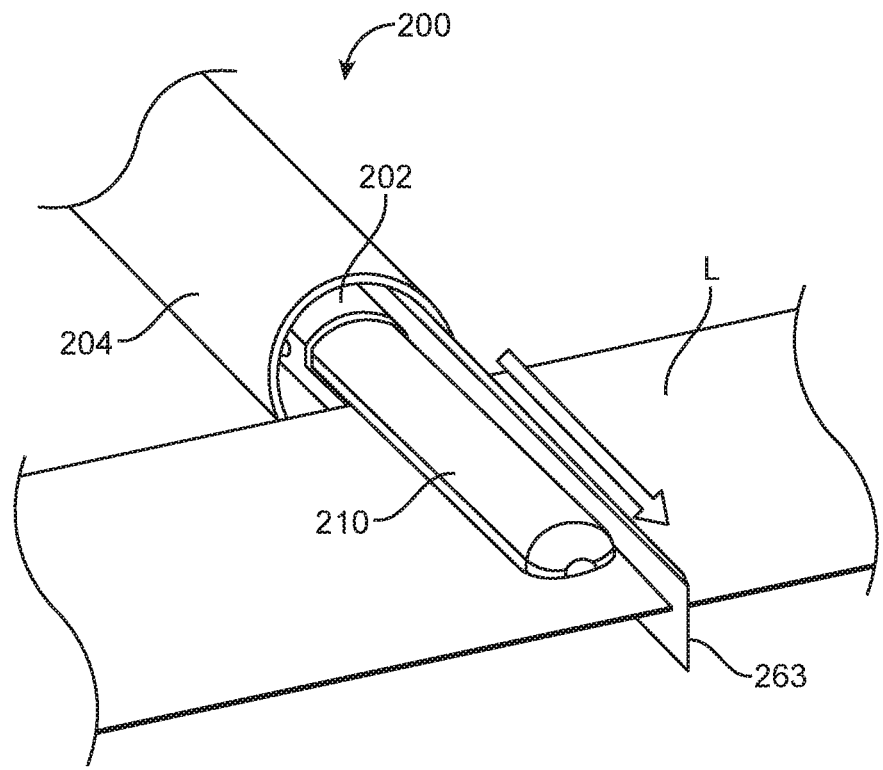
FIG. 6B is a partial, perspective view of the device of FIGS. 5-6A having an optional, slidable severing element.
Figure 8:
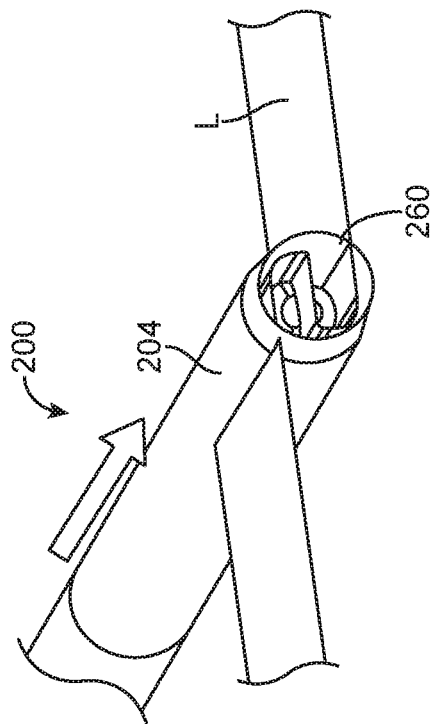
FIG. 8 is a partial, perspective view of the device of FIGS. 5-6A and 7 illustrating the outer catheter of the device in a distally advanced position in which a severing element is passed through the leaflet to cut the leaflet.
Figure 7:
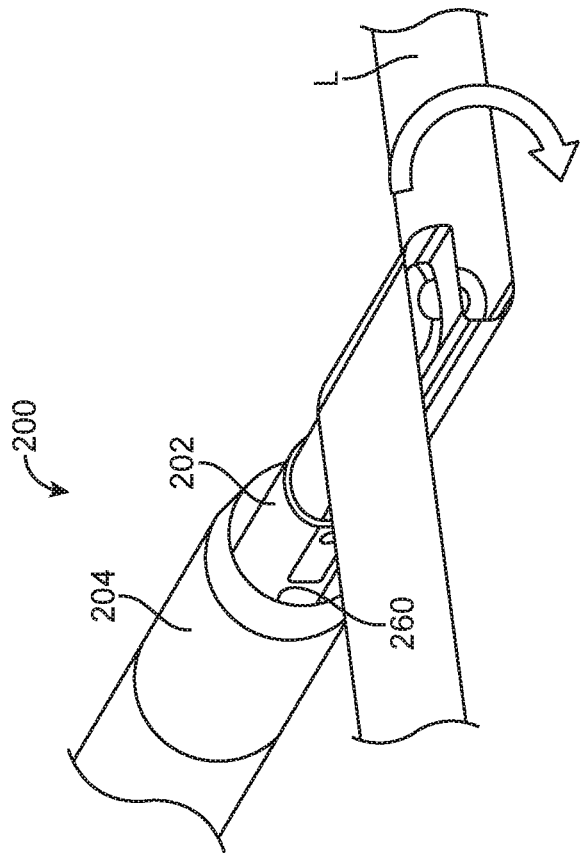
FIG. 7 is a partial, perspective view of the device of FIGS. 5-6A in a closed arrangement and rotated to wrap the leaflet about the device.
Figure 9:
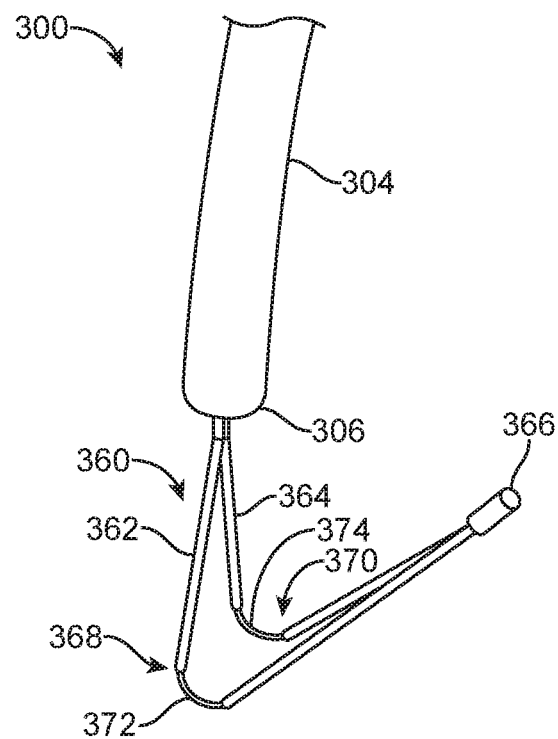
FIG. 9 is a partial, perspective view of an alternate valve preparation device including an outer catheter and electrode assembly.

In yet another embodiment, the valve preparation device 200 is provided with a second, slidable severing element 263 (FIG. 6B) configured to cut the leaflet L on one side of the jaws 210, 212 after the jaws 210, 212 initially engage the leaflet L (FIG. 6A). In this instance, the cross-section of the severing element 262 is a semi-circular or planar blade positioned on one side of the outer catheter 204 such that the tissue on only one side of leaflet L with respect to the closed jaws 210, 212 is severed. After cutting, the severing element 263 is proximally retracted to a location substantially, if not entirely, proximal to the jaws 210, 212. Rotating the device 200 about the central axis, an uncut side of the leaflet would freely roll up onto the jaws 210, 212. This method may be beneficial in situations where the leaflets L are calcified as calcified leaflets may have a low degree of elasticity and, thus, require a high degree of force to gather onto the jaws 210, 212. In addition, if high force is required to gather the leaflet L upon the jaws 210, 212 via twisting, it may be difficult to transfer this high force to the distal end of the inner catheter 202. By cutting the leaflet L before rotating the device 200, the force required should be reduced. In this method, the device 200 can be provided with the grasper 150 and is optionally used in combination with the grasper 150 as discussed above. Once the valve preparation device 200 has been rotated, the severing element 263 is advanced again to make a second cut, first ensuring rotational alignment of the severing element 263 and the uncut gathered leaflet L tissue.

Referring now also to FIGS. 9-15, which illustrate yet another valve preparation or disabling device 300. The device 300 includes an outer, delivery catheter 304 and an electrode assembly 360. The electrode assembly 360 includes first and second arms 362, 364 made of a shape memory material (e.g., a shape memory metal such as nitinol). Each arm 362, 364 terminates at and is joined at a distal end 366 that can comprise a cap 366 joining the two arms 362, 364. The arms 362, 364 are biased to the position of FIG. 9 in which the arms 362, 364 splay outwardly with respect to the delivery catheter 304 and change direction at a bend portion 368, 370. At each bend portion 368, 370, an electrode 372, 374 can be provided.

Figure 10:
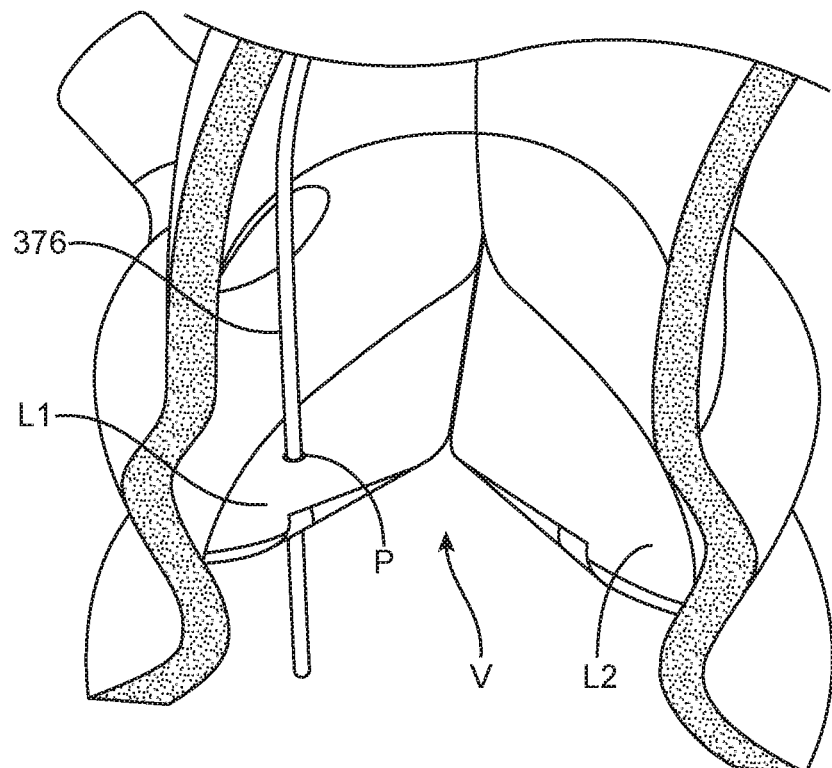
FIG. 10 is a partial, perspective view of a guide wire of the device of FIG. 9 distally advanced to puncture one leaflet.

In one embodiment, use of the valve preparation device 300 can be accomplished as follows. A guide catheter (not shown) can be delivered via a retrograde approach to the respective leaflet L1 and a guide wire 376 advanced through the guide catheter to the leaflet L1 and directed to puncture (i.e. create a hole in) the leaflet L1 with the approach as is generally depicted in FIG. 10. The guide wire 376 can be a standard guide wire or can be an electrified guide wire having an exposed electrode tip that can be introduced via the guide catheter, for example. The guide catheter can be a separate catheter or delivery catheter 304 can be disposed with a guide wire lumen and provide the same function as the described guide catheter. In an alternate embodiment, a radio frequency ("RF") tipped catheter (not shown) can be utilized to create the leaflet L1 hole or puncture P. The heart valve V can be an aortic valve, for example, as illustrated in FIGS. 10-15. In one embodiment, the guide catheter and/or electrified guide wire 376 create the puncture P in the leaflet L1 to be severed. Once the puncture P is made, several options for placement of the device 300 are possible. In one embodiment, the guide wire 376 and guide catheter are both removed and the delivery catheter 304 is advanced and brought to (or even through), the puncture P in the respective leaflet. L1 In another embodiment, the guide wire 376 is maintained in position through the leaflet L1 and the guide catheter is removed. Then, the delivery catheter 304 is delivered over the electrified guide wire to ensure the delivery catheter 304 is in position at (or even through) the leaflet puncture P. In yet another embodiment, the guide catheter is advanced to (or through the puncture P) and the guide wire 376 is removed. Then, the delivery catheter 304 is delivered through the guide catheter, which is then removed and the delivery catheter 304 is then in position. In yet another embodiment, the delivery catheter 304 provides the guide catheter function and thus eliminates the need to exchange the guide catheter with the delivery catheter 304.

Other alternative methods include forming the puncture P with the electrode assembly 360. In the first method, the delivery catheter 304 is pushed up against the leaflet L1 such that when electrode assembly 360 is distally advanced, the leading edge of the electrode assembly 360 comprises the two electrodes 372 and 374. Because they are constrained by the delivery catheter 304 when they first exit the catheter 304 at its distal end 306, they behave like a single electrode and can be energized to create the puncture P. In the second alternative, the electrode assembly 360 is loaded such that the leading edge is comprised of the end cap 366, which can be comprised of either a sharp mechanical puncture element or an electrode that can be energized to puncture the leaflet L1 to form puncture P.

Figure 11:
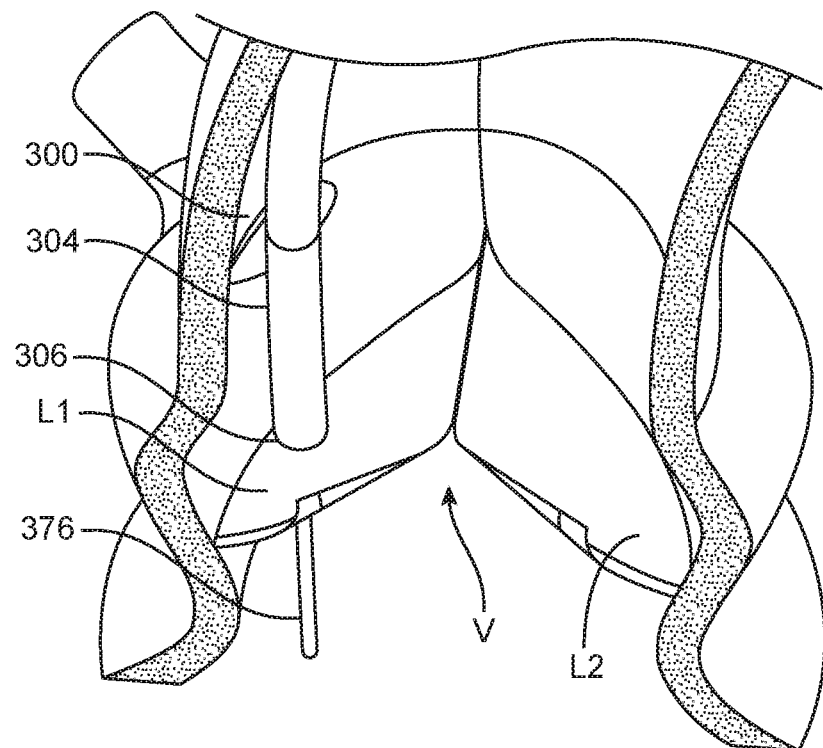
FIG. 11 is a partial, perspective view of the device of FIGS. 9-10, wherein the outer catheter is advanced over the guide wire to the leaflet.
Figure 12:
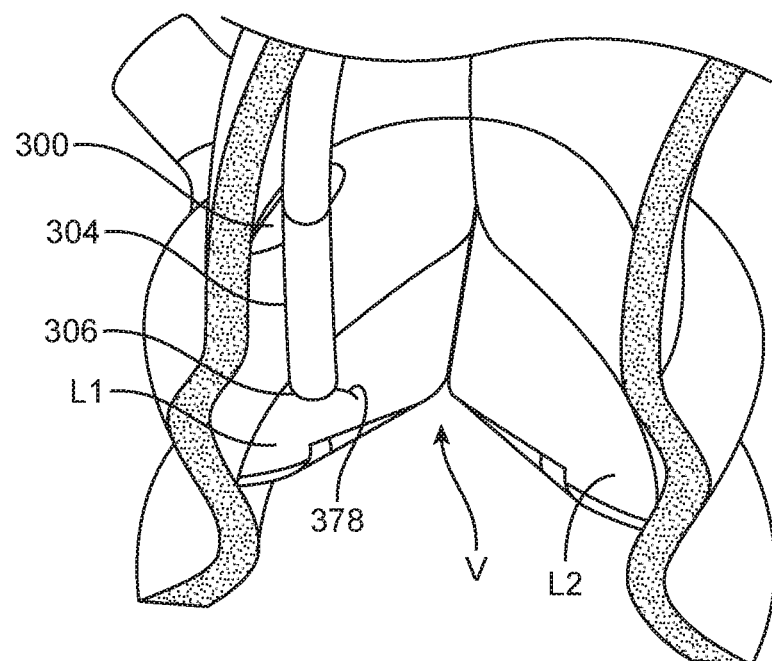
FIG. 12 is a partial, perspective view of the device of FIGS. 9-11, wherein the U-hook is distally advanced from the outer catheter to engage the leaflet.
Figure 13:
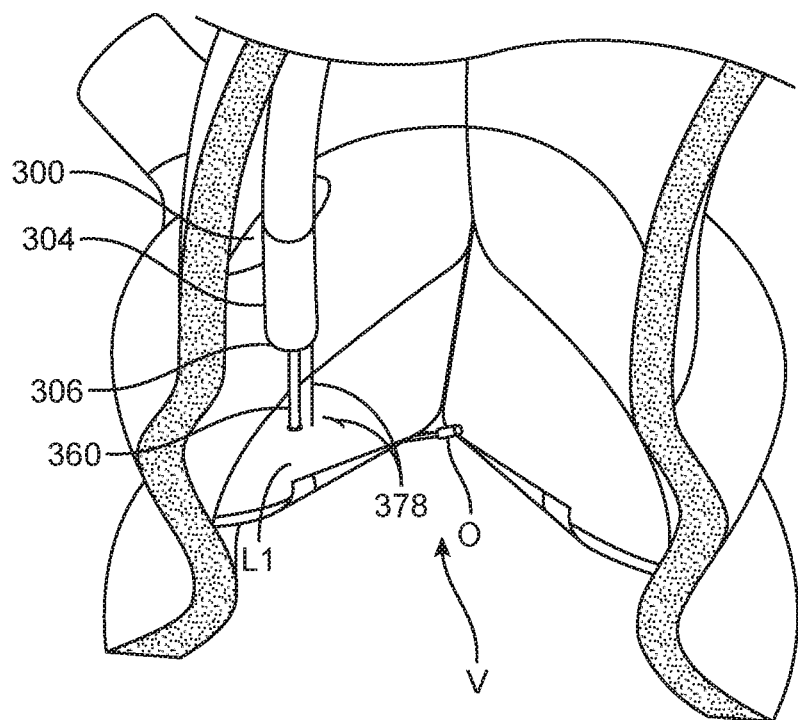
FIG. 13 is a partial, perspective view of the device of FIG. 9-12 in which the outer catheter has been proximally withdrawn to expose the electrode assembly.
Figure 14:
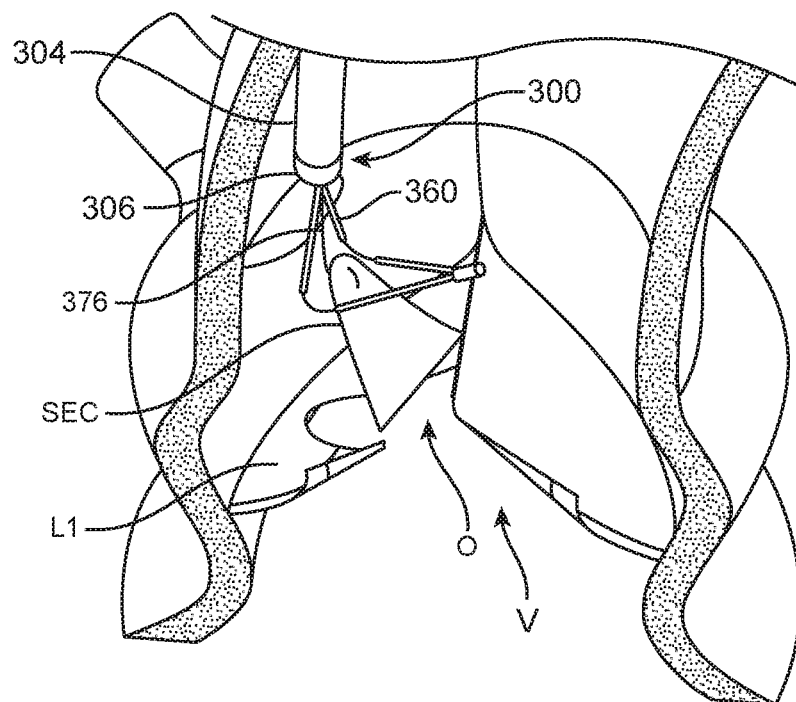
FIG. 14 is a partial, perspective view of the device of FIGS. 9-13 in which the electrode assembly has severed the leaflet tissue and the severed tissue is held by the U-hook.
Figure 15:
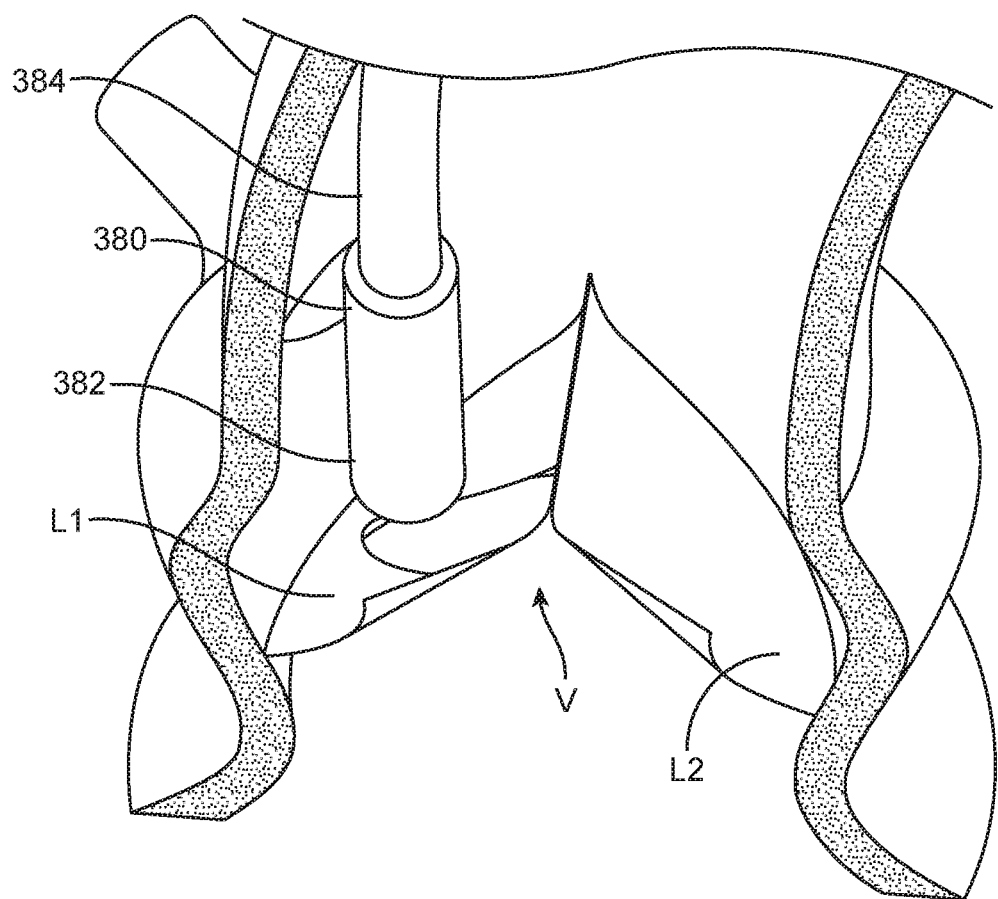
FIG. 15 is a partial, perspective view of a receiving sheath distally advanced over the device to encapsulate the device for withdrawing the device of FIGS. 9-14 from the patient.

In some embodiments, after the puncture P is formed, the delivery catheter 304 is delivered over the guide wire 376 in a delivery arrangement to the location of the puncture P so that the distal end 306 of the delivery catheter 304 is adjacent the leaflet L1 (FIG. 11). In the delivery arrangement, the electrode assembly 360 is positioned entirely within the delivery catheter 304 (i.e. the electrode assembly 360, including the electrodes 372, 374, is entirely proximal with respect to a distal end 306 of the delivery catheter 304). Once the delivery catheter 304 is in position (FIG. 11) so that the distal end 306 of the delivery catheter 304 is touching the respective leaflet L1, the guide wire 376 is removed and a U-hook 378 is advanced through the delivery catheter 304 to pierce the leaflet slit and engage a portion of the leaflet L1 to be severed/removed (FIG. 12). Alternately, the guide wire 376 can be left in place in this step (not shown in FIG. 12). In further alternate embodiments, the grasper 150 described above or some other method of securing the severed leaflet L1 can be used as a replacement to the U-hook 378. In alternate embodiments, suction, adhesive and other mechanical elements can be used to capture the severed leaflet L1. Then the delivery catheter 304 is proximally retracted to provide sufficient space for the electrode assembly 360 to exit distally out of the distal end 306 of the delivery catheter 304 as is generally shown in FIG. 13. The electrode assembly 360 is distally advanced through the delivery catheter 304 until the electrodes 372, 374 contact the leaflet L1. The electrodes 372, 374 are then energized to sever the leaflet L1 and the electrodes 372, 374 are further optionally guided along the leaflet L1 to enlarge the cuts in the direction of the valve opening O. Due to the biased nature of the arms 362, 364 the portion of leaflet L1 that encompasses section SEC (FIG. 14) is enlarged as the cuts get larger because as the electrodes 372, 374 are further deployed distally relative to the delivery catheter 304, that the shape memory material of the arms 362, 364 biases the electrodes 372, 374 further and further apart. Alternately, the electrodes 372, 374 can be advanced through the same sever encompassed by the U-hook 378 prior to enlargement of the cuts. In one embodiment, the resultant leaflet section SEC being cut away is tapered or generally triangularly shaped (FIG. 14). Once the section SEC of the leaflet L1 is cut away, the U-hook 378 is positioned between the first and second arms 362, 364 and can lift the section of the leaflet L1 proximally for removal (FIG. 14). In some embodiments, a retrieval sheath 380 is provided, which is coaxially positioned around the delivery catheter 304 (FIG. 15, however the delivery catheter 304 is not visible in FIG. 15). The retrieval sheath 380 can have a distal portion 382 having an enlarged diameter as compared to a proximal portion 384 of the delivery catheter 304. The distal portion 382 of the retrieval sheath 380 is advanced over the exposed electrode assembly 360 and U-hook 378 to compress and sheathe those elements for removal in the same manner they were delivered. The process can be repeated until the leaflet(s) L1, L2, etc. are sufficiently removed, as desired.

Figure 16:
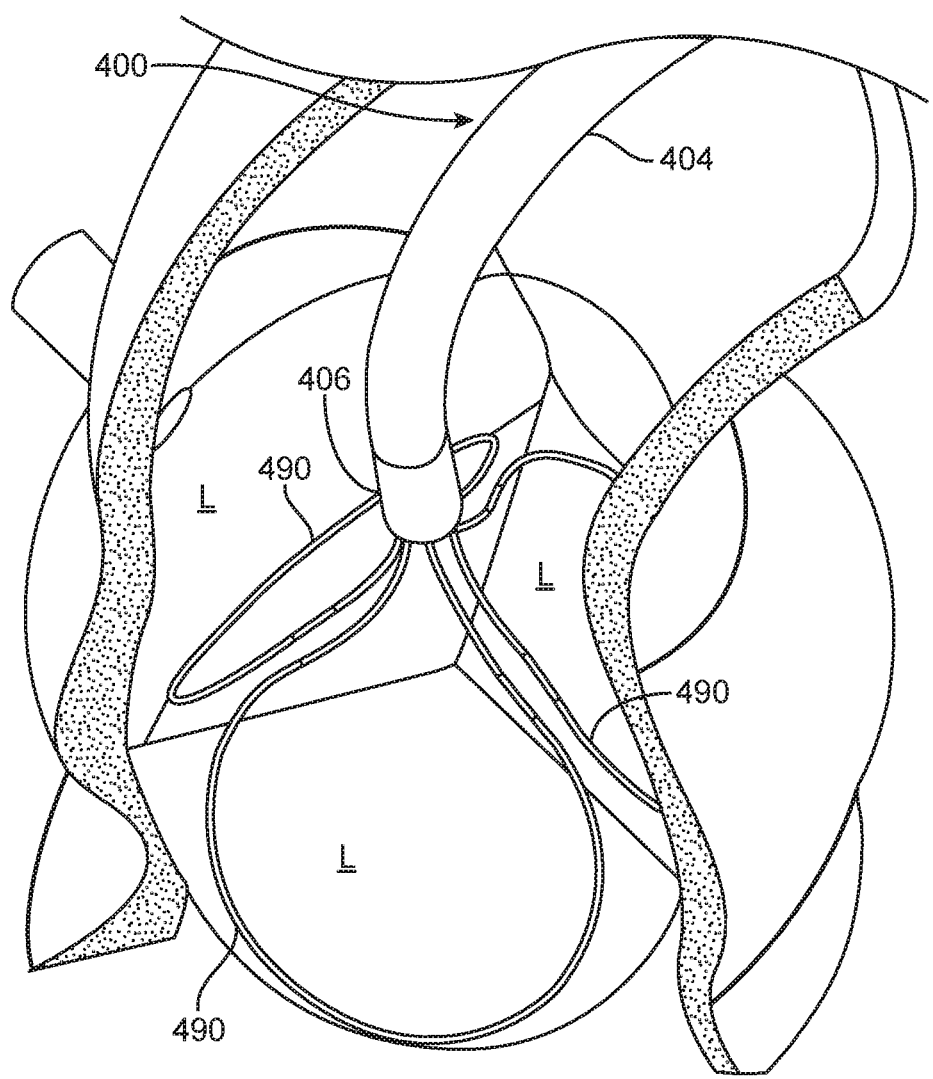
FIG. 16 is a partial, perspective view of an alternate valve preparation device including loops extending distally from an outer catheter.
Figure 17:
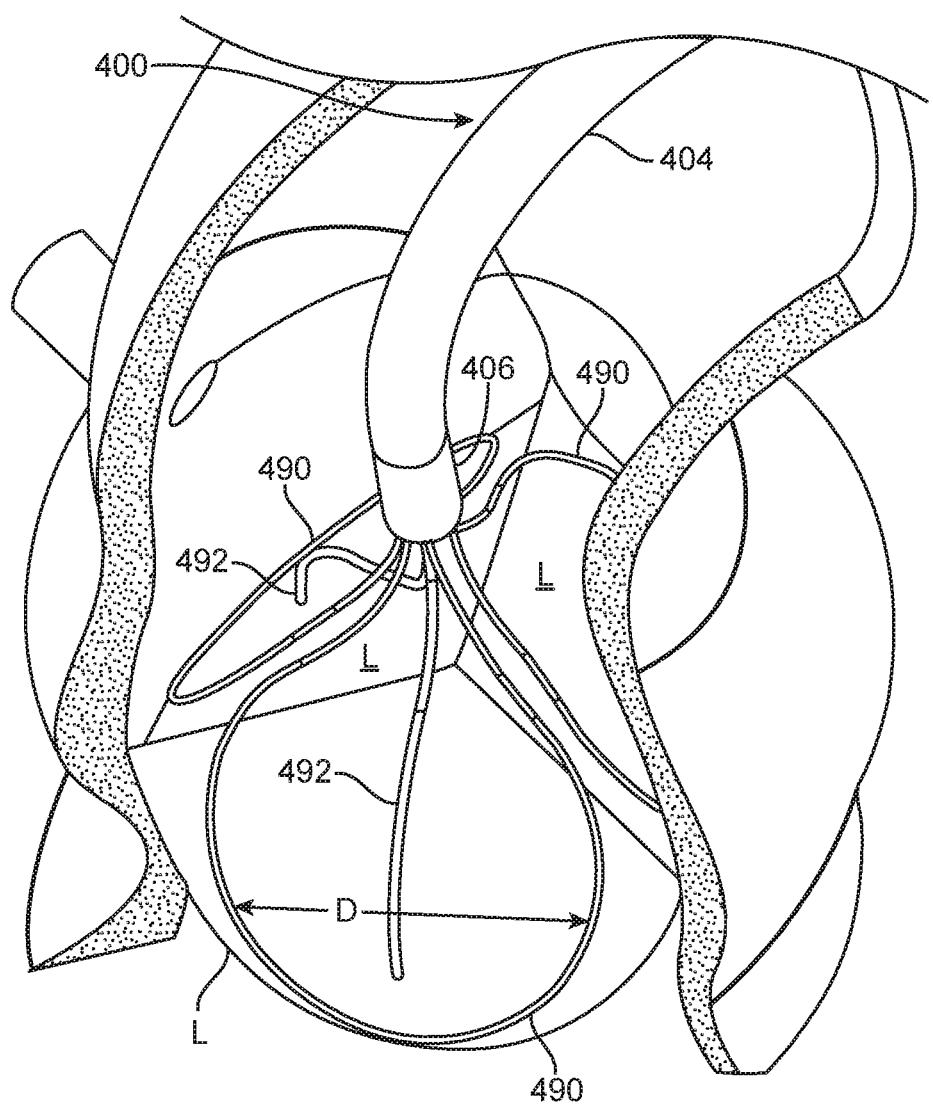
FIG. 17 is a partial, perspective view of the device of FIG. 16 illustrating a plurality of feelers extending from the outer catheter.

Referring now also to FIGS. 16-20, which illustrate yet another embodiment of a valve preparation or disabling device 400. In this embodiment, the valve preparation device 400 includes an outer catheter 404 containing a plurality of loops 490 (e.g., three loops). The loops 490 are maintained within the outer catheter 404 in a delivery arrangement and can be distally advanced as is shown in FIG. 16 to protrude from a distal end 406 of the outer catheter 404. The loops 490 can be formed of a wire material such as nitinol, for example, and are configured to align with the leaflets (cusps) L of a heart valve V (e.g., aortic valve). In this way, the loops 490 expand in diameter D as they extend from the distal end 406. In one embodiment, one end of each wire forming each loop is fixed and the second end is distally advanced such that the loops 490 bow outwardly and expand in diameter D. Once the loops 490 are expanded into the arrangement shown in FIG. 16, they are each gently advanced and seated in the leaflets L, one loop 490 per leaflet L. In another embodiment, one loop 490 could be advanced and seated in one leaflet L prior to advancing and seating the other two loops 490 in their respective leaflets L. In other words, the loops 490 can be seated sequentially.

Figure 18:
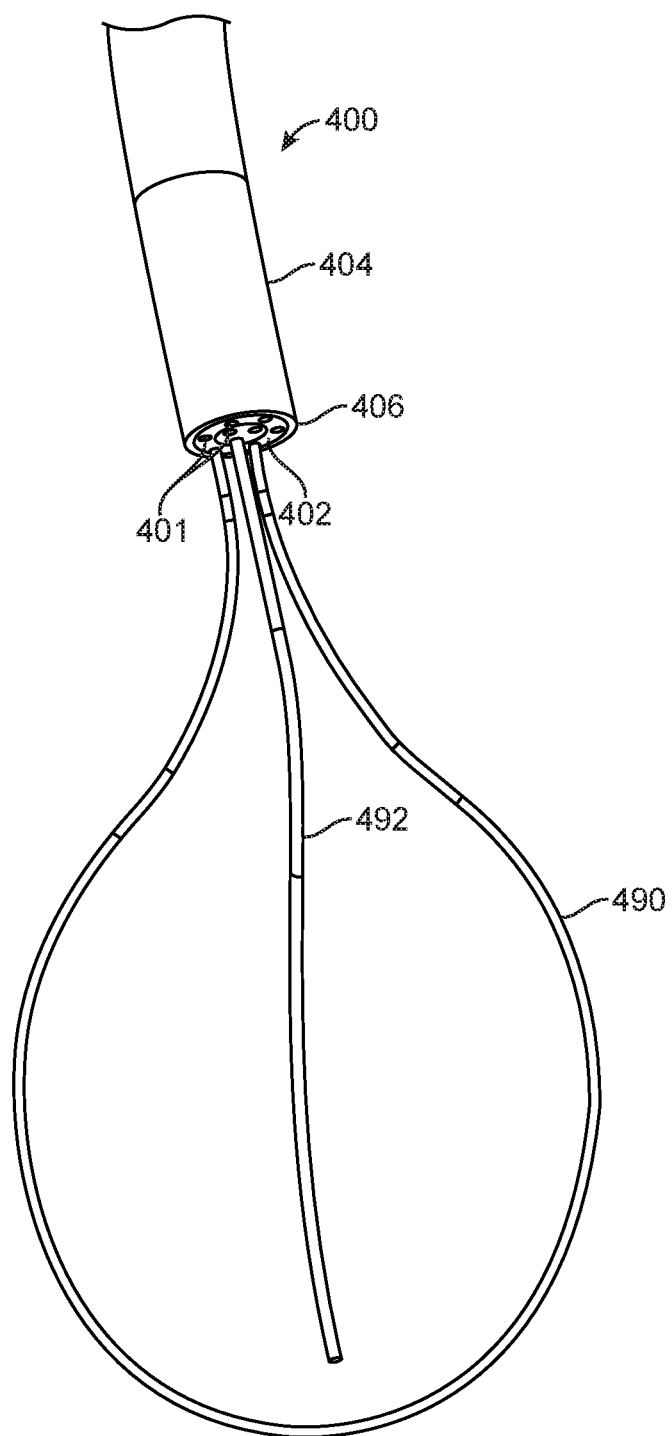
FIG. 18 is a partial, perspective view of the device of FIGS. 16-17.
Figure 19:
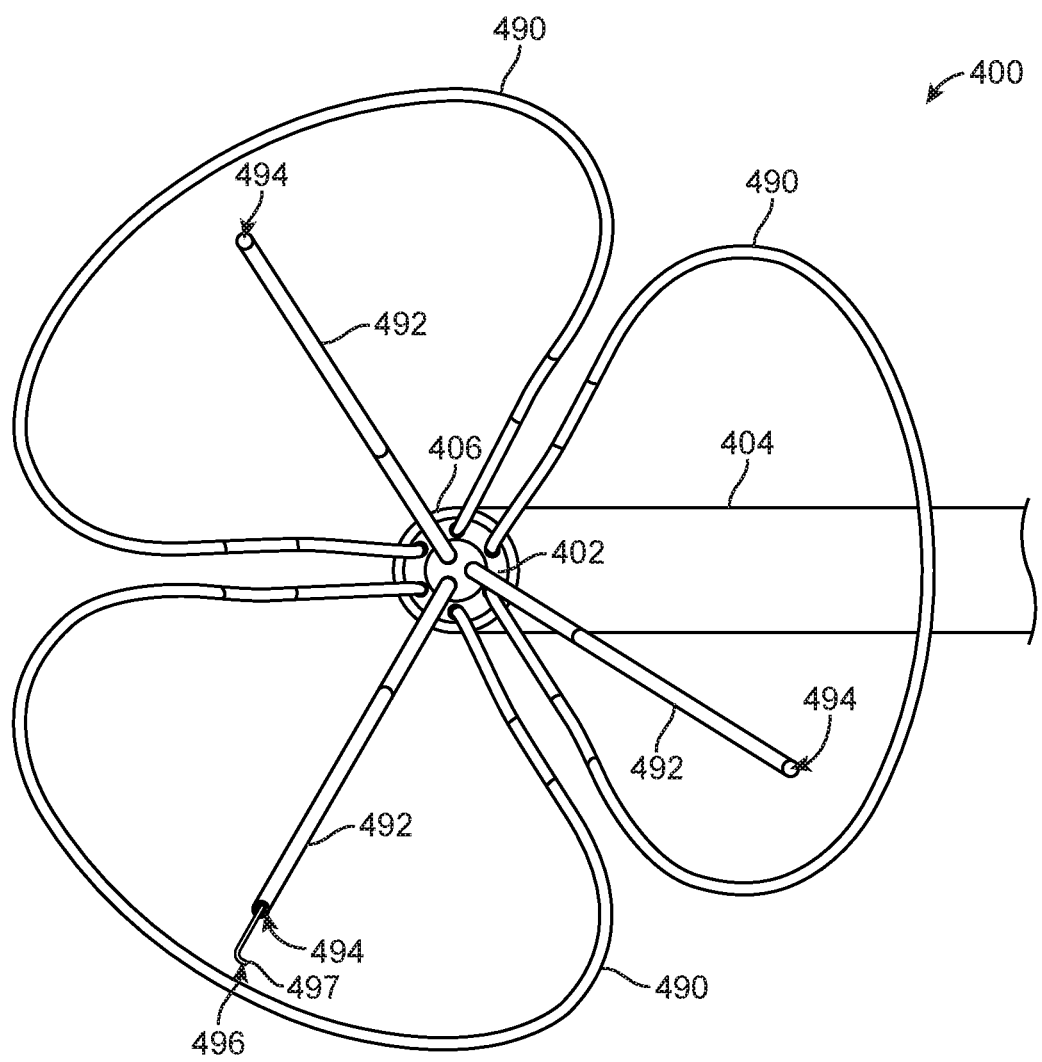
FIG. 19 is a partial, bottom view of the device of FIGS. 16-19 and illustrating a severing element, such as a blade, that can be provided within each of the feelers.

The valve preparation device 400 further includes an inner catheter 402 that is coaxial with outer catheter 404. Associated with each loop 490 are one or more feelers 492 (e.g., two) that can be advanced from within the inner catheter 402 from respective apertures 401 (generally referenced) tow within a respective loop 490 as is best shown in FIGS. 18-19 (only one loop 490 and feeler 492 shown in FIG. 18). Each feeler 492 is a tube including a lumen 494 through which a severing element 496 can be directed to puncture and sever or cut the respective leaflet L. Only one severing element 496 is shown in FIG. 19, however, the other respective severing elements 496 can be identically configured. As indicated with like reference numbers, all feelers 492 are identically configured. In the illustrated embodiment, the severing element 496 is a hooked blade as shown in FIG. 19. Examples of suitable severing elements 496 include, but are not limited to, a sharp wire with a formed curl or barb, which can puncture the leaflet L and then anchor through the leaflet, a wire connected to a source of RF energy for both puncturing the leaflet and cutting the leaflet, a rod or wire having a blade section, which would be held at the leaflet location once the wire punctures and anchors through the respective leaflet.

The plurality of feelers 492 extend from the distal end 406 and directed to each leaflet L where cuts are desired. The feelers 492 may have pre-set curves or include a steering mechanism in order to guide them to the desired location on the respective leaflet. In one example embodiment, one feeler 492 is directed to the left coronary cusp/leaflet and one feeler is directed to the right coronary cusp/leaflet. Each feeler 18-19, the device 400 includes an inner catheter 402 that is nested within the outer catheter 404. As indicated above, the inner catheter 402 ensures that once the loops 490 are extended and seated within the leaflets L, the feelers 492 are oriented in the respective leaflets L as well. Once seated in the leaflet(s) L, each feeler 492 delivers the severing element 496.

Figure 20:
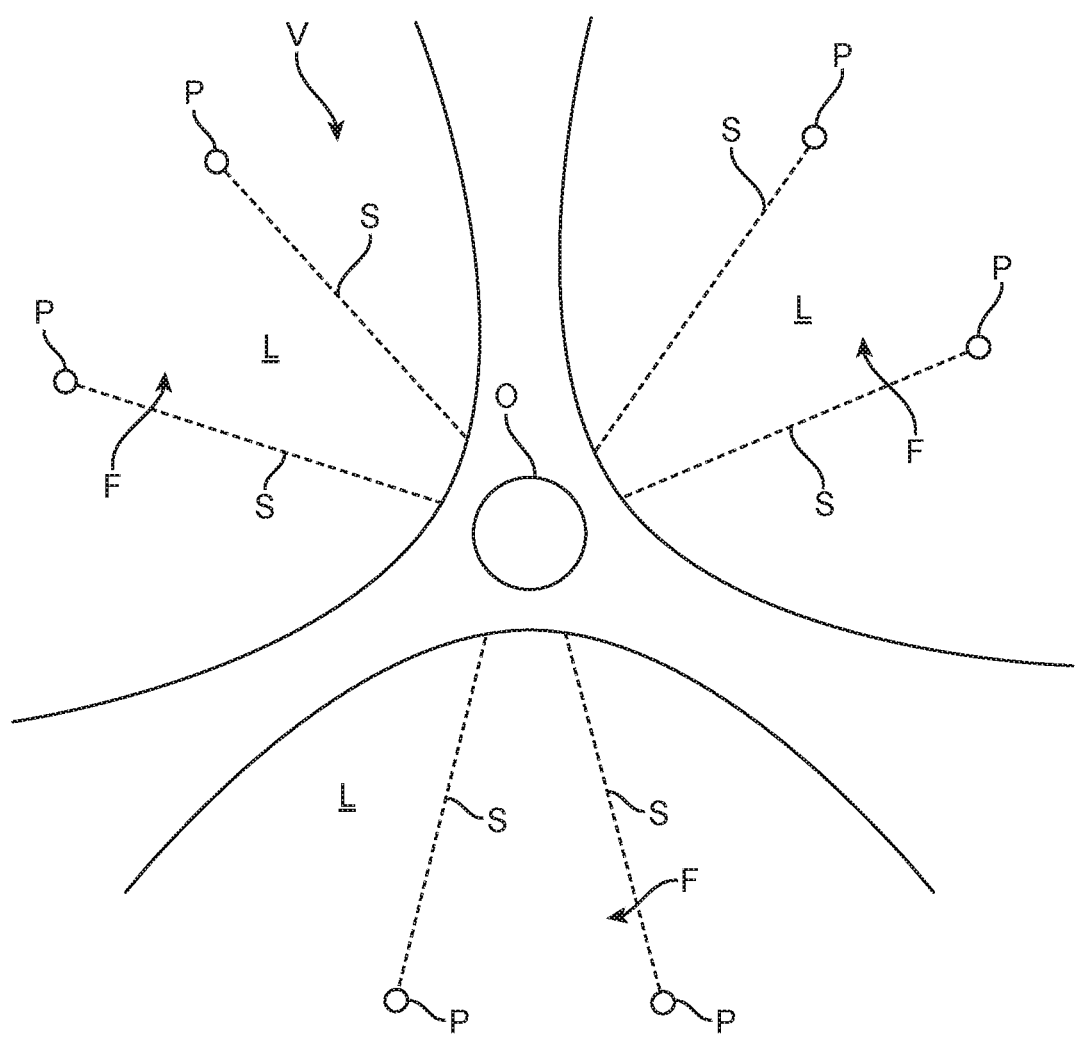
FIG. 20 is a schematic illustration of one possible result of a procedure of the disclosure in which slits are formed in all three leaflets with the device of FIGS. 16-19.
Figure 21C:
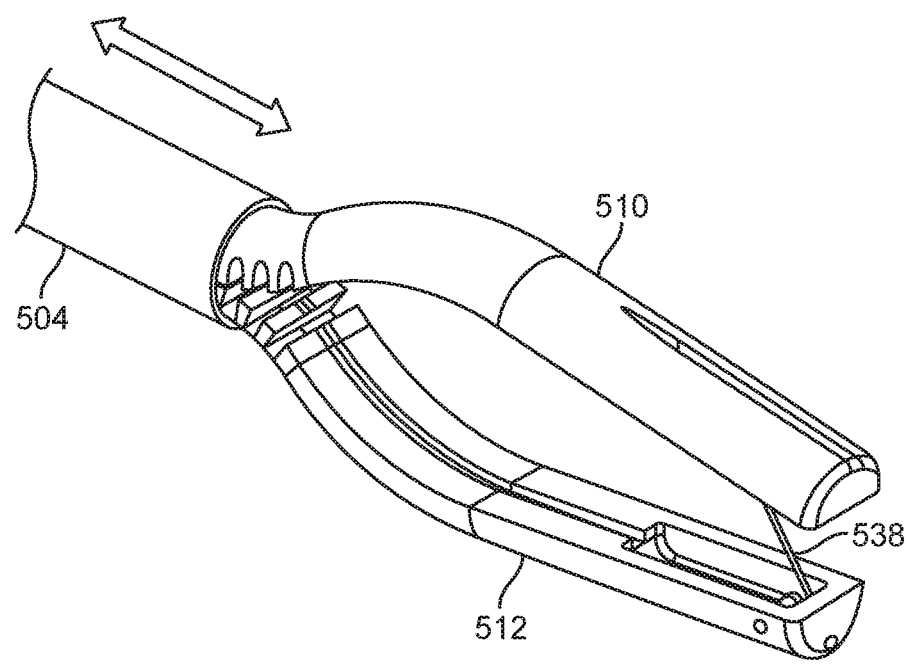

Once all of the severing elements 496 have punctured through the desired leaflets L (e.g., two punctures P formed per leaflet/cusp L), the inner catheter 402 is retracted, causing simultaneous slitting of the leaflets L. Severing/cutting can also be achieved via RF energy or mechanical cutting with a sharp section 497 (e.g. a blade or the like) of the severing element 496. FIG. 20 illustrates slits S in all three of the valve leaflets L of the valve V. It will be understood, however, that more or fewer slits S may be formed, while adequately ensuring coronary flow. It will also be understood that slits S may only be formed in only one or two leaflets L (specifically those associated with the right and/or left coronary ostia) rather than all three. The slits S define tissue flaps F in the leaflet L that allow each leaflet L to be folded and/or pushed downward during deployment of a prosthetic heart valve. In another embodiment, the leaflets L are not folded down but splayed open when pinned against the aorta as described previously. It will be understood that any of the devices of the disclosure can be used to form slits and flaps in one or more leaflets as shown in FIG. 20.

Referring now also to FIGS. 21A-22F, which illustrate another embodiment of a valve preparation or disabling device 500. In this embodiment, the valve preparation device 500 has an inner catheter 502 and an outer catheter 504. The outer catheter 504 being coaxially aligned and arranged to slide over the inner catheter 502. At a distal end 506 of the inner catheter 502 is a first jaw 510 and a second jaw 512, wherein the jaws 510, 512 can pivot with respect to each other. In one example, the jaws 510, 512 are made of a flexible material (e.g., plastic such as polyetheretherketone, nylon or the like), which is optionally blended or coated with a radiopaque material. Attached to the second jaw 512 is a severing element 538. In the illustrated embodiment the severing element 538 is an electrode 538 that can be energized to puncture and cut a respective leaflet L1 when the device 500 is engaged with and pulled along the leaflet L1. In some embodiments, the severing element 538 is spring biased to the position of FIG. 21B (i.e. outwardly extending at an angle with respect to the second jaw 512) and can be delivered in a delivery arrangement, substantially parallel to the second jaw 512 and retained in the delivery arrangement with compressive pressure applied from the first jaw 510. In some embodiments, severing or cutting is achieved by generating a plasma on the electrode 538 via an external power supply (not shown). For a monopolar design, an external counter electrode 539 (schematically shown in FIG. 21A) is mounted on a patient's skin via a patch. For a bipolar design, the counter electrode 539 is mounted on the device 500. The first and second jaws 510, 512 can be made of a polymeric material or a mix of polymer and metal, for example. One objective may be to balance the materials of the jaws 510, 512 to have enough metal to be visible under fluoroscopy but not so much metal as to interfere with echogenicity of the device. In some embodiments, the only portion of the jaws 510, 512 that capture leaflet L1 are the distal portion containing the puncturing electrode 538, thus allowing the electrode 538 to cut the leaflet L1 as it is pulled proximally relative to the leaflet L1 (in other words the jaws/electrode 510, 512, 538 can only move relative to the leaflet L1 if the device 500 is not clamping the leaflet L1 at some location).

Figure 22A:
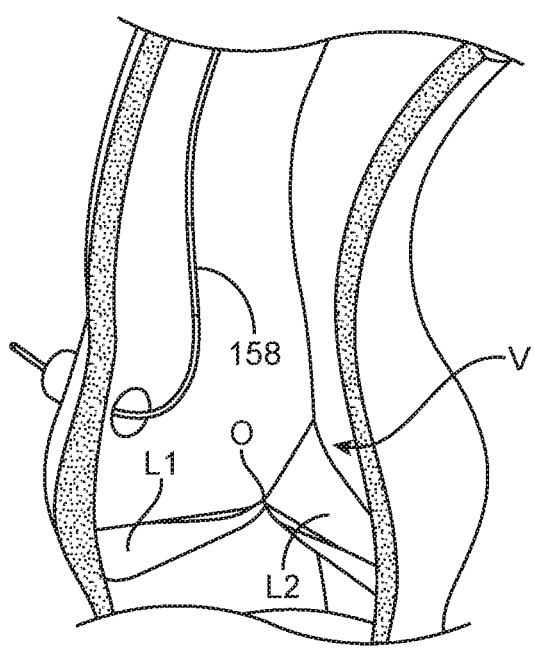
FIGS. 22A-22F illustrate one example method of using the device of FIGS. 21A-21C.
Figure 22B:
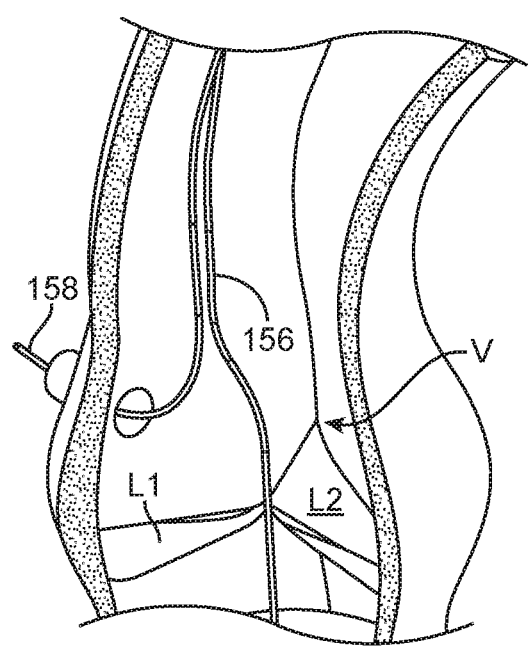
Figure 21D:
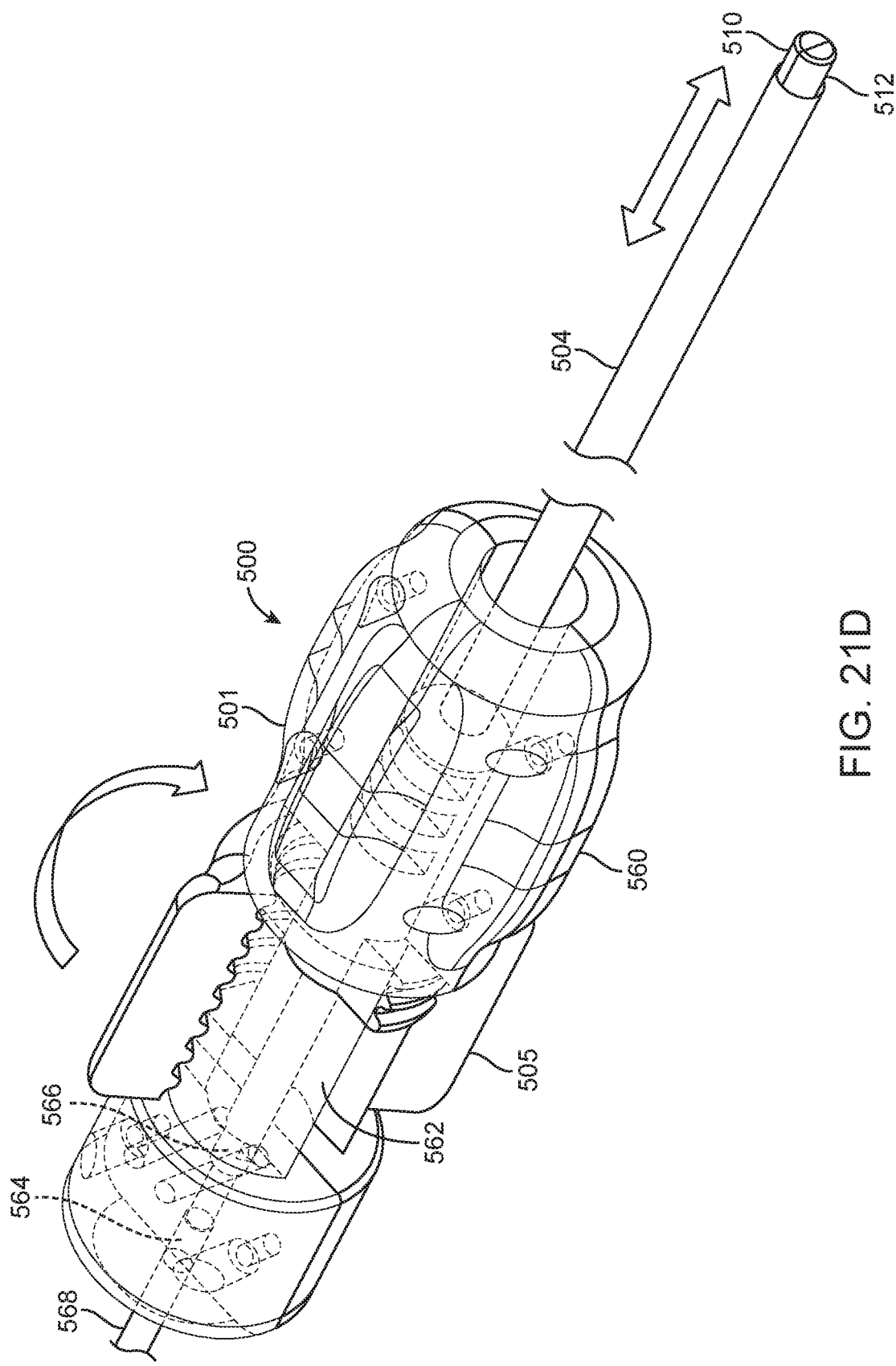
FIG. 21D is a perspective view of the valve preparation device of FIGS. 21A-21C in a delivery confirmation.
Figure 22C:
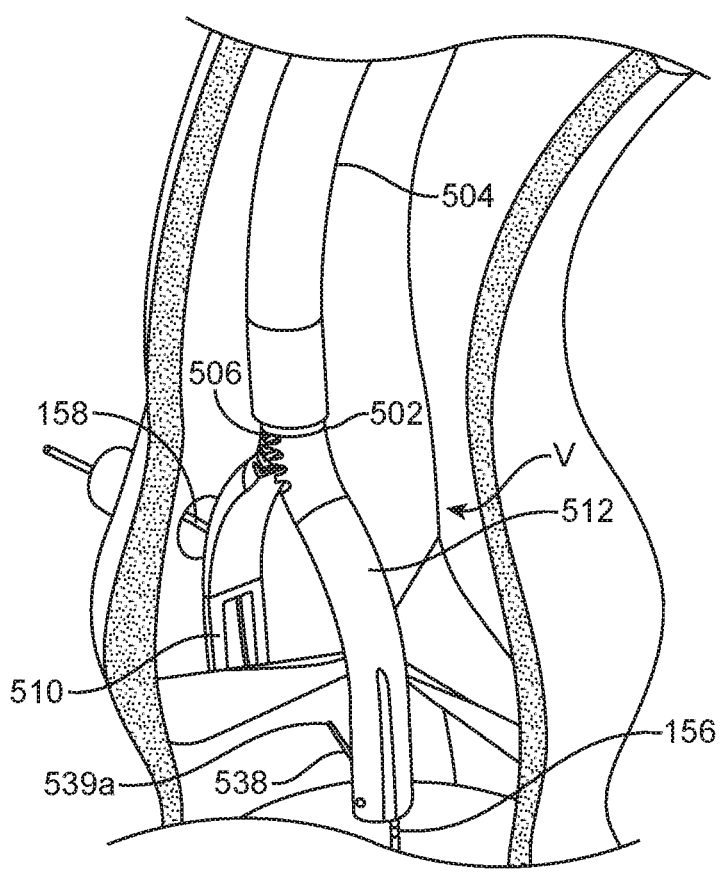
Figure 22D:
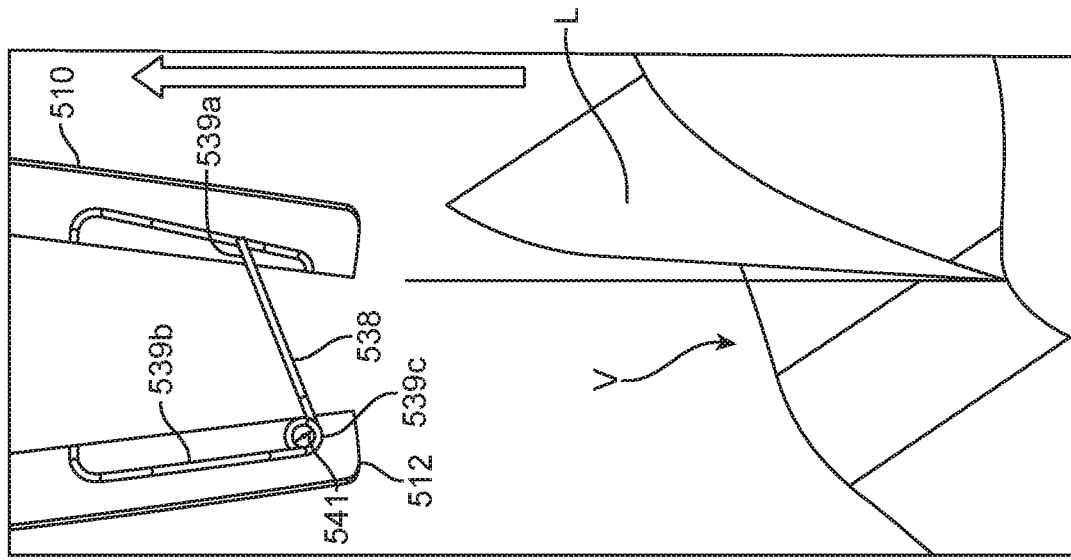
Figure 22E:
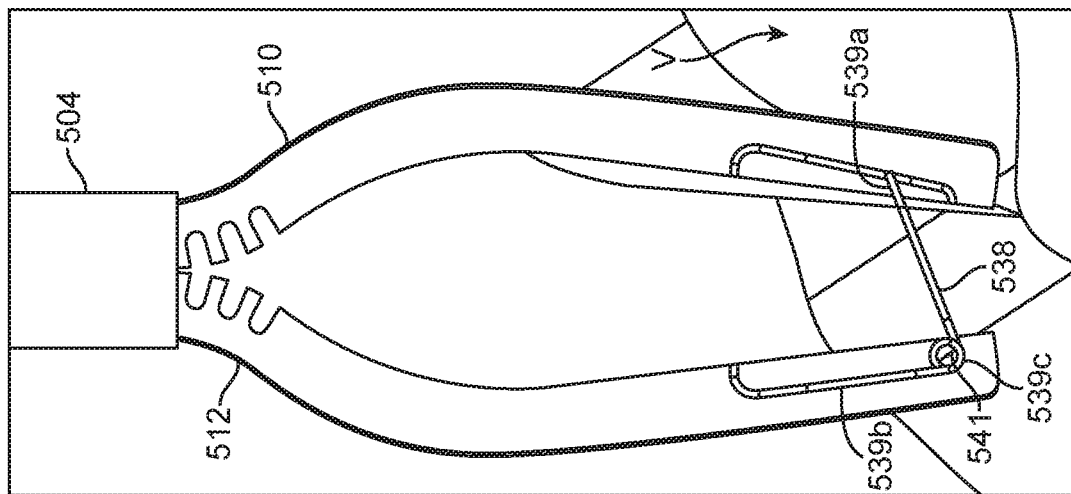
Figure 22F:
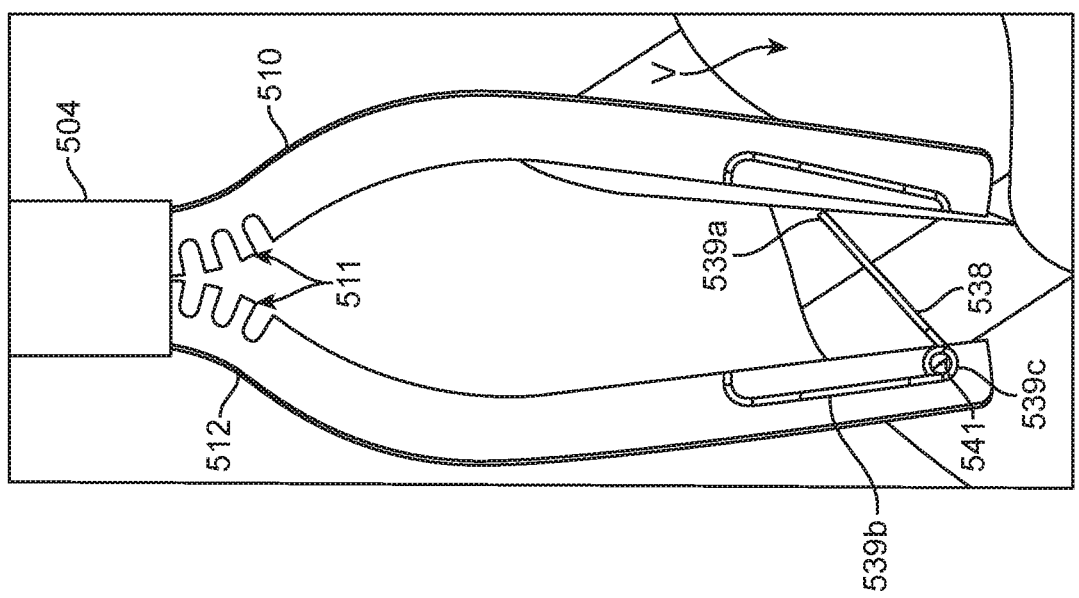

Example methods of using the valve preparation device 500 can include delivering the device 500 in a closed arrangement (FIG. 21D) in which the first and second jaws 510, 512 are drawn together into a cylindrical configuration and covered by the outer catheter 504 for delivery to a heart valve V having a plurality of leaflets L1, L2, etc. via a retrograde approach. Proximal with respect to the leaflets L1, L2, the jaws 510, 512 are transitioned to the open arrangement shown in FIG. 21C, for example. The jaws 510, 512 are transitioned by retracting the outer catheter 504 so that the jaws 510, 512 spring into their natural, biased position. The second jaw 512 is then inserted through the valve opening O, past the leaflets L1, L2, while the first jaw 510 remains on the opposing side of the respective leaflet L1. In this way, the first jaw 510 and the second jaw 512 are positioned on opposing sides of one leaflet L1. Once the severing element 538 is in position, the severing element 538 is energized to first pierce the leaflet L1 and then the severing element 538 can be pulled across the leaflet L1 to create a slit in the leaflet L1. The process can be repeated until the leaflet(s) L1, L2, etc. are sufficiently removed and/or severed, as desired. In some embodiments, the valve preparation device 500 is delivered to one leaflet with the grasper 150, as described above with respect to similar embodiments. In some embodiments, as illustrated in FIGS. 22A-22C, the device 500 can be guided by guide wires 156, 158. As shown in FIG. 22A, one coronary guide wire 158 is placed in the right or left coronary, followed by insertion of a LV guide wire 156 into the left ventricle. The device 500 would then be advanced to the ascending aorta over both guide wires 156, 158. Alternatively, the device 500 could be advanced over the coronary guide wire 158 to the ascending aorta and then the LV guide wire 156 could be positioned, especially if the device is combined with steering mechanisms). In addition, the device 500 can be advanced over the LV guide wire 156 without use of the coronary guide wire 158. In this example, the outer catheter 504 can be used to inject contrast in order to determine the position of the jaws 510, 5132 within the aortic root. In particular reference to FIG. 22C, once the device 500 is advanced into the aortic root so that a distal end of the first jaw 510 (the jaw proximate the coronary) is in the belly of the leaflet L1, the location of the device 500 is configured by the location and orientation of the guide wires 156, 158. The severing element 538 (e.g., electrode) is activated in FIG. 22D resulting in a puncture in leaflet shown graphically in FIG. 22E. The severing element 538 is activated again and retracted proximally to cut the respective leaflet L, as shown in FIG. 22F.

Figure 23:
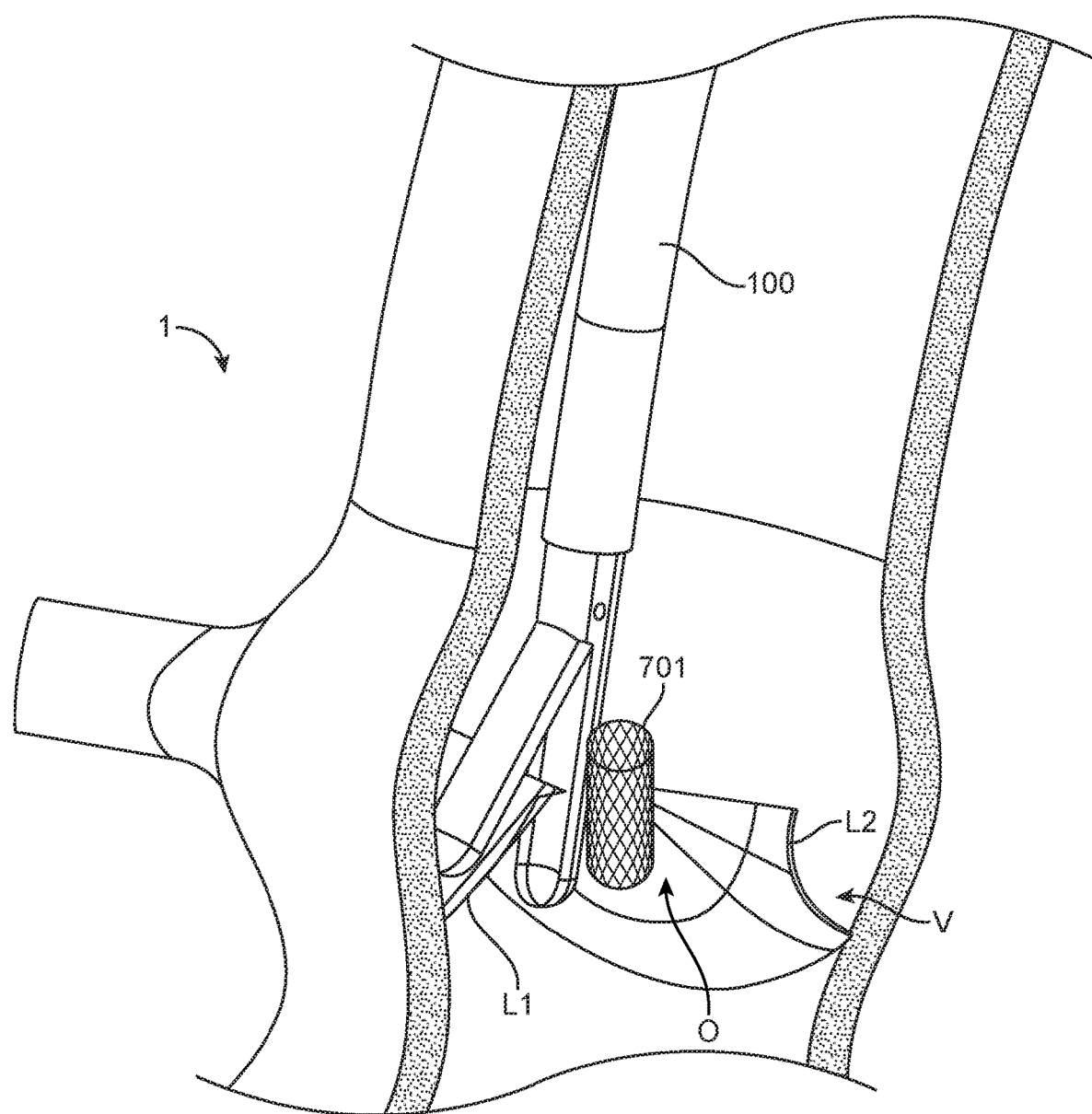
FIG. 23 is a schematic illustration of a system including the valve preparation device of FIG. 1A and a frame positioned within a valve opening for supporting the leaflets during a procedure of the disclosure.

Any of the devices disclosed herein can be provided as part of a system 1 further including a frame 701 for stabilizing the leaflets L1, L2 as is schematically shown in FIG. 23. The frame 701 can be a stented prosthetic heart valve which is to be implanted at a patient's failing heart valve or can be a stent frame of any of the type known in the art, such as those used for prosthetic heart valves, and is generally a metal mesh cylinder. Such frames 701 have a compressed arrangement and an expanded arrangement. The frame 701 can be made of as shape-memory material to be biased into the expanded position or can mechanically be expanded via balloons or the like. In such systems 1 and related methods, the frame 701 is positioned within the valve opening O and is partially or fully expanded in any known manner. The partially expanded or expanded frame 701 restricts and stops movement of the leaflets L1, L2, etc. to allow cutting or a similar leaflet removal procedure to be completed. Therefore, during use, the valve preparation device 100 is positioned radially outwardly with respect to both the frame 701 and the valve opening O. Once the leaflet severing and optional removal procedure is completed in accordance with any of the above-disclosed embodiments, the frame 701 is removed or can be implanted as the replacement stented prosthetic heart valve, if applicable. In some embodiments, the frame 701 could be deployed with suture loops and then recaptured or deployed out of approximately ⅔ out of a capsule and then recaptured within the capsule for removal. In various embodiments, the inflow end of the frame includes a temporary valve to control blood flow during the procedure. In other various embodiments, the frame 701 can include positioning arms (not shown) to assist in positioning and/or grasping the leaflets L1, L2 for severing. In all disclosed methods, a temporary valve may optionally be deployed (not shown, e.g., in the Hufnagel position) to provide blood flow management during the procedure. Although valve preparation device 100 is shown in FIG. 23, it is to be understood that the frame 701 can be used in conjunction with any of the valve preparation devices disclosed herein as part of system 1.

Referring now in addition to FIGS. 24A-28, which collectively illustrate components of another valve preparation or disabling device 800 and optional modifications to components thereof. The device 800 includes a catheter 802 (only a short length of which is shown), which can extend proximally to a handle (e.g., see handle 120 of FIG. 1A or handle 501 of FIG. 21A). At a distal end 806 of the catheter 802 is a balloon 810 made of a compliant, resilient material. The balloon 810 has a deflated arrangement for transcatheter delivery (FIG. 24A) and an inflated arrangement (FIG. 24B). The device 800 further includes an inflation lumen 804a for connection to an inflation source (not shown). The inflation lumen 804a may extend within the catheter 802 to the balloon 810 and can extend through the handle assembly or be otherwise connected to the inflation source. The balloon 810 includes one or more severing elements 838, such as electrodes, which longitudinally span a length of the balloon 810. In the case where the severing elements 838 are electrodes, each electrode can include a lead (not visible) that extends to the handle assembly. In one embodiment, when the balloon 810 is in the inflated arrangement, the balloon 810 (and thus electrodes 838) can be advanced and rotationally aligned to the desired location within the valve V (e.g., adjacent the leaflets L, see FIGS. 25A-25D) and can be selectively energized to sever one or more leaflets L such that slits formed in the leaflet to either cut or remove the leaflet. Optionally, the balloon 810 can be partially inflated, then the electrodes 838 can be energized and the balloon 810 then further inflated so that the outward movement of the balloon 810 assists in cutting the leaflet tissue.

There are many advantages for using one or more electrodes 838 for cutting/severing leaflets L. When one or more electrodes are utilized, the cutting function can be controlled independently of balloon inflation and the cutting function can be localized by independently turning on appropriate electrodes (one or more of 838) and the power to each electrode can be independently controlled. Additionally, safety can further be improved during introduction, delivery and removal of the device as the electrodes can be turned off whereas a mechanical cutter still retains its cutting edge during introduction, delivery and removal.

Figure 24A:
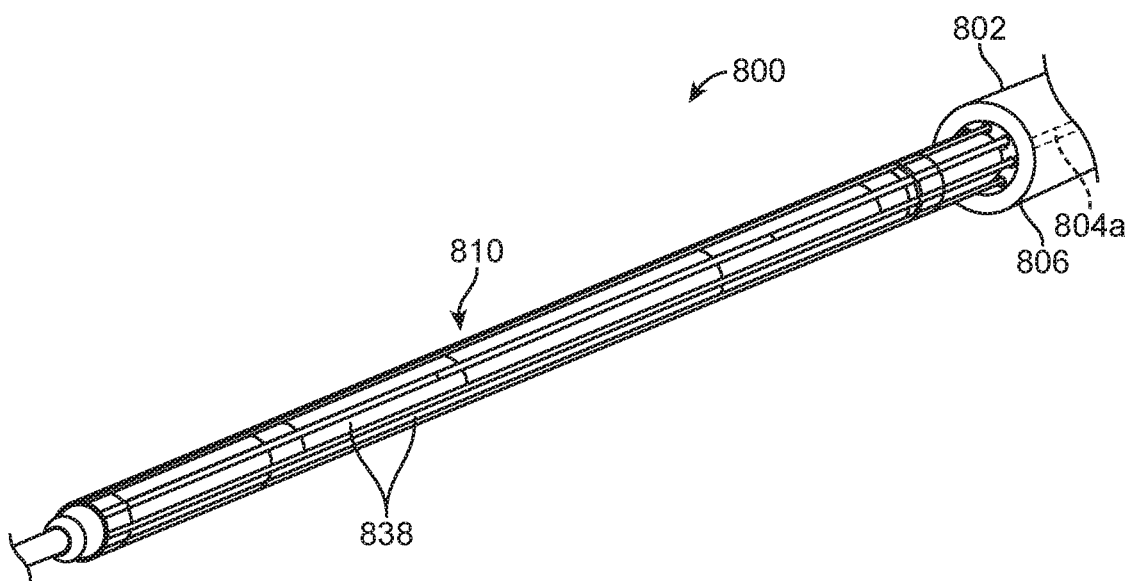
FIG. 24A is a partial, perspective view of an alternate valve preparation device having a catheter and a balloon in a deflated arrangement, the balloon including at least one electrode.
Figure 24B:
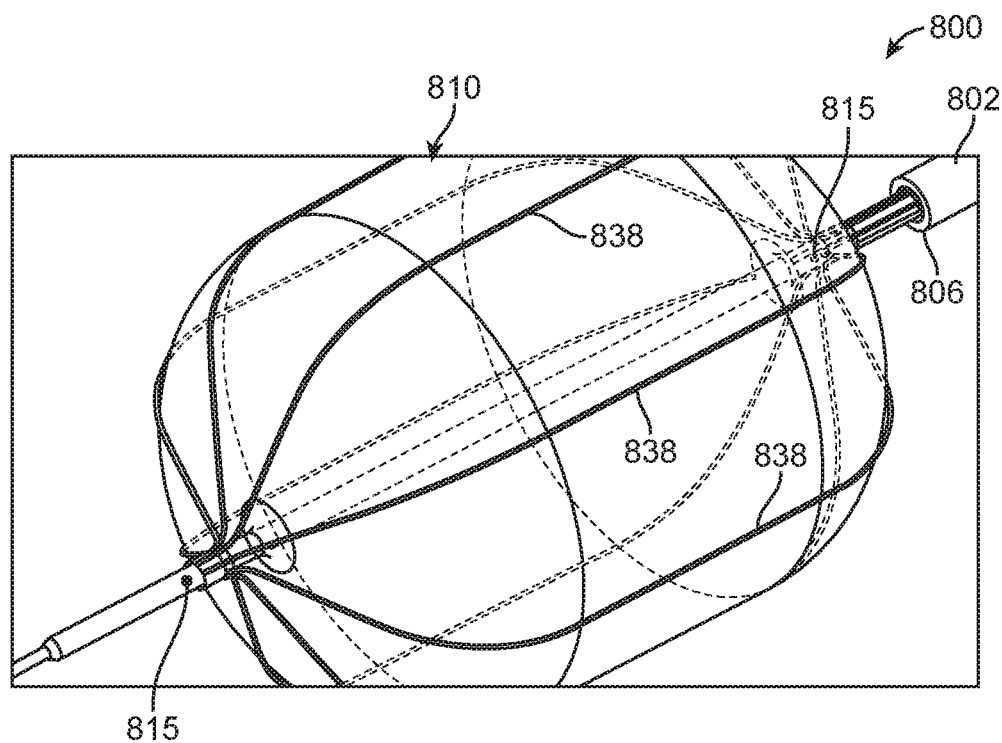
FIG. 24B is a partial, perspective view of the device of FIG. 24A having the balloon in an inflated arrangement.
Figure 24C:
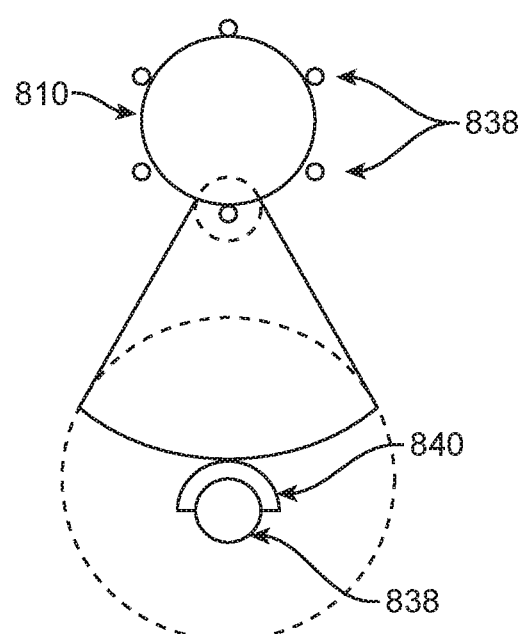
FIG. 24C is a cross sectional and enlarged schematic illustration of the balloon of FIG. 24A.
Figure 25B:
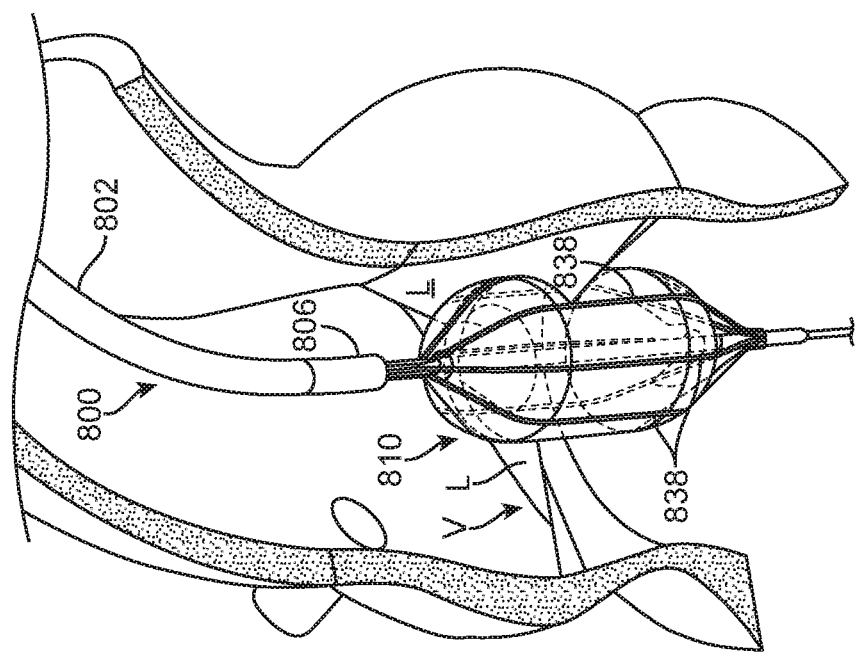
FIGS. 25A-25D illustrate one example method of using the device of FIGS. 24A-24C.
Figure 25A:
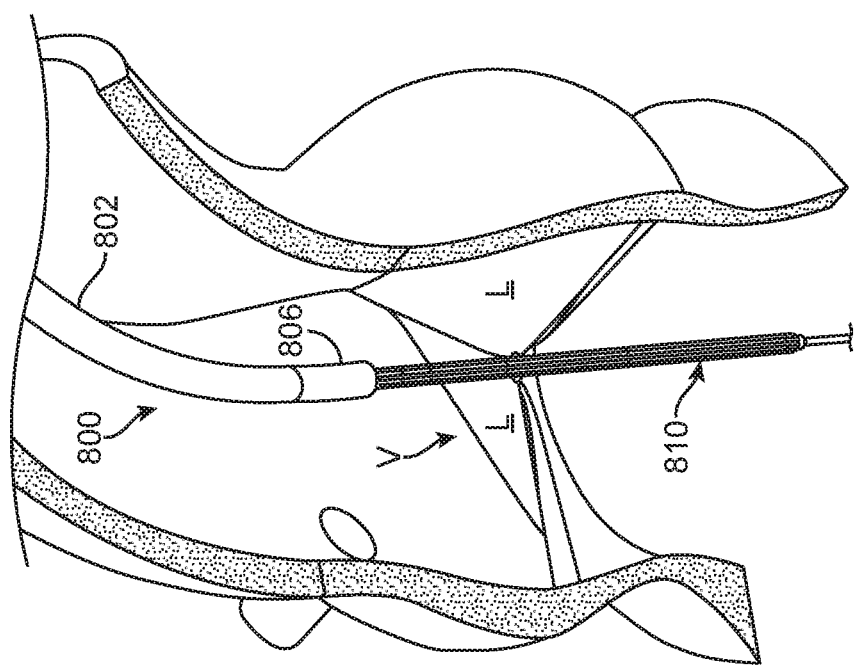
Figure 25C:
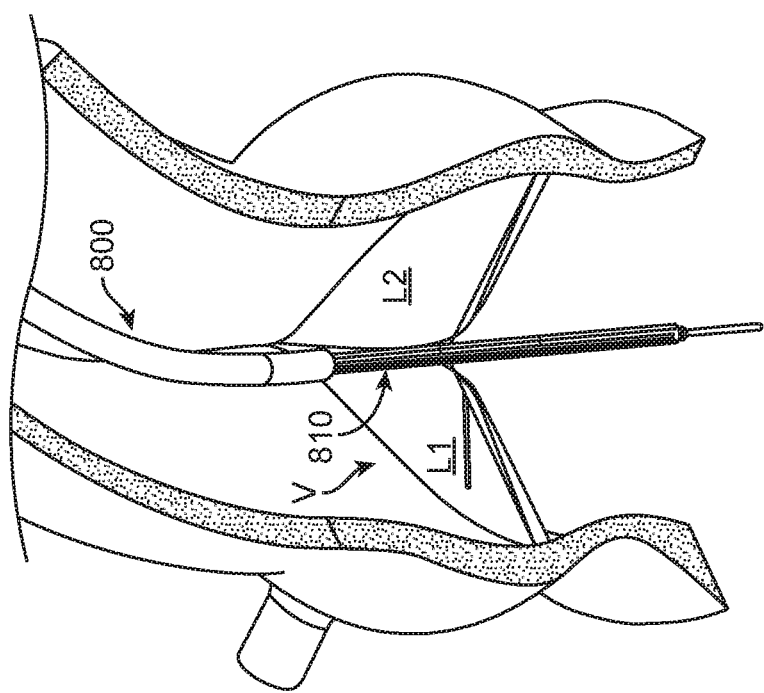
Figure 25D:
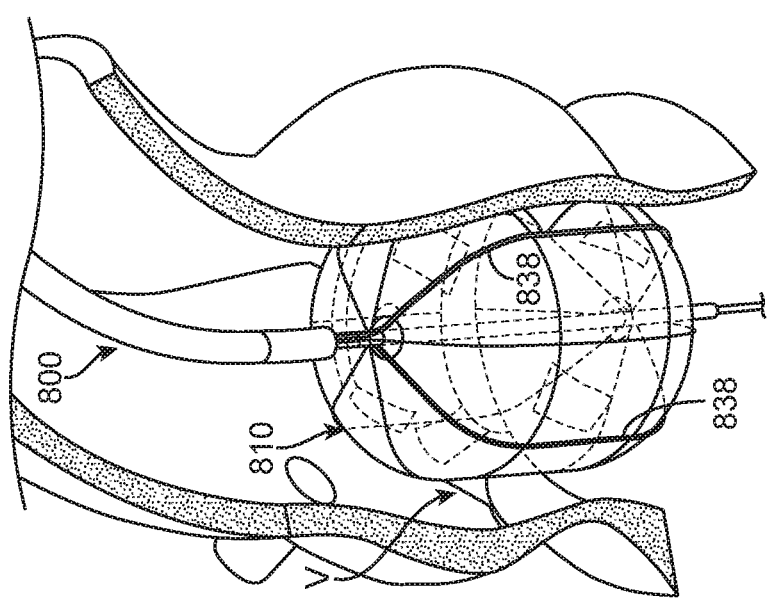

As schematically depicted in FIG. 24C, each electrode 838 can optionally have a circular cross section and, in addition, each electrode 838 can be provided with an insulator 840 spanning a portion of the circumference of the electrode 838 to direct plasma outward rather than toward an interior of the balloon 810. In one embodiment, each insulator 840 spans about 180 degrees of the circumference of one respective electrode 838 along a full length of the electrode 838. Optionally, the electrode 838 can be constructed of a flat wire with a rectangular cross-section or wire with an oval cross-section.

In embodiments where the balloon 810 includes a plurality of severing elements 838 (i.e. electrodes) the electrodes 838 can be distributed radially around a circumference of the balloon 810. In one embodiment, six electrodes 838 are provided (see, in particular, FIG. 24C). Fewer or more electrodes 838 are also envisioned. If all powered together, the electrodes 838 would provide six cuts in the valve V being treated. Alternatively, the electrodes 838 could be individually powered and selectively energized in any quantity and pattern desired. In this way, the catheter 802 would not need to be rotated to achieve multiple cuts or to otherwise be oriented.

Figure 26:
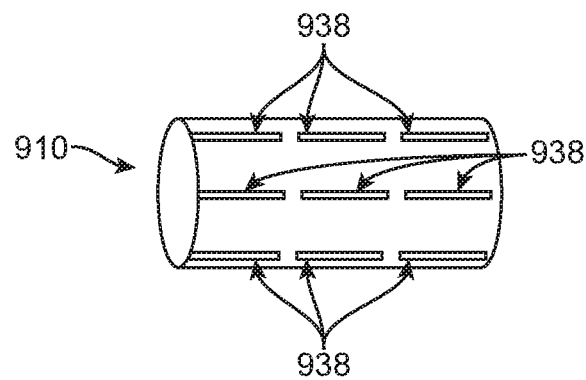
FIG. 26 is a partial, side, schematic illustration of an alternate balloon having a plurality of electrodes arranged longitudinally along the balloon and around a circumference of the balloon.
Figure 27:
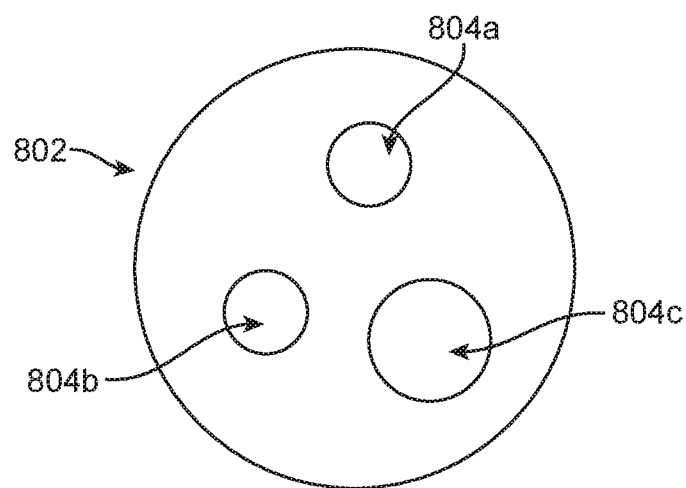
FIG. 27 is one example of an interior configuration of the catheter of the device of FIG. 24A.

It is further envisioned that each electrode 838 of FIGS. 24A-24B could be segmented either via insulation or otherwise. As schematically illustrated in FIG. 26, each electrode 938 of a balloon 910 utilized in a device of the disclosure (e.g., device 800) could be longitudinally subdivided into separately powered elements that could be selectively energized. In one illustrative example, a 9 mm long electrode 938 could be subdivided into three 3 mm long electrodes that are separately powered to allow a cut of 3, 6, 9 mm to be performed, depending on the anatomical need, by energizing the appropriate number of electrodes.

The catheter 802 can take a variety of configurations. In one optional configuration shown in FIG. 27, the catheter 802 includes three lumens 804a, 800b, 800c. The first lumen 804a can serve as the inflation lumen, the second lumen 804b can serve configured to accept a guide wire and the third lumen 804c can be used to provide blood flow when the balloon 810 is in the inflated arrangement and is otherwise configured not to block blood flow. The third lumen 804c communicates with a patient's blood vessel on both sides of the balloon 810 and, thus, allows blood to enter one side and exit the other, providing blood flow through the blood vessel during inflation of the balloon when the balloon might otherwise preclude blood flow.

Figure 28:
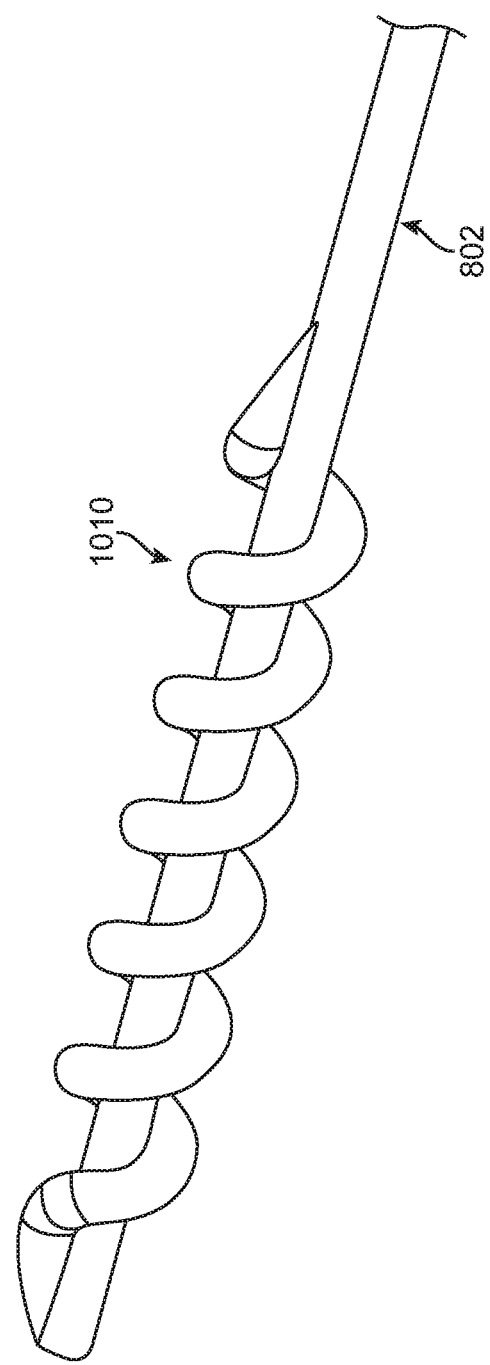
FIG. 28 is an optional spiral configuration of the balloon of the device of FIG. 24A.

The balloon of embodiments of the disclosure can take a variety of configurations. One alternate example is shown in FIG. 28. In this example, the balloon 1010 can have a spiral shape when in the inflated arrangement. In this way, blood can flow in a helical fashion from a proximal end to the distal end of the balloon and thus, allow perfusion when the balloon 1010 is in the inflated arrangement. The balloon 1010 can include one or more severing elements or electrodes similar to those shown and described with respect to FIGS. 24A-24B and 26, as well as other disclosed herein, for example.

Example methods of using the embodiments of FIGS. 24A-28, can include delivering the valve preparation device 800 in a deflated arrangement in which the balloon 810, 910, 1010 is deflated to a heart valve V having a plurality of leaflets L1, L2, etc. via a retrograde approach (see also, FIG. 25A-25D). Once the severing element(s) 838, 938 are in position, one or more severing elements(s) 838, 938 are energized or otherwise activated to pierce and create a slit in the leaflet(s). The process can be repeated until the leaflet(s) L1, L2, etc. are sufficiently removed and/or severed, as desired. Optionally, the severing can be a partial severing that does not extend the full thickness of the leaflet but that is sufficient to improve the flexibility or compliance of the respective leaflet. The devices of FIGS. 24A-28 can further be used with a grasper or positioning device as disclosed herein.

Figure 29A:
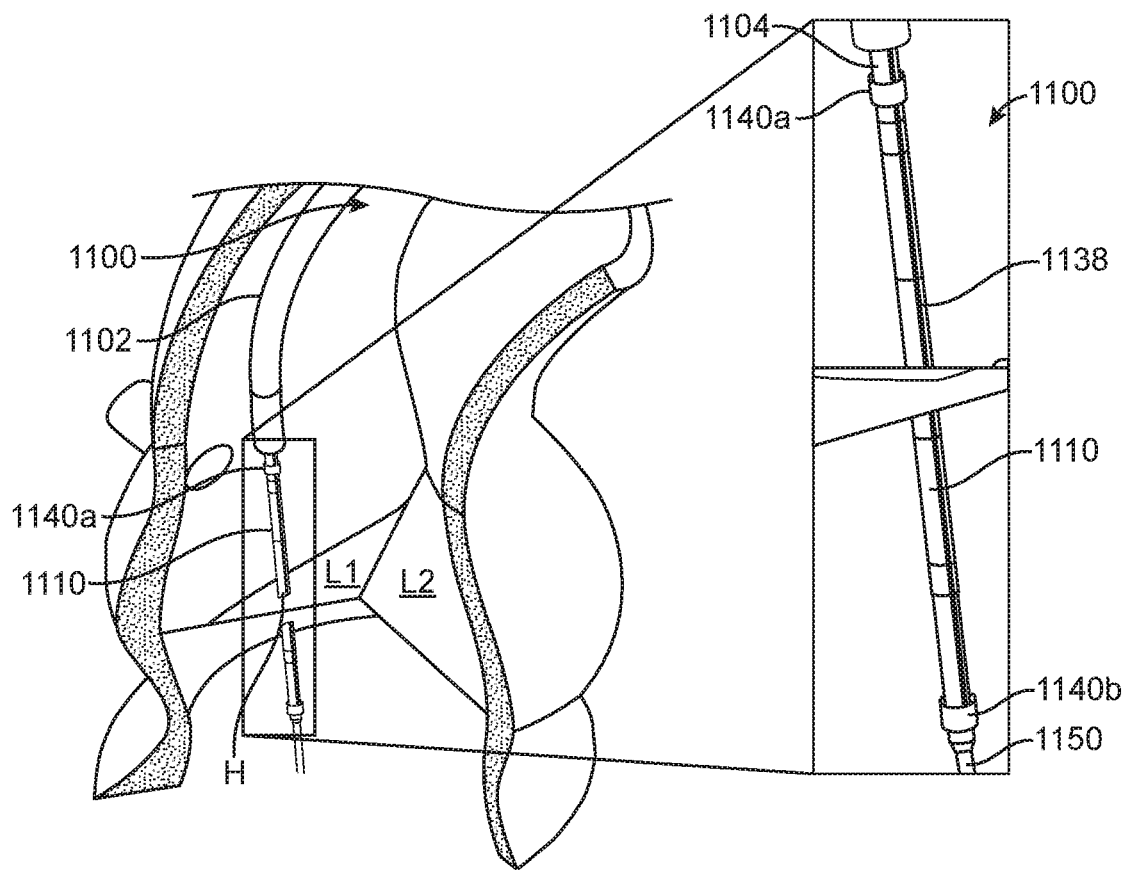
FIGS. 29A-29C illustrate an alternate device including a balloon having an electrode and methods of treating a leaflet with the electrode.
Figure 29B:
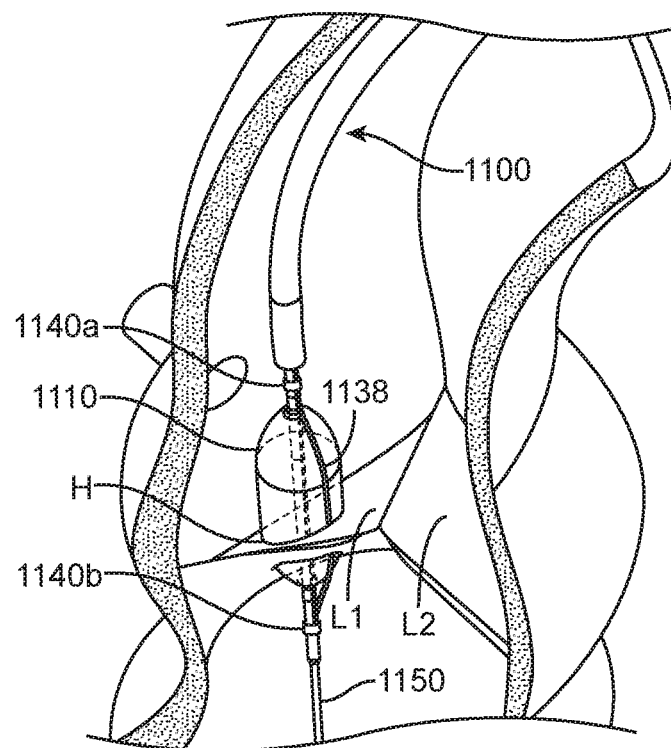
Figure 29C:
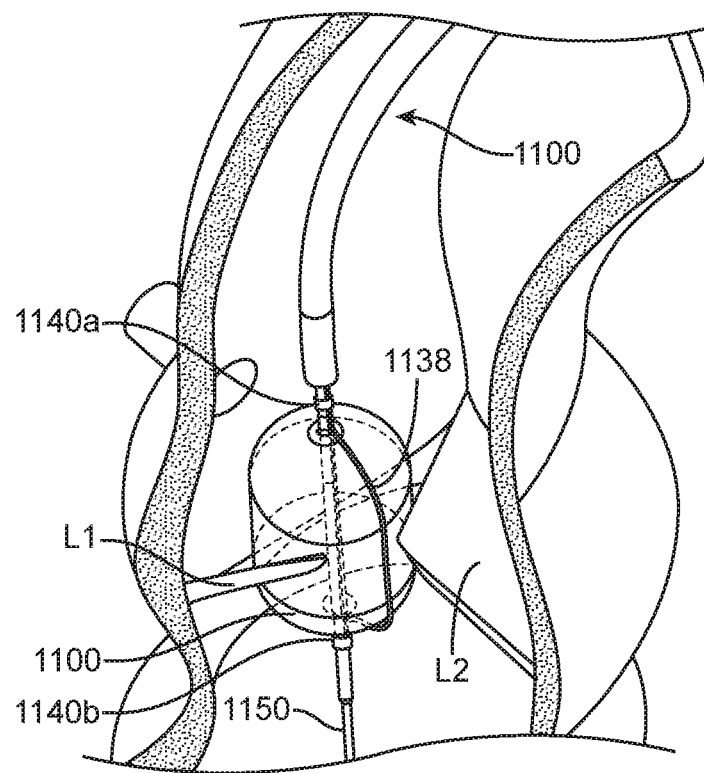

In yet another embodiment, the severing elements disclosed herein can be biased outwardly from the balloon. Such a valve preparation or disabling device 1100 is collectively depicted in FIGS. 29A-29C. In this embodiment, the device 1100 includes an outer catheter 1102, which receives an inner catheter 1104 that supports a balloon 1110 having one or more severing elements 1138. The balloon 1110 is made of a compliant material and operates similar to those other balloons disclosed herein. The severing element(s) 1138 can be a wire form electrode, which is made of a memory shape material to be biased outward with respect to the balloon 1110 to enhance engagement with the leaflet(s) L1, L2, etc. In one implementation, at least one severing element 1138 includes a proximal attachment ring 1140a that is affixed to the inner catheter 1104 and a distal attachment ring 1140b positioned on the inner catheter 1104 distal the balloon 1110. The distal attachment ring 1140b can slide along the inner catheter 1104 to account for foreshortening of the severing element 1138 as the balloon 1110 expands due to inflation. In one embodiment, only a section of a length of the severing element 1138 is active or non-insulated (via an insulating coating). In one example, the section of active severing element is roughly half of a full length of the balloon 1110.

One example method of the disclosure includes puncturing a hole in a leaflet L1 by whatever means preferred as disclosed herein. Then, a guide wire 1150 is positioned through a puncture/hole in leaflet L1 that can be formed in any way disclosed herein, for example. In one example, the outer catheter 1102 is tracked around the aortic arch to a location in the ascending aorta. The inner catheter 1104, maintaining the balloon 1110, is pushed distally out of the outer catheter 1102 and then advanced through the hole in the leaflet L1 to a depth such that an active portion of the severing element 1138 extends from below the hole to above the leaflet L1. In other words, the balloon 1110 is positioned so that an active portion of the severing element 1138 is in contact with or very close to the leaflet L1. In some examples, the balloon 1110 may be rotationally oriented so that the severing element is adjacent a center of the leaflet L1. Once the severing element 1138 is oriented, as desired, the severing element 1138 may be activated to sever the respective leaflet L1. Repeat procedures can be conducted on the same or any remaining leaflets, as desired.

Figure 30:
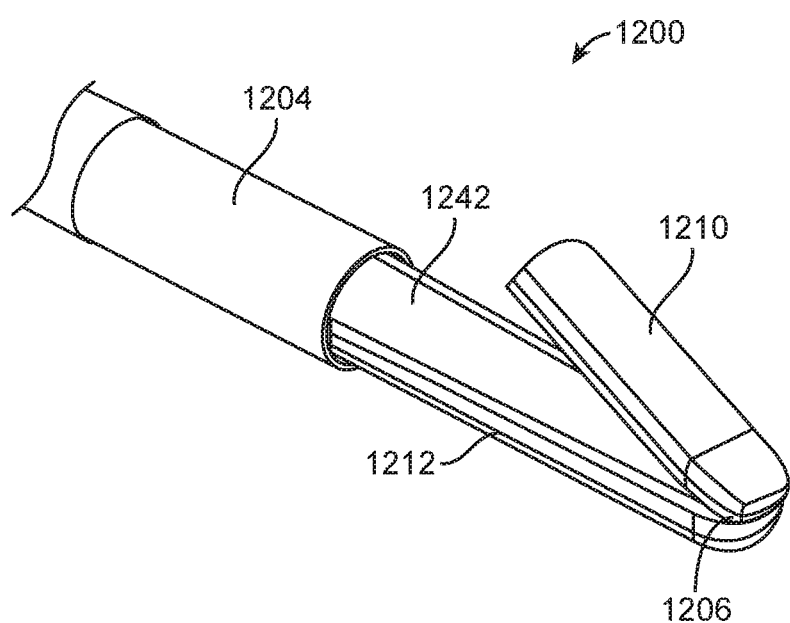
FIG. 30 is a partial, perspective illustration of an alternate device.

In one method, the valve preparation devices disclosed herein can be used to manage the anterior mitral leaflet during TMVR procedures, especially if the leaflet is unusually long. If the leaflet is not appropriately managed, it can either fold anteriorly into the LVOT causing obstruction with systolic anterior motion (SAM), or posteriorly under the TMVR device affecting valve performance (trans-valvular flow obstruction). Therefore, leaflet removal, or portions thereof, would be advantageous for TMV function prior to, or following, a TMVR procedure. For mitral leaflets, some embodiments herein may reverse the mounting of the grasper/severing element relative to the deliver or outer catheter. For example, the jaws of any disclosed devices may be mounted relative to the catheter body as shown in FIGS. 3-4 for an apical approach, whereas the jaws of any disclosed devices may be reversed for a trans-septal or aortic approach (such that the opening of the jaws faces the proximal end versus the distal end of the outer catheter) as shown in FIG. 30, for example. In particular, FIG. 30 illustrates a valve preparation or disabling device 1200, which can be configured largely similar to that of FIGS. 1A-2 except as explicitly stated. The device 1200 includes a first jaw 1210 and a second jaw 1212 that are pivotally connected at a pivot point 1206, which is located at the distal end of the device 1200, distal to outer catheter 1204. In this way, the jaws 1210, 1212 can grasp a leaflet in receiving area 1242 in a trans-septal or aortic approach. Jaws 1210, 1212 can otherwise be configured and function identical to those in FIGS. 1A-2.

Another alternative is to have the grasper aligned perpendicular to the centerline of the outer catheter. In contrast to aortic valve leaflet cutting or severing prior to a TAVR procedure, cutting or severing the mitral valve leaflet prior to a TMVR procedure can provide an advantage of reducing native valve leaflet motion allowing easier grasping and severing of the leaflet. In one embodiment, as shown in FIGS. 5-8, valve preparation device 200 can be used to modify an anterior mitral leaflet to help prevent LVOT obstruction during a TMVR procedure.

Figure 31:
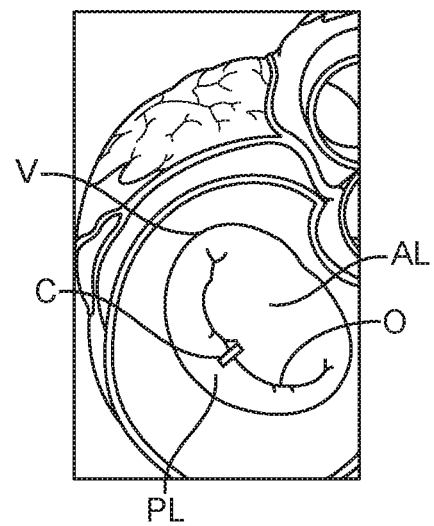
FIG. 31 is a schematic representation of a mitral valve in which a ligating device (a clip) has been implanted connecting an anterior mitral leaflet to a posterior mitral leaflet.

Referring now in addition to FIG. 31, it is common to treat a diseased valve, e.g., a mitral valve V, by securing a pair of leaflets, e.g., anterior and posterior leaflets AL, PL of a mitral valve, together in one or more locations with a ligating device C. Examples of ligating devices C include, but are not limited to, MitraClip®, LigaClip® or any other ligating clips, sutures or the like for securing to a valve, e.g., a mitral valve, for the purpose of preventing regurgitation. Similarly, the leaflets, e.g., AL, PL, can be attached surgically using an Alfieri Stitch, also known as a "bowtie procedure" or "edge-to-edge repair". Although such clips C and other ligating devices are often clinically successful in reducing regurgitation through valve opening O, there are cases where ligating devices do not sufficiently reduce the regurgitation and a subsequent intervention is required. As transcatheter mitral valve replacement (TMVR) progresses, becomes approved by regulatory bodies and thus is more widely available, there will be cases where a ligating device patient will benefit by placement of a TMVR or some other interventional procedure by which the repair is effectively reversed. However, before a TMVR is placed, the previously implanted ligating device(s) C would need to be removed or otherwise disabled to allow for the full opening of the native valve for implantation of a replacement (or to perform another interventional procedure). Aspects of the disclosure relate to disabling devices and methods for removing such ligating device C and/or disabling ligating devices C spanning the opening O to interconnect valve leaflets, e.g., mitral valve leaflets AL, PL.

Figure 32:
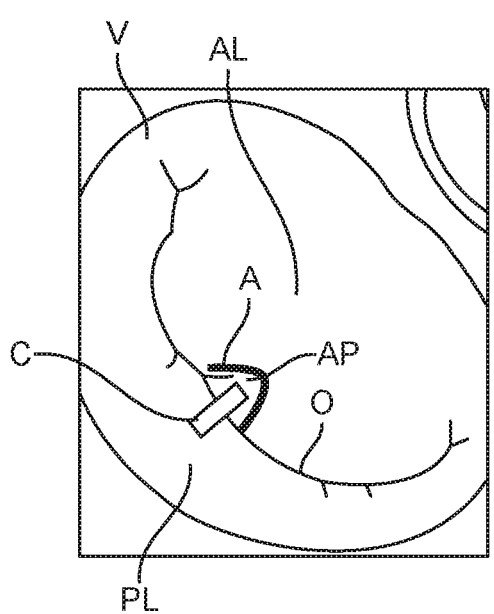
FIG. 32 is a schematic representation of the mitral valve of FIG. 31 illustrating the placement of a cut or slit to be made in the mitral valve according to various embodiments to separate the anterior leaflet and the posterior leaflet.

Referring now in addition to FIG. 32, in various embodiments, generally, a transcatheter valve preparation or disabling device of the disclosure is used to sever/cut the anterior leaflet AL of the mitral valve V in such a way as to release a previously implanted clip C (or other ligating device) from just the anterior leaflet AL and leave the clip C attached to the posterior leaflet PL. Conversely, the valve preparation or disabling device can be used to sever or cut just the posterior leaflet PL in such a way as to leave the clip C attached to the anterior leaflet AL. FIG. 32 illustrates an area A in which the anterior leaflet AL is to be severed to free the leaflets AL, PL and disable the clip C. In practice, the severed area A transfers a small portion AP of the anterior leaflet AL (and the clip C) to the posterior leaflet PL, thus effectively "disabling" the clip C and allowing the opening O to fully open, thereby allowing a prosthetic heart valve (not shown) to be subsequently implanted within the opening O. In this way, the portion AP effectively becomes part of the posterior leaflet PL after the area A has been severed (or vice versa if the posterior leaflet PL is severed). In other words, after disabling the clip C or other ligating device, the opening O is unobstructed and ready for receiving a replacement prosthetic mitral heart valve or conducting an interventional procedure on the mitral valve V.

Generally, in one variation or embodiment, an area A' surrounding the entirety of the clip C including the portion AP and portion PP of the posterior leaflet PL within the area A' (see FIG. 33) is removed from the patient with the valve preparation or disabling device. Therefore, the clip C is also removed from the patient. In this case the valve preparation or disabling device further includes an apparatus for grabbing the leaflets AL, PL or clip C prior to severing the leaflets AL, PL so that the clip C can be removed from the patient after severing the leaflets AL, PL. Examples of a suitable apparatus (not shown) include a snare, a corkscrew anchoring device or the like as well as other leaflet engaging elements disclosed herein. This embodiment can add complexity to the overall valve preparation or disabling device or system but provides the benefit of fully removing the clip C from the mitral valve V for removal from the patient.

Figure 34:
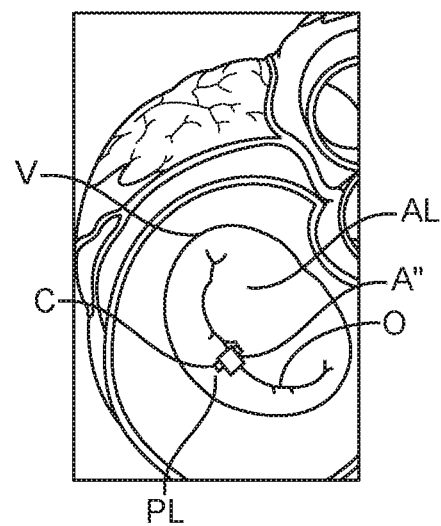
FIG. 34 is a schematic representation of the mitral valve of FIG. 31 illustrating the placement of a cut or slit to be made in the ligating device to separate the anterior leaflet and the posterior leaflet.

In yet another variation or embodiment, the valve preparation or disabling device can be used to sever the ligating device C itself as is schematically shown in FIG. 34. In this way, the ligating device C (e.g., clip, suture or the like) is severed into two pieces so that although one piece of the ligating device C remains connected to each leaflet AL, PL, the opening O is unobstructed so that a replacement prosthetic heart valve (not shown) can be implanted within the opening O.

Figure 35:
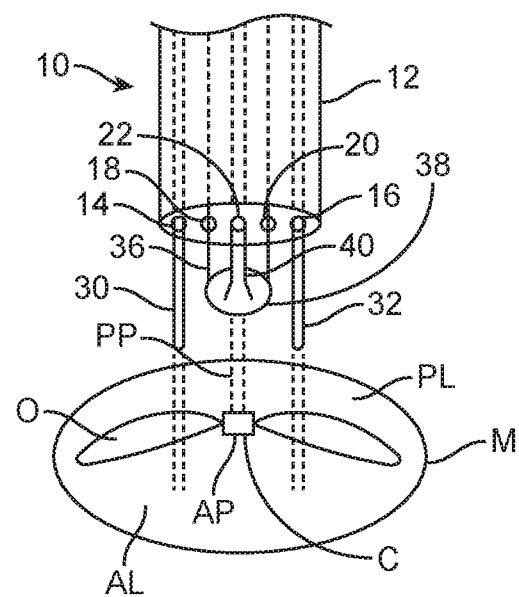
FIG. 35 schematically illustrates a portion of one disabling device and method of disabling the clip or other ligating device via removal of the ligating device from a patient with the disabling device.

A distal end of one suitable valve preparation or disabling device 10 for performing the methods of the disclosure is schematically represented in FIG. 35. The valve preparation or disabling device 10 includes a catheter 12, which can be relatively rigid to approach the clip C from the ventricle (e.g. a trans-atrial access) or could be more flexible for a trans-septal approach. The catheter 12 includes lumens 14, 16 for receiving two positioning posts 30, 32. The catheter 12 further includes lumens 18, 20 for receiving a lunar or circular shaped wire 36 having a severing element (e.g., an electrode 38 configured to generate a plasma), the wire 36 being mounted between the two positioning posts 30, 32. It is envisioned that the electrode 38 can be replaced with other severing elements capable of severing leaflets AL, PL to disable the clip C. In addition, the valve preparation or disabling device 10 includes yet another lumen 22 in which tongs 40 can be positioned. The tongs 40 can be proximally retracted within the lumen 22 during delivery of the valve preparation or disabling device 10 and can be distally advanced at least partially out of the lumen 22 to grasp the clip C and any severed leaflet portion AP, PP proximate the clip C for removal from the patient.

Figure 33:
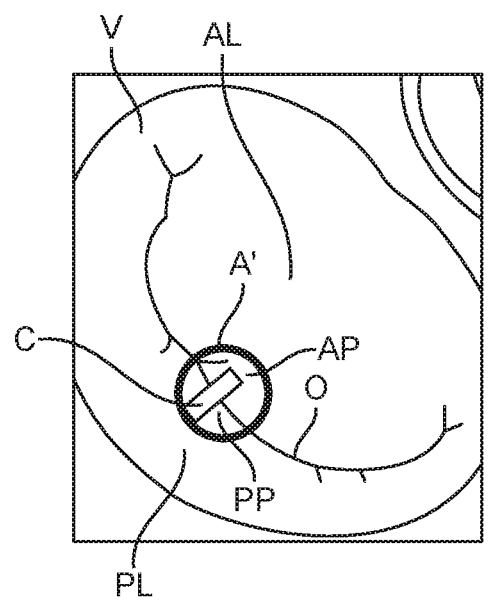
FIG. 33 is a schematic representation of the mitral valve of FIG. 31 illustrating the placement of a cut or slit to be made in the mitral valve according to various embodiments to remove the clip or other ligating device from the mitral valve.

In one example, a patient having the mitral valve V including one or more clips C bridging two 'leaflets' AL, PL together near the midpoint of the opening O. In other embodiments, multiple clips C can be provided along a length of the opening O. The two positioning posts 30, 32 are slid through the opening O, one on either side of the opening O, with one clip C between the positioning posts 30, 32. Once in place, electrode 38 is energized (e.g., with an FT10 power supply or other suitable radio frequency generator, not shown) to generate a plasma that severs one side of the opening O at area A as is generally illustrated in FIG. 33. Therefore, in various embodiments, the electrode 38 extends around the wire 36 more than 180 degrees and in some embodiments, approximately 360 degrees to as effectively release the portions AP, PP from the mitral valve V. It is to be understood that many patients have more than one clip implanted along a length of opening O and, thus, the valve preparation or disabling device 10 could be used sequentially to remove all present ligating devices in a similar manner.

Figure 36:
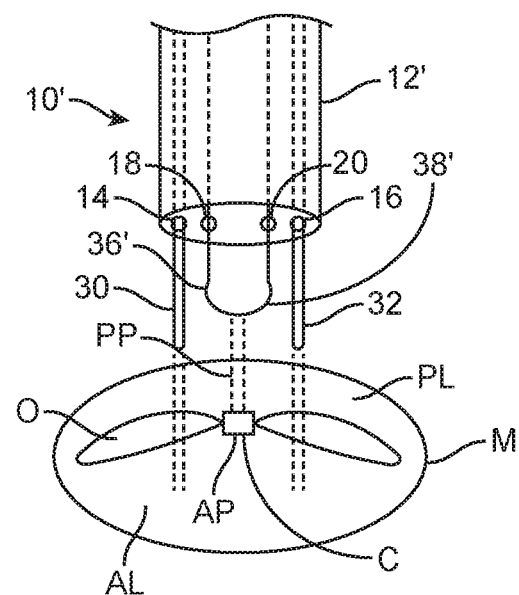
FIG. 36 schematically illustrates a portion of one disabling device and method of disabling the clip or other ligating device via removal of the ligating device from a patient with the disabling device.

Similarly, a valve preparation or disabling device 10', as shown in FIG. 36, can be identically configured to the valve preparation or disabling device 10 of FIG. 35 with the exception of a semi-lunar shaped wire 36' and electrode 38' instead of the lunar shaped wire 36 and electrode 38. In this example, the two positioning posts 30, 32 are slid through the opening O, one on either side of the opening O, with one clip C between the positioning posts 30, 32. Once in place, electrode 38' is energized to generate a plasma that severs one side of the opening O at area A as is generally illustrated and described with respect to FIG. 32. Therefore, catheter 12' need not include lumen 22 and tongs 40 of the embodiment of FIG. 35 as the clip C will remain within the patient after being disabled. It is to be understood that many patients have more than one ligation device implanted along a length of opening O and, thus, the valve preparation or disabling device 10 could be used sequentially to remove all ligating devices in a similar manner.

It is further envisioned that the valve preparation or disabling device 100 of FIGS. 1A-1C, and also disclosed above, is suitable for use with methods for disabling a ligation device C. The valve preparation or disabling device 100 includes the inner catheter 102 and the outer catheter 104 coaxially arranged to slide over the inner catheter 102. At the distal end 106 of the inner catheter 102, the first and second jaws 110, 112 are provided. The pivotally connected jaws 110, 112 can selectively transition from the open arrangement to the closed arrangement. In the open arrangement, the jaws 110, 112 are pivoted away from each other as is shown in FIG. 1A. In the closed arrangement, the first jaw 110 is oriented generally parallel to the second jaw 112, minimizing the profile of the collective jaws 110, 112. Actuation of the first jaw 110 to the open arrangement can be accomplished in a variety of manners. For example, the first jaw 110 can be biased into the open arrangement with a spring or the like (not shown). An elongated member (e.g., suture, wire of the like, not shown) can be connected to the first jaw 110 to pull the first jaw 110 into the closed arrangement. Upon release of tension in the elongated member, the first jaw 110 transitions to the open arrangement due to the bias. The catheters 102, 104 are connected to a handle assembly 120 opposite the distal end 106. As indicated above, the handle assembly 120 can take a variety of forms capable for directing the catheters 102, 104 during a vascular access procedure and includes one or more actuators 122, 124 for controlling movement of the valve preparation or disabling device 100 (e.g., jaws 110/112, catheters 102/104, elongated members, or other elements of the valve preparation or disabling device 100), as desired.

To assist the valve preparation or disabling device 100 in severing one or more heart valve leaflets (referenced as L, L1, L2, AL or PL) for freeing up valve leaflets that have been connected with a ligation device C, each jaw 110, 112 includes a body 130, 132 defining an edge 134, 136 having a severing element 138, 140. In some embodiments, the edge 134, 136 and jaws 110, 112 collectively form a clamshell shape defining a receiving area 142 therebetween. The severing element 138, 140 can span all or a portion of the respective edge 134, 136, as desired. In various embodiments, in the closed arrangement, the severing elements 138, 140 are in contact. Each severing element 138, 140 may be an electrode, plasma electrode, high frequency ultrasound, resistive heating element, cryoablation element or microwave energy element or could be a mechanical cutter such as a blade or the like. Optionally, to reduce the profile of the valve preparation or disabling device 100, the body 130, 132 of one or more jaws 110, 112 can be made of a memory-shape collapsible material (e.g., nitinol wire mesh) and the respective edge 134, 136 can be comprised of a wire (e.g., nitinol wire).

In the variation of FIG. 1C, a channel 113 forms a U shape within the body 132, generally mirroring the path of the edge 136 of the second jaw 112 and distal movement and actuation of a rotary cutter 115'/pusher 117' grinds out a section of leaflet (e.g., leaflet portions AP, PP) that are retained with the jaws 110, 112 and can be removed with removal of the jaws 110, 112, optionally along with clip C. In one implementation, the pusher 117' is a torqueable, flexible wire, cable or the like that can be attached to a motor (not shown) in the handle assembly 120 FIG. 1A) that could actuate rotation of the pusher 117', and correspondingly the rotary cutter 115'. In this embodiment, the rotary cutter 115'/pusher 117' are directed within the channel 113. In one implementation, a second motor (not shown) in the handle assembly 120 or, alternatively, an operator of the device 100 could pull the pusher 117' proximally to bring the rotary cutter 115' all the way around the channel 113. The pusher 117' could optionally include a flexible sleeve (not shown) that is roughly the length of the channel 113 in order to maintain the pusher 117 in the channel 113. Leaflet grindings can be pulled into one catheter 102, 104 via suction applied from the inner or outer catheters 102, 104 or can be captured by a filter (not shown) mounted on the periphery of one catheter 102, 104. It will be understood that the embodiment of FIG. 1C is identically configured to and can be used in the same manner as that of FIG. 1A except as explicitly stated. It will be further understood that the device of FIG. 1B can be used to disable a clip in a similar manner.

Use of the valve preparation or disabling device 100 to create one or more of the severed areas A, A' of FIGS. 31-34 can be accomplished as follows. The valve preparation or disabling device 100 is delivered in the closed arrangement to a mitral valve V including first and second leaflets AL, PL via a trans-apical, trans-atrial access or trans-septal or trans-apical approach. The jaws 110, 112 are pivoted away from each other to the open arrangement. The second jaw 112 is then inserted through the opening O, adjacent one ligation device C, past the leaflets AL, PL, while the first jaw 110 remains on the opposing side of the leaflets AL, PL. In this way, the first jaw 110 and the second jaw 112 are positioned on opposing sides of the leaflets AL, PL so that ligation device C is positioned in the receiving area 142. Once in position, the jaws 110, 112 are brought together into the closed arrangement in contact with one or more leaflets AL, PL. If necessary, the severing element 138, 140 is energized or otherwise actuated to effectuate cutting of the leaflet AL, PL at the severing element(s) 138, 140 or area at which the first and second jaws 110, 112 come into contact. Then, the valve preparation or disabling device 100 can be withdrawn from the patient in the closed arrangement having portions of one or more severed leaflets AP, PP and ligation device C secured between the two jaws 110, 112 area in the same way the disabling device 100 was delivered. The process can be repeated until all ligation devices C are removed, as desired.

Optionally, the valve preparation or disabling device 100 of FIGS. 1A-1C can be equipped with through-lumens in each of the jaws/arms 152 and 154 (which otherwise function the same as jaws 110, 112), depicted as valve preparation or disabling device 100 in FIG. 3. Two guide wires 156 and 158 are associated, respectfully, with the jaws 152 and 154. The two wires 156 and 158 operate as positioning rails on which the outer catheter 104 slides. The first arm 152 has a through lumen (not visible) from a proximal end (not shown) of the outer catheter 104 to a distal end of the first arm 152 that accepts the first guide wire 156. The second arm 154 is associated with a rapid exchange lumen that is mounted on the second arm 154 and extends along a portion of the second arm 154 and accepts the second guide wire 158. Alternately, the second arm 154 is associated with a through lumen as like the first arm 152. In one embodiment, to use the valve preparation or disabling device 100, the two guide wires 156 and 158 are slid through the opening O, one on either side of the opening O, with one ligation device C between the wires 156 and 158. The outer catheter 104 is then advanced over the first and second guide wires 156, 158 and guides the outer catheter 104 to the ligation device C. Once the respective valve preparation or disabling device 100 is in position, the method of disabling the ligating device C can continue as described herein.

Referring also back to FIGS. 21A-22F, which collectively illustrate the valve preparation or disabling device 500, which can be used for disabling a ligation device C. The valve preparation or disabling device 500 can be identical to that illustrated in FIGS. 1A-1C, except as explicitly stated. In this embodiment, the valve preparation or disabling device 500 includes the handle assembly 501, the inner catheter 502 and the outer catheter 504. The outer catheter 504 is coaxially aligned and arranged to slide over the inner catheter 502. At the distal end 506 of the inner catheter 502 is the first jaw 510 and the second jaw 512, wherein the jaws 510, 512 can pivot with respect to each another. In one embodiment, the jaws 510, 512 and inner catheter 502 are immovably affixed to each other proximate the handle assembly 501. In one embodiment, the jaws 510, 512 include mating features 511 (generally referenced), which may include grooves and teeth, which mate as the jaws 510, 512 open and close to assist in alignment of the jaws 510, 512 as they move. In some embodiments, the severing element 538 includes a first end 539a and a second end 539b (see, in particular FIGS. 22D-22F). In one implementation, the severing element 538 is spring biased to the position of FIG. 21 B (i.e. the first end 539a extending away from the second jaw 512 wherein the second end 539b is maintained within the jaw 512). In one embodiment, biasing function is provided by a spring portion 539c formed by the severing element 538. A pin 541 (shown in FIGS. 22D-22F) can be provided within the spring portion 539c to maintain and bias the severing element 538. The jaws 510, 512 can be delivered in a delivery arrangement (FIG. 21D), in which the jaws 510, 512 are substantially parallel each other and at least 90% of a length of the jaws 510, 512 are sheathed by the outer catheter 504. In the delivery arrangement, compressive pressure is applied from the outer catheter 504 to compress the jaws 510, 512 toward each other and into a cylindrical arrangement. In one implementation, the handle assembly 501 includes an actuator knob 505/actuator 562. The handle assembly 501 is configured such that rotational movement of the actuator 562 translates into movement of the actuator 562, which moves the outer catheter 504 to/away from the handle assembly 501 to sheath and unsheathe the jaws 510, 512 (FIG. 21D). The handle assembly 501 is provided as one example of a suitable handle assembly and it is envisioned that many other handle assembly designs can be configured to operate the device 500 in the manner described.

In one implementation, the handle assembly 501 includes a body 560 supporting an actuation knob 505. As indicated above, rotational movement of the actuation knob 505 translates to the actuator positioned within the body 560, which correspondingly moves the outer catheter 504 to and away from the body 560. In on example, the handle assembly 501 includes an aperture 564 for hemostatis valves (e.g., a three-way hemostasis valve, not shown) for the optional two guide wires 156, 158 and a conducting wire 568 interconnected to the electrode 538. It is noted that, in some embodiments, a channel 513 (FIG. 21B) is provided in the jaw 512 supporting the electrode 538 and that the conducting wire 568 can be routed through this channel 513 and soldered to the second end 539b of the electrode 538 and potted with adhesive or the like. The conducting wire 568 is not shown in FIG. 21B, however, for ease of illustration.

In some embodiments, severing or cutting is achieved by generating a plasma on the electrode 538 via an external power supply (not shown). For a monopolar design, an external counter electrode 539 (schematically shown) is mounted on the skin via a patch. For a bipolar design, the counter electrode 539 is mounted on the valve preparation or disabling device. The first and second jaws 510, 512 can be made of a polymeric material or a mix of polymer and metal, for example. One objective may be to balance the materials of the jaws 510, 512 to have enough metal to be visible under fluoroscopy but not so much metal as to interfere with echogenicity of the disabling device. In some embodiments, the only portion of the jaws 510, 512 that capture leaflet L1, L2 are the distal portion containing the puncturing electrode 538, thus allowing the electrode 538 to cut the leaflet L1, L2 as it is pulled proximally relative to the leaflet L1, L2 (in other words the jaws/electrode 510, 512, 538 can only move relative to the leaflet L1, L2 if the disabling device C is not clamping the leaflet AL, PL at some location). In various methods, the jaws 510 and 512 of the valve preparation or disabling device 500 are associated with guide wires 156, 158 to aid in positioning in a manner like to that of valve preparation or disabling device 100 having guide wires 156, 158 and as also shown in FIGS. 22A-22C.

Additional methods of using the valve preparation or disabling device 500 to disable a ligating clip (referring in particular to FIGS. 31-33 and related disclosure) can include delivering the valve preparation or disabling device 500 in a closed arrangement in which the first and second jaws 510, 512 are drawn together to a mitral heart valve V having a plurality of leaflets L1, L2 via a trans-atrial or trans-septal approach. Proximal with respect to the leaflets L1, L2, the jaws 510, 512 are pivoted away from each other to be splayed open. One jaw 510, 512 is slid through the opening O, one on either side of the opening O, with one ligating device C between the jaws 510, 512. In this way, the first jaw 510 and the second jaw 512 are positioned on opposing sides of the clip C. The jaws 510, 512 are then pivoted to the closed arrangement, the severing element 538 energized, and the entire device 500 is pulled distally to sever/cut through either the respective leaflet L1/AL/PL or the ligating device C, as applicable. In general this technique would be more effective for an Alfieri stitch as severing a suture ligation device is generally more amenable to this technique that severing/cutting of a metallic clip ligation device. The process can be repeated until all present ligating devices are sufficiently disabled or the leaflet is otherwise substantially severed or removed, as desired.

Figure 37:
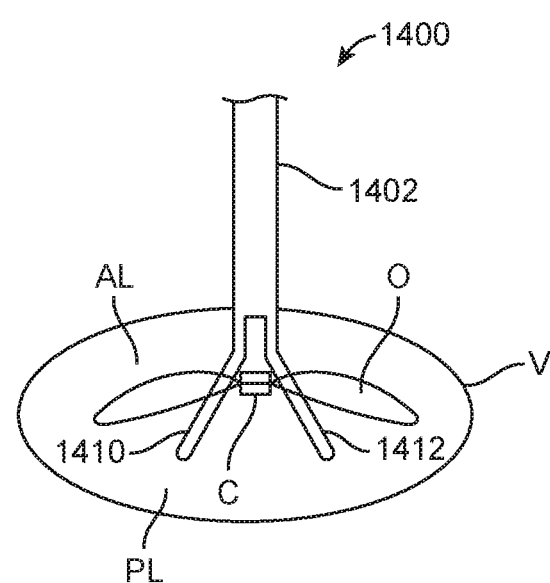
FIG. 37 is a partial, schematic illustration of an alternate disabling device having an inner catheter as well as first and second jaws, the disabling device in the process of removing a ligating device from the mitral valve of FIG. 31.
Figure 38:
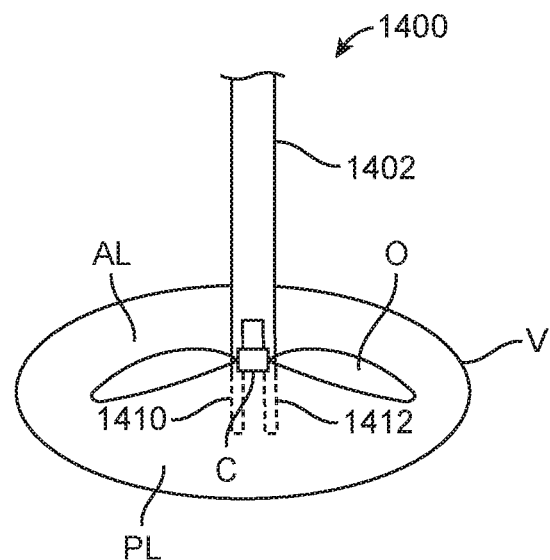
FIG. 38 is a schematic illustration of the disabling device of FIG. 37 having engaged the ligating device.
Figure 39:
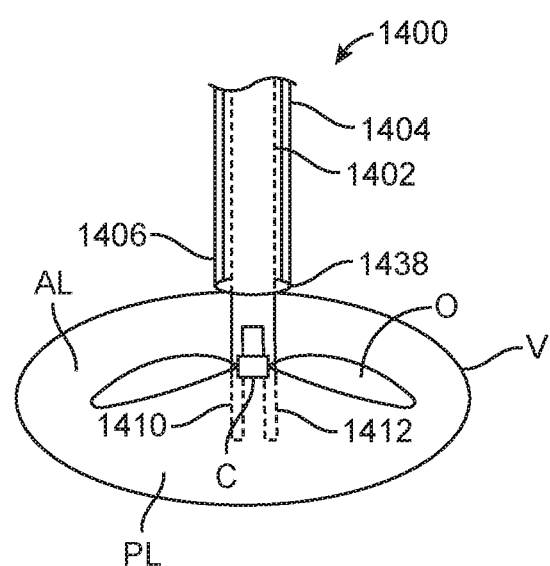
FIG. 39 is a schematic illustration of the disabling device of FIGS. 37-38 further including an outer catheter having a distal end with a severing element positioned over the inner catheter.

Referring now in addition to FIGS. 37-39, which illustrate yet another valve preparation or disabling device 1400 and method for disabling one or more ligating devices. The valve preparation or disabling device 1400 is substantially similar to that of FIGS. 1A-1B except as explicitly stated. Generally, the valve preparation or disabling device 1400 includes an inner catheter 1402 and an outer catheter 1404 coaxially aligned and slidably positioned over the inner catheter 1402. The inner catheter 1402 includes first and second jaws 1410, 1412, which can be identically configured to jaws 110, 112. The main difference in this embodiment is that the outer catheter 1404 has a distal end 1406 including a severing element 1438. The severing element 1438 can, for example, be a cork borer edge, radio frequency tipped or configured to generate a plasma. In this way, tissue to be severed can be grasped with the jaws 1410, 1412 to hold the tissue (e.g., leaflets AL, PL) in position while the outer catheter 1404 is distally advanced to bring the severing element 1438 into contact with the leaflets AL, PL. If applicable, the severing element 1438 is energized or otherwise actuated to sever the leaflets such that the outer catheter 1404 extend through the leaflets AL, PL. In one embodiment, the ligation device C is captured between the jaws 1410, 1412 prior to distally advancing the outer catheter to sever the leaflets AL, PL. In this way, the ligation device C can be removed from the patient via proximal retraction of the valve preparation or disabling device 1400 in the same manner in which the valve preparation or disabling device 1400 was delivered. Portions of the leaflets AL, PL captured within the jaws 1410, 1412 will thus also be removed. In effect, this method removes the ligation device C obstruction within the opening O so that a prosthetic heart valve can be implanted within the opening or alternate interventional procedure can be conducted.

Figure 40A:
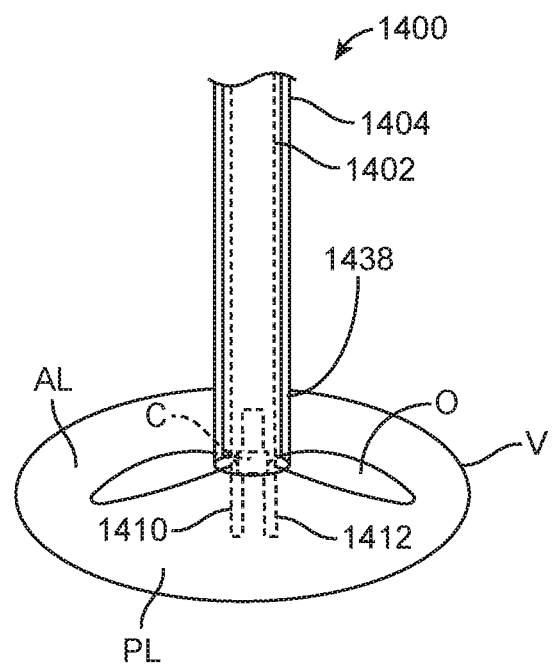
FIG. 40A is a schematic illustration of the severing element of the disabling device of FIGS. 37-39 advanced through both anterior and posterior leaflets of the mitral valve, forming a cut or the like surrounding 360 degrees around the ligating device so that the ligating device can be removed from the mitral valve.
Figure 40B:
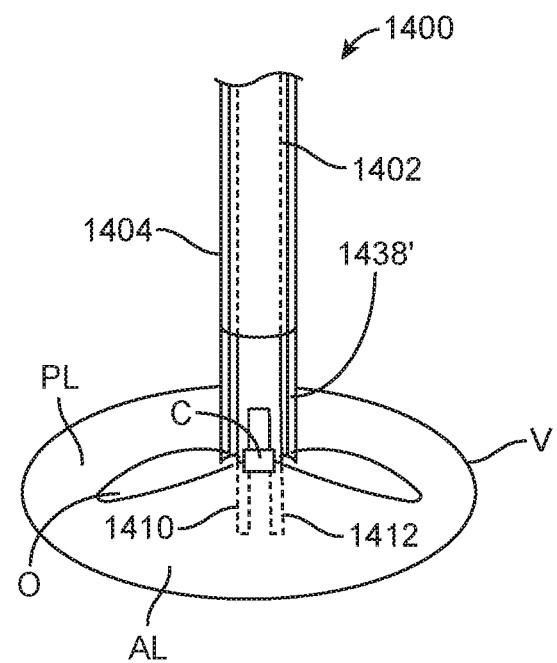
FIG. 40B is a schematic illustration of the severing element of the disabling device of FIGS. 37-39 advanced through one leaflet of the mitral valve, forming a cut or the like surrounding approximately 180 degrees around the ligating device so that the ligating device is disabled.

In the embodiment of FIG. 40A, the severing element 1438 is configured to sever approximate 360 degrees of leaflets AL, PL around the ligation device C so that the ligation device C can be removed from the patient (see, e.g., area A' of FIG. 33). In the embodiment, of FIG. 40B, however, a severing element 1438' can be configured to sever less than 360 degrees, approximately 180 degrees of leaflet AL, PL around the ligation device C (see, e.g., area A of FIG. 32) so that the clip C is merely disabled so that the opening O is unobstructed and left within the patient. It is noted that a distal portion of the outer catheter 1404 is omitted in the view of FIG. 40B for clarity. After the leaflet(s) AL, PL are severed as shown in FIG. 40B, the jaws 1410, 1412 can transition to the open arrangement to release the leaflets AL, PL and/or ligation device C. The valve preparation or disabling device 1400 is then proximally retracted in the same manner in which it was delivered.

In yet another embodiment, the jaws 1410 and 1412 of the valve preparation or disabling device 1400 are associated with guide wires to aid in positioning in a manner like to that of valve preparation or disabling device 100 having guide wires 156, 158.

Figure 41:
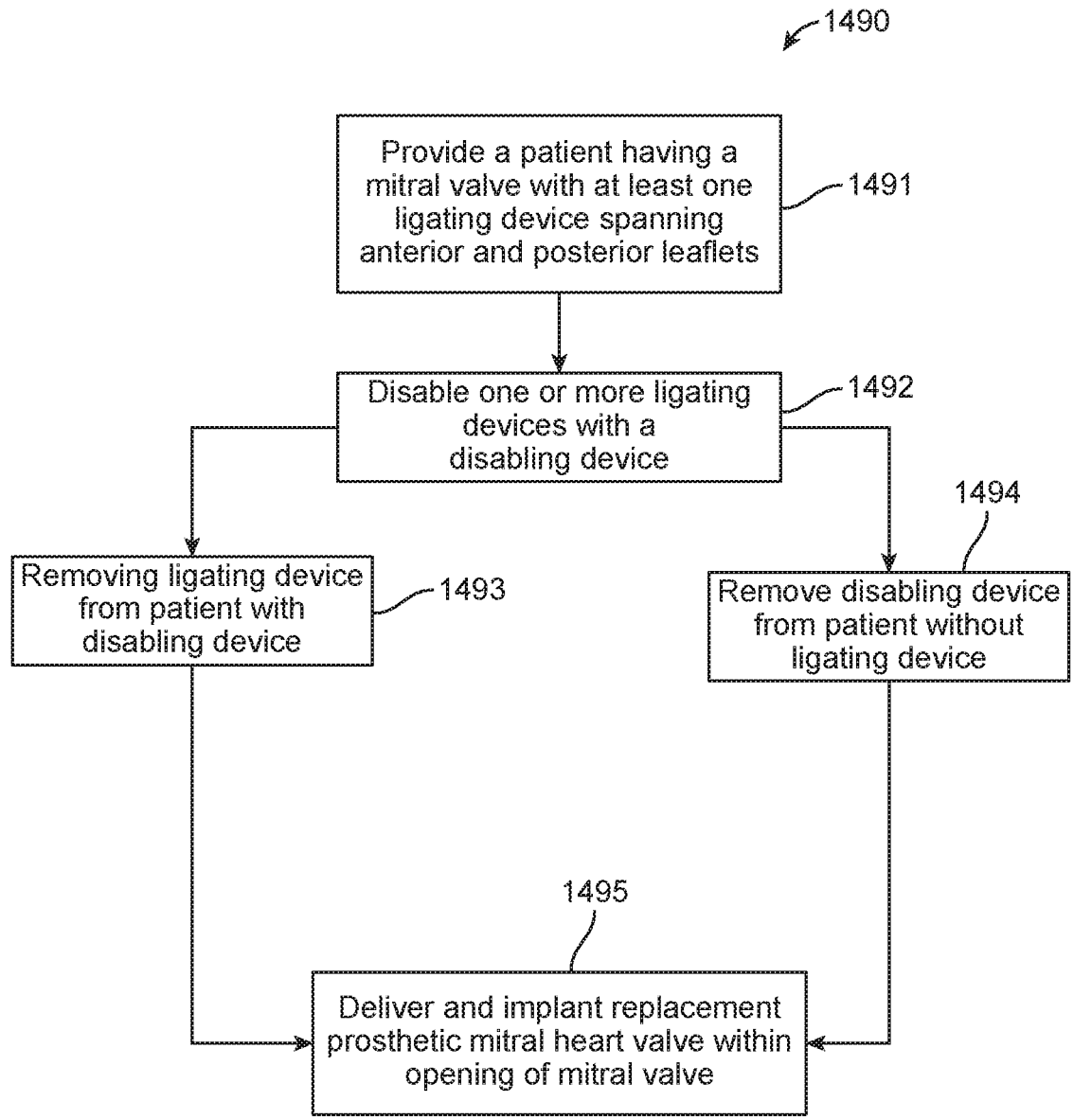
FIG. 41 is a flow chart illustrating various methods of the disclosure.
Figure 44:
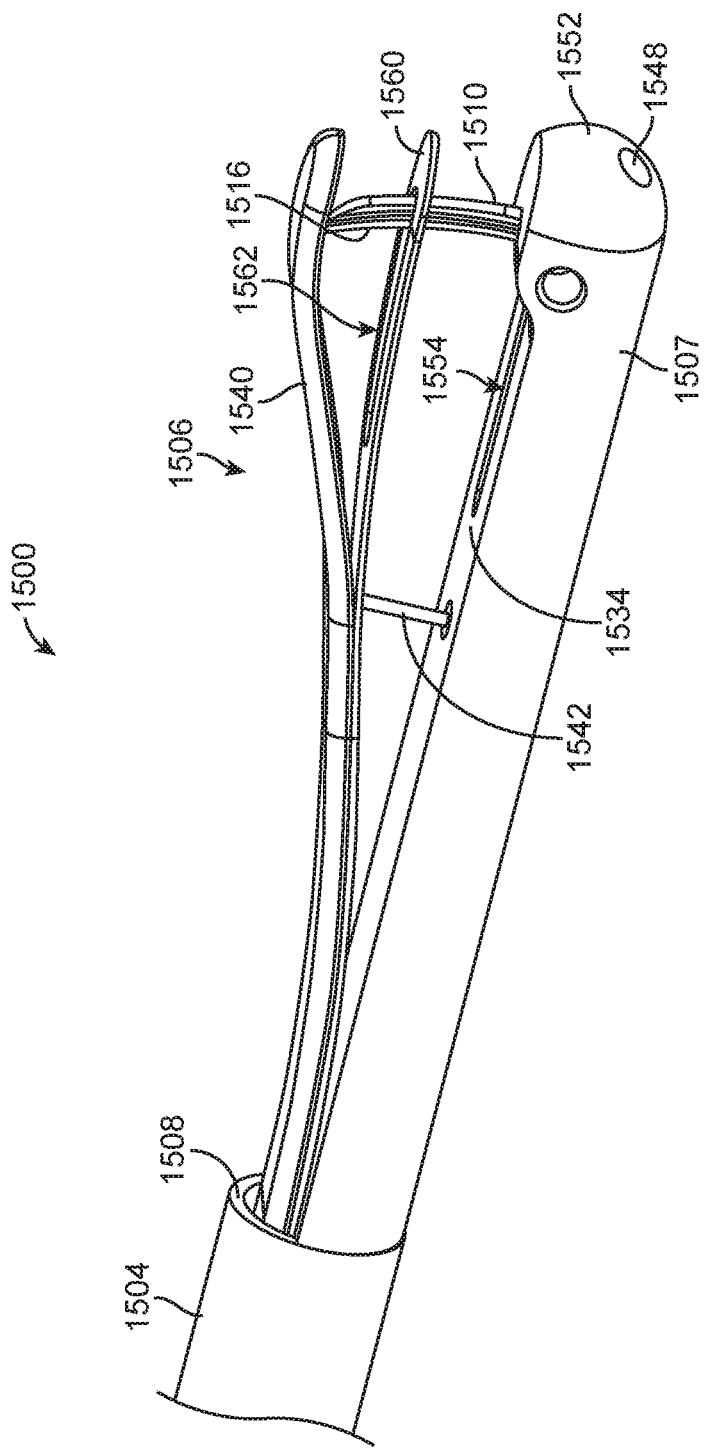
FIG. 44 is a perspective view of the jaws of the device of FIG. 42.

Many of the aforementioned methods of the disclosure are outlined in the flow chart of FIG. 41. As generally indicated in FIG. 41, in an any of the methods of the disclosure, the methods can further include implanting a prosthetic heart valve (e.g., an aortic heart valve) within the opening after all applicable ligation devices are disabled and the valve opening is unobstructed (i.e. in which either one or more previously implanted ligation devices is removed from the patient, one of the leaflets have been severed, or one or more ligation devices have been disabled such that the prosthetic mitral heart valve is implanted. In some methods, the prosthetic mitral heart valve is implanted adjacent the previously disabled ligation device(s). The prosthetic mitral heart valve can be of any of the type known in the art for replacing a mitral valve and methods of delivery and implantation of the stented prosthetic heart valve can be of any of those known in the art with respect to replacing a mitral valve.

In particular, a method 1490 of the disclosure can include providing a patient having mitral valve with at least one ligating device spanning anterior and posterior leaflets 1491. Then, the method includes disabling one or more ligating devices with a disabling device of the disclosure 1492. Optionally, the disabling device can be removed with the ligating device 1493 or the disabling device can be removed from the patient without the ligating device 1494. Then, once the disabling device is removed, the method can include delivering an implanting a replacement prosthetic mitral heart valve within an opening of the mitral valve 1495.

Referring now in addition to in FIGS. 42-56, which collectively disclose yet another valve preparation or disabling device 1500 that can be used in the aforementioned procedures. The device 1500 includes handle assembly 1502, catheter tube 1504 and a tip assembly 1506 extending from a proximal end 1508 of the catheter tube 1504. The tip assembly 1506 includes a tip body 1507, which can otherwise be referred to as a jaw, which supports a severing element 1510. In some embodiments, the severing element 1510 can function as blade. In other implementations, the severing element 1510 can function as an electrode. In some implementations, the severing element 1510 functions as both a blade and as an electrode. In instances where the severing element 1510 can function as an electrode, the handle assembly 1502 is configured for connection to a source of radio-frequency (RF) energy 1512, which can be applied via the severing element 1510 to sever leaflet tissue, for example. The handle assembly 1502 illustrated is just one example of a suitable handle assembly. It is envisioned that other handle assemblies may be provided that accomplish similar functions to operate the tip assembly 1506.

In one example, the severing element 1510 includes a body 1514 having a sharpened cutting edge 1516 terminating at a tip 1511 that can be used to pierce and then lacerate a leaflet. In one embodiment, the cutting edge 1516 is configured to be sharp with all other edges of the body 1514 being rounded. The severing element 1510 further includes a solder tab 1518 to attach a wire 1520 to both conduct energy to the severing element 1510 from the RF source 1512 and also to push and pull to pivot the severing element 1510 from a folded position to an unfolded position. In embodiments where the severing element 1510 does not function as an electrode, the wire 1520 need not be conductive or be connected to a RF source. The wire 1520 interconnects the severing element 1510 to a respective actuator 1522 of the handle assembly 1502 for control by a user. In one embodiment, the severing element 1510 further includes an aperture 1524 to accept a pin 1526 (omitted in some views for ease of illustration) about which the severing element 1510 can pivot. In one example, the element body 1514 is made of stainless steel and the body 1514 is partially coated with an insulating material 1528 such as ceramic, glass, polytetrafluoroethylene or the like. At least a portion of the solder tab 1518 is not coated with the insulating material to allow a conductive location to connect with the wire 1520, in cases where the severing element 1510 can function as an electrode. The wire 1520 connected to the severing element 1510 has a stranded conductor portion 1530, and is stripped long, so that it is flexible. With a length of shrink tubing 1532 or other insulating material covering the conductor portion 1530, a push and pull action to the wire 1520, as enabled via an actuator 1522 of the handle assembly 1502, pivots the severing element 1510 to and from the folded and unfolded positions. Generally, insulating the wire 1520 and severing element 1510 can be important when use of the device 1500 is performed in a conductive environment (e.g., amongst blood) and, therefore, if applicable, the electrical path of the device 1500 from the RF source 1512 to the severing element 1510 can be sealed and kept from dispersing energy into the fluid to focus the RF energy at the cutting edge 1516 so that its effectiveness is not reduced.

The severing element 1510 is configured to rotate toward and away from an upper surface 1534 of the tip body 1507 as schematically depicted in FIGS. 46-49. In the folded position the tip assembly 1506 can be introduced to a heart through the femoral approach. Once the severing element 1510 is in the heart and through the aortic valve the severing element 1510 is moved to the unfolded position in preparation to cut a leaflet as will be discussed in further detail below.

Figure 45:
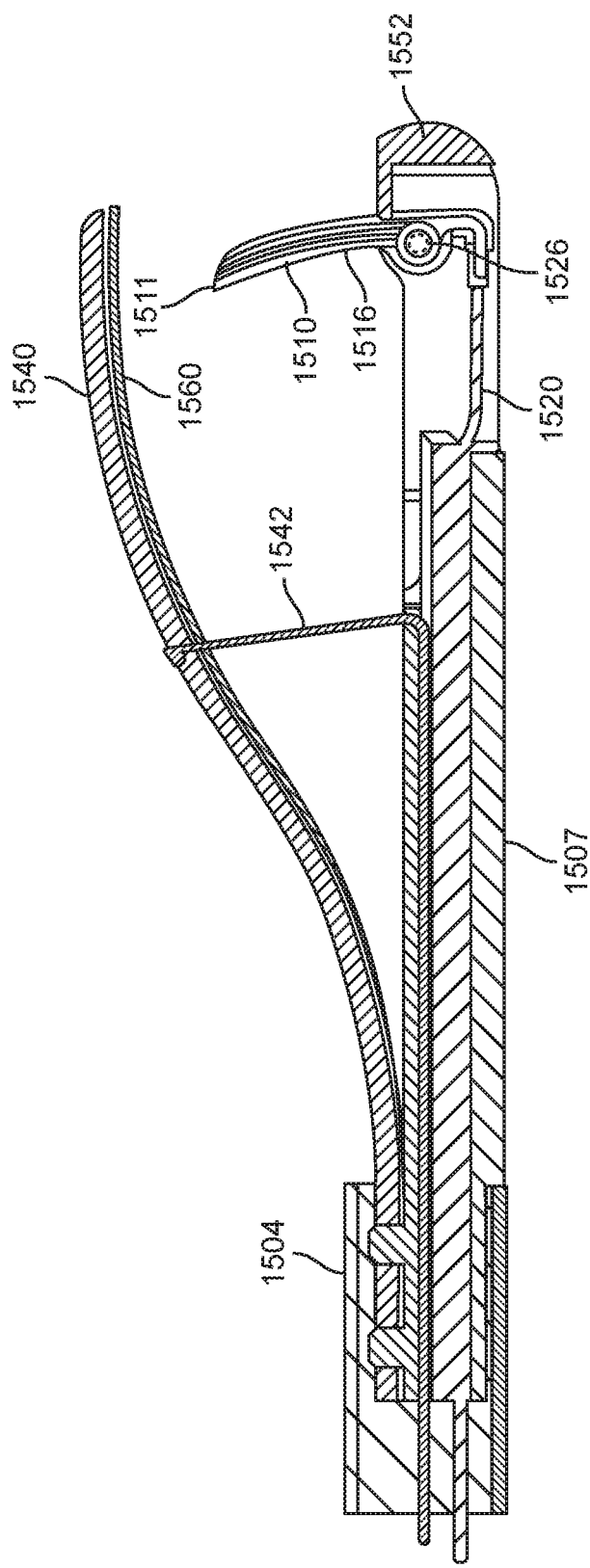
FIG. 45 is a cross-sectional view of FIG. 44.
Figure 46:
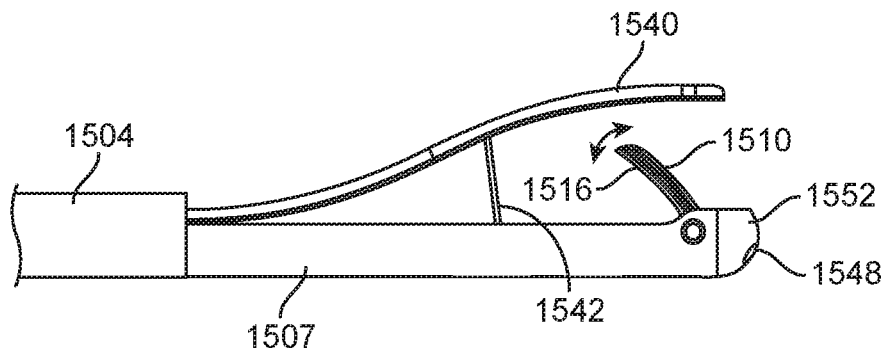
FIG. 46 is a partial, side view of the device of FIG. 42 illustrating the jaws in an open arrangement.
Figure 47:
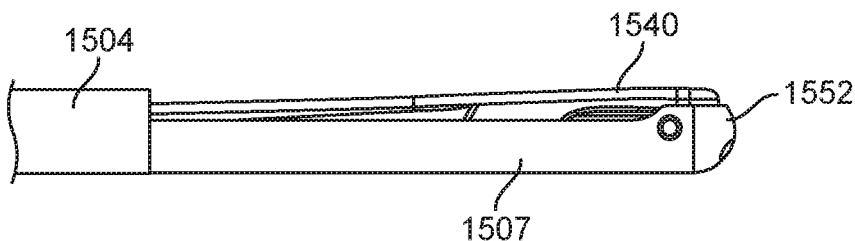
FIG. 47 is a partial, side view of the device of FIG. 46 illustrating the jaws in a closed arrangement.
Figure 48:
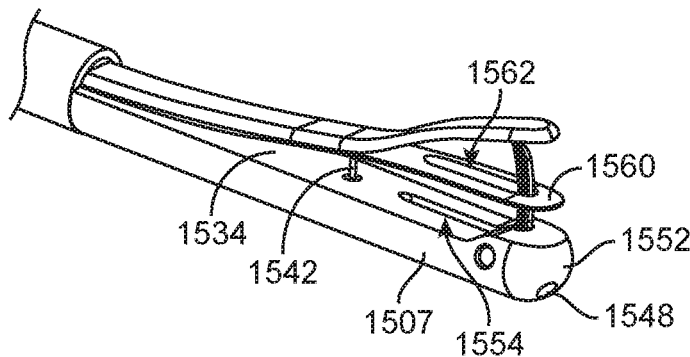
FIG. 48 is a perspective view of the device of FIG. 46 with the jaws in the open arrangement.
Figure 49:
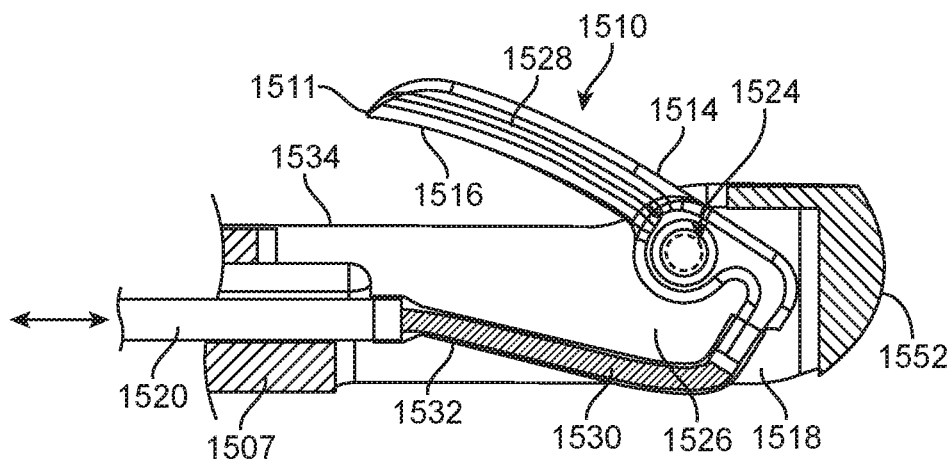
FIG. 49 is a cross-sectional view of one jaw of the device of FIG. 46.

In one example of the device 1500, the upper surface 1534 of the tip body 1507 is planar to receive a first or outer arm 1540 is positioned. The first, outer arm 1540 can otherwise be referred to as a jaw. The outer arm 1540 is configured to pivot with respect to the upper surface 1534 and can optionally be made of a non-conductive material so that energy from the severing element 1510, if applicable, cannot pass through the outer arm 1540. Movement of the outer arm 1540 is controlled with a wire 1542 or the like extending from the outer arm 1540 to the handle assembly 1502, which is configured to push and pull the wire 1542, via a respective actuator 1544, to correspondingly control movement of the outer arm 1540. When the wire 1542 is pushed in a direction of the tip assembly 1506 via the actuator 1544, the outer arm 1540 transitions to a biased open position as shown in FIG. 45, for example. In some embodiments, the outer arm 1540 is biased to the open position via molding the outer arm into a generally S-shaped configuration, as shown in FIGS. 45-46. When the wire 1542 is pulled in a direction away from the tip assembly 1506 with the actuator 1544, the outer arm 1540 is pulled toward the upper surface 1534 of the tip body 1507 into a closed position in which the outer arm 1540 generally flattens out into a linear arrangement. In the closed position, the outer arm 1540 can be configured such that the tip assembly 1506 has a generally uniform diameter along its length, which reduces the profile of the tip assembly 1506 for delivery. A guide wire channel 1548 can extend from the handle assembly 1502, through the catheter tube 1504 and through the tip body 1507. The tip body 1507 can include a rounded distal cap 1552 at its distal-most end, proximate the severing element 1510. In one implementation, the tip body 1507 includes a longitudinal slot 1554 in the upper surface 1534 through which the severing element 1510 can be positioned in the folded position. The entirety of the severing element 1510 may fit in the slot 1554 to provide a more compact tip assembly 1506 for delivery.

In some embodiments, the tip assembly 1506 further includes a second or inner arm 1560 positioned between the outer arm 1540 and the tip body 1507 that is biased away from the upper surface 1534 in an S-shaped configuration in a manner and orientation similar to that of the outer arm 1540. The inner arm 1560 can include a slot 1562 through which the severing element 1510 can pass when the severing element 1510 is in the unfolded position. In some embodiments, the inner arm 1560 is made of metal or alternative radiopaque material. Once the severing element 1510 is in the desired position, confirmed via fluoroscopy, the severing element 1510 can then activated and due in part to the pressure of the spring-loaded or biased outer arm 1540, the severing element 1510 pierces the leaflet by pushing the leaflet over the tip 1511, which may or may not be assisted via RF energy applied at the tip 1511. In one implementation, the wire 1542 is connected to the inner arm 1560 and outer arm 1540 so that they can be moved together with one actuator 1544. When the wire 1542 is pulled, both the outer and inner arms 1540, 1560 collapse to the tip body 1507 and when the wire 1542 is pushed, both of the outer and inner arms 1540, 1560 pivot out from the tip body 1507 into their natural, biased positions.

The device 1500 can be used in one of the disclosed methods for severing a leaflet and/or severing one or more ligation devices or the like that are interconnecting two leaflets. The device 1500 is advantageous as it configured to allow a user to first confirm the leaflet has been grasped, and second that the leaflet has been pierced by the electrode prior to forming a slit in the leaflet. In particular, the device 1500 can be configured such that a user will see positions of certain radiopaque elements of the device (such as the radiopaque severing element 1510, radiopaque inner arm 1560) under fluoroscopy and be able to make these confirmations, for example.

Figure 50:
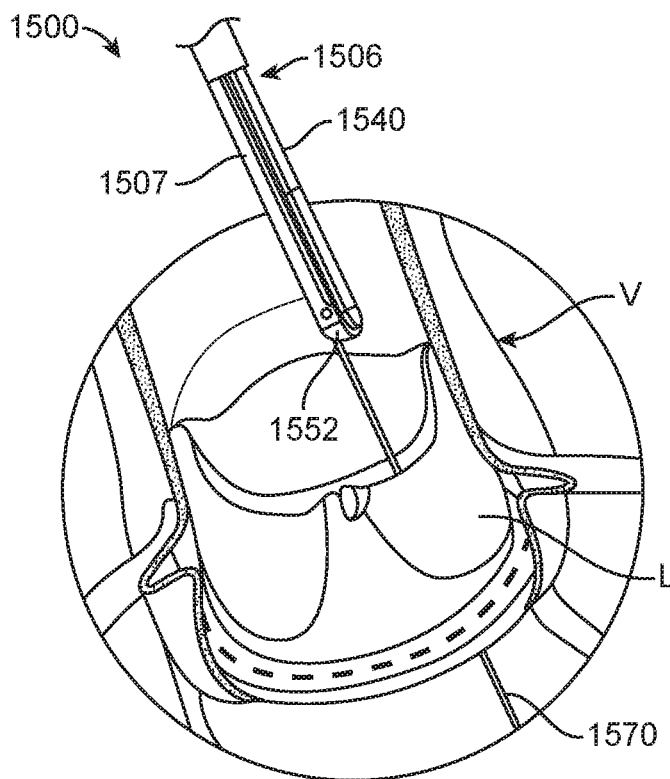
FIGS. 50-56 illustrate one example method of using the device of FIGS. 42-49.

One example method of using the device 1500 is illustrated in FIGS. 50-56. In FIG. 50, the device 1500 is introduced in the delivery configuration to a valve V of a human heart through a femoral approach through a steerable catheter. The device 1500 is positioned above the trans-aortic valve. A guide wire 1570 is pushed through the guide wire channel 1548 and through the trans-aortic valve.

Figure 51:
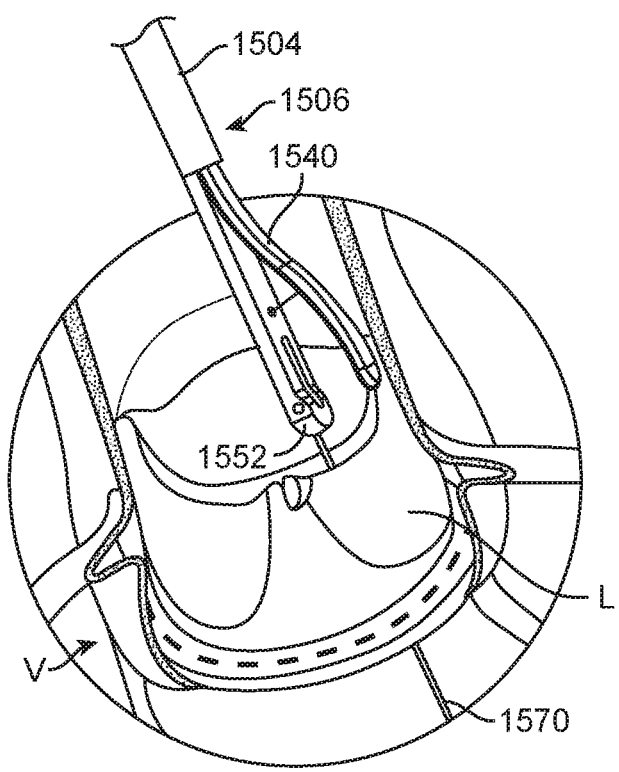
Figure 52:
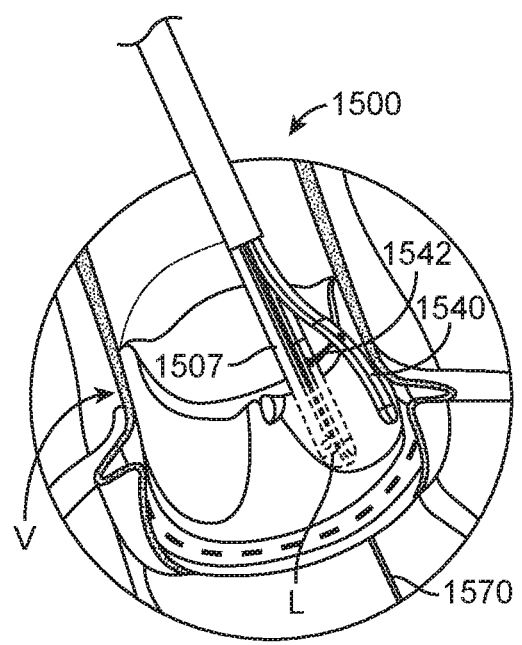
Figure 53:
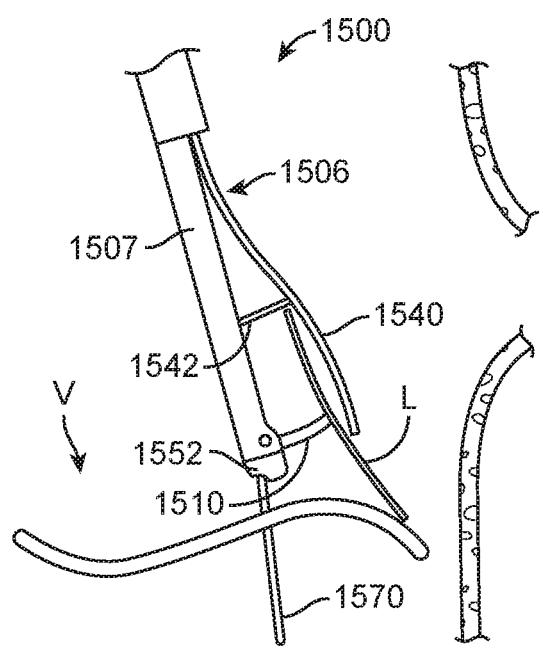

Then, as shown in FIG. 51, the outer and inner arms 1540, 1560 of the device 1500 are pushed away and freed to transform to their biased positions by pushing the wire 1542 in the direction of the tip assembly 1506 via the respective actuator 1544. Due to the radio opaque properties of the both the severing element 1510 and the inner arm 1560, the tip assembly 1506 can be rotated and aligned into the desired position using fluoroscopy. The tip assembly 1506 is then pushed into an opening of the trans-aortic valve using the guide wire 1570 as shown in FIGS. 52-53.

The severing element 1510 is moved from the folded position to the unfolded position via the respective actuator 1522. Using fluoroscopy, the severing element 1510 is positioned on the inside of the leaflet L where the incision is desired (FIGS. 52-53). The outer and inner arms 1540, 1560 remain on the outside of the leaflet L.

The outer and inner arms 1540, 1560 are pulled toward the severing element 1510, to provide pressure from the severing element 1510 onto the leaflet L. The inner arm 1560 is still located proximate the tip 1511, contacting the leaflet at the tip 1511.

Figure 54:
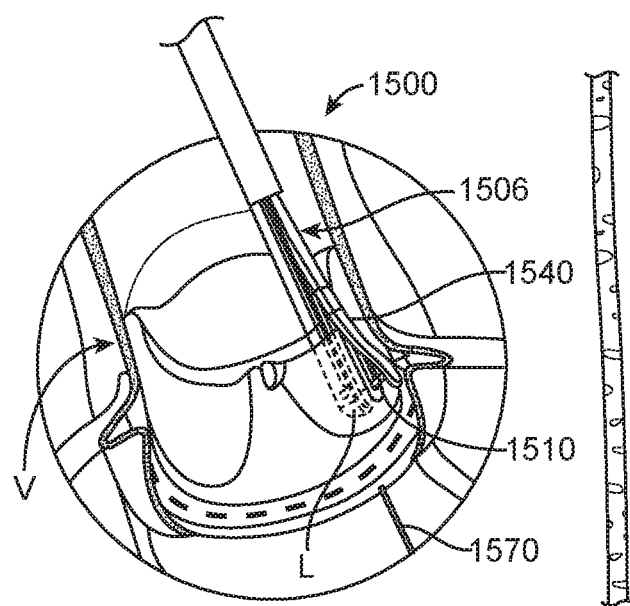
Figure 55:
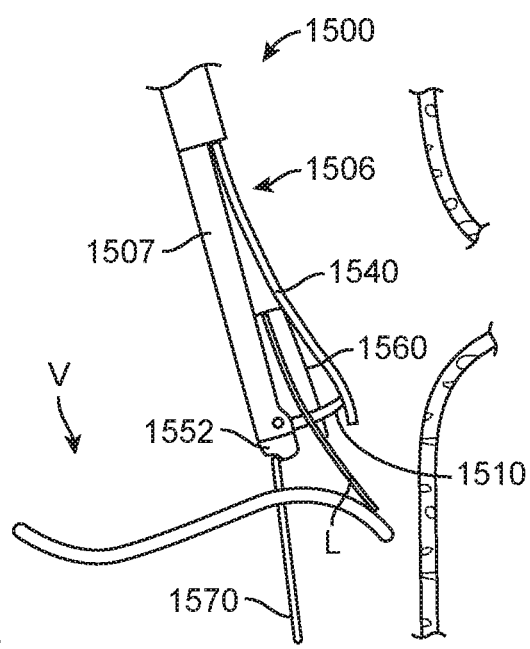

Once the severing element 1510 position is confirmed, the severing element 1510 is activated. Because the inner arm 1560 includes the slot 1562 and is biased away from the upper surface 1534, the inner arm 1560 slides over the severing element 1510 when the leaflet L is pierced (FIGS. 54-55). Using fluoroscopy, the piercing of the leaflet L is confirmed by viewing the positions of the severing element 1510 with respect to the inner arm 1560. It is noted that, during this step, the outer arm 1540 is positioned to cover the tip 1511, and protect any surrounding tissue (e.g., aortic wall) from being inadvertently treated.

Figure 56:
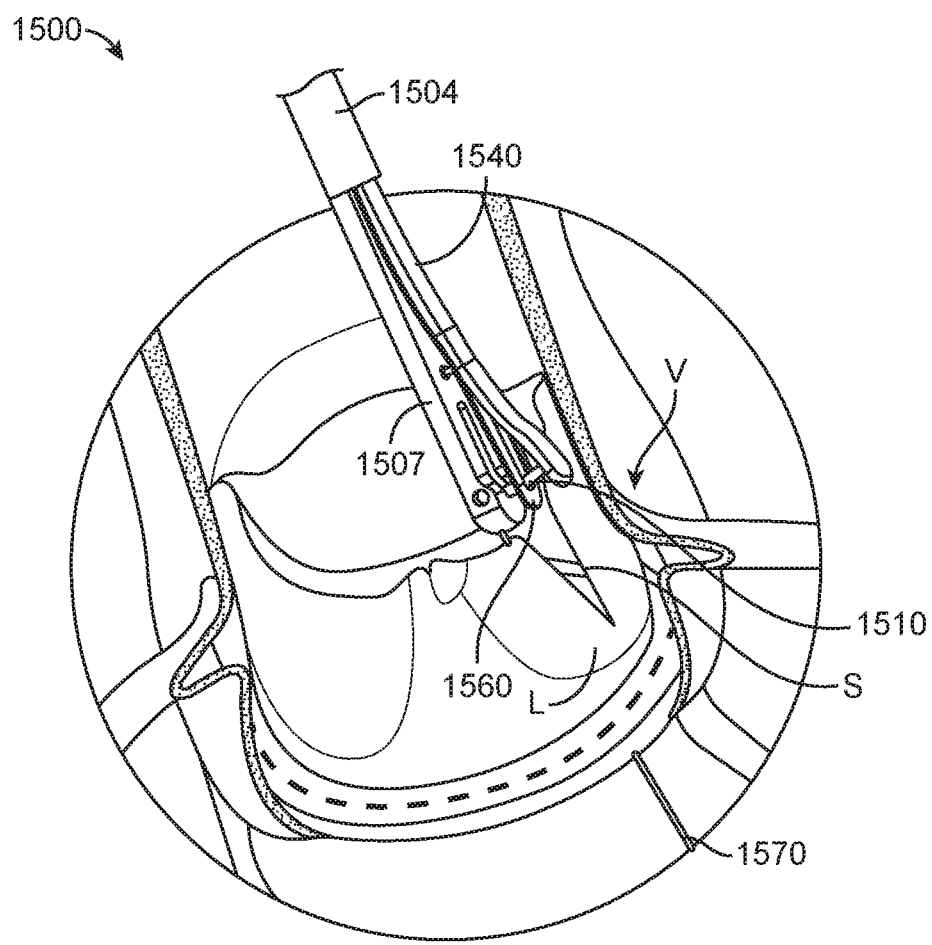

As generally depicted in FIG. 56, the severing element 1510 is activated again and the device 1500 retracted to form a slit S in the leaflet L generally corresponding with a distance the tip assembly 1506 is retracted or until the device 1500 is freed from the leaflet L. If there is potential blockage of the other coronary artery, the process can optionally be repeated on the corresponding leaflet. In other examples of the disclosure, it will be understood that the device 1500 can be used in a method similar to that of FIG. 41.

Figure 57:
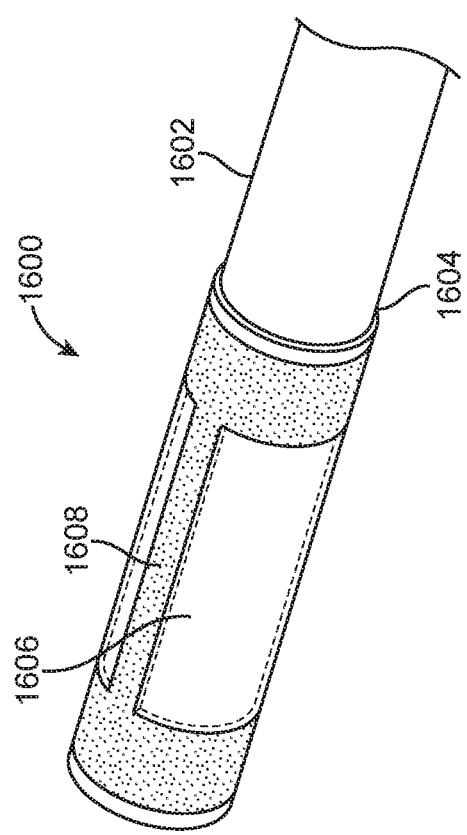
FIG. 57 is a partial, perspective view of an alternate device.
Figure 59:
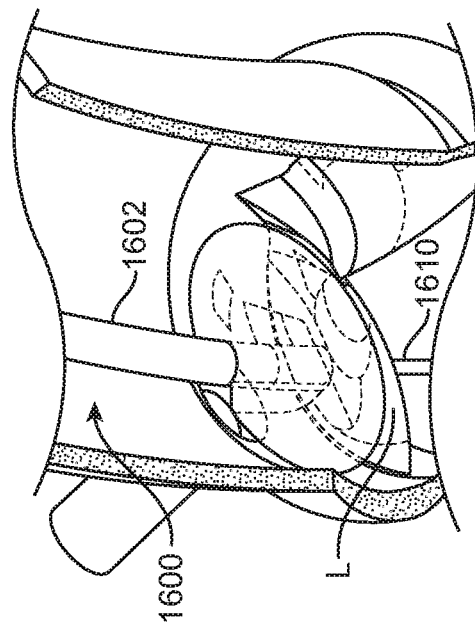
FIGS. 58-59 illustrate one example method of using the device of FIG. 57.
Figure 58:
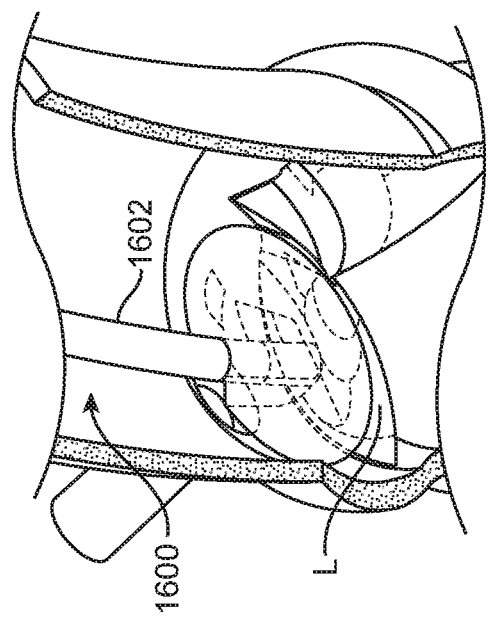

Referring now in addition to FIGS. 57-59, which illustrate another positioning device 1600 of the disclosure for use in the aforementioned procedures and devices similar to the grasper 150 of FIGS. 3-4. In other words, the device 1600 can be used as a replacement for grasper 150, whenever desired, or can otherwise be omitted from any of the aforementioned methods of use of the devices of the disclosure. In one example, the positioning device 1600 can be used for locating a puncturing wire, electrode, blade or the like, in front of a coronary ostium.

In one example, the positioning device 1600 includes a positioning catheter 1602. At a distal tip 1604 of the catheter 1602, a positioning balloon 1606 is positioned. The positioning balloon 1606 is made of a compliant material that can be delivered in a deflated arrangement and can be inflated, via an inflation pathway provided within the catheter 1602, which is interconnected to an inflation source (not shown) to expand a diameter of the positioning balloon 1606. In one example, the balloon includes a portion (e.g., line) of adhesive 1608 or the like extending axially along one side of the positioning balloon 1606 along a length of the positioning balloon 1606. The portion of adhesive 1608 prevents the area proximate the portion of adhesive 1608 from expanding during inflation, thus resulting in a balloon having an irregular, kidney shape in its inflated state. The kidney shaped, inflated positioning balloon 1606 is advanced to a cusp of the leaflet L that is to be cut or severed. Steering of the catheter 1602 may be required to get the distal end 1604 of the catheter 1602 near the desired location. The positioning balloon 1606, in some embodiments, can be provided with radiopaque markers (not shown) to help the rotational orientation alignment. When inflated, the positioning balloon 1606 acts to center the catheter 1602 in the respective cusp of the leaflet L. Additionally, the kidney shape of the inflated positioning balloon 1606 provides an opening to the coronary to ensure proper blood flow to the heart. Once a clinician is satisfied with the position of the distal end 1604 of the catheter 1602, a little forward pressure on the catheter 1602 and a wire 1610 can be inserted through the catheter 1602 and used to puncture the leaflet L (FIG. 59). In one example, the wire is RF powered wire. In other embodiments, the wire can be sharpened so that it is suitable for puncturing the leaflet. Once a hole or puncture in the leaflet L is formed, any guide-wire can be tracked from the catheter 1602 and through the leaflet L for use to guide any valve preparation or disabling device of the disclosure to its location.

Figure 60:
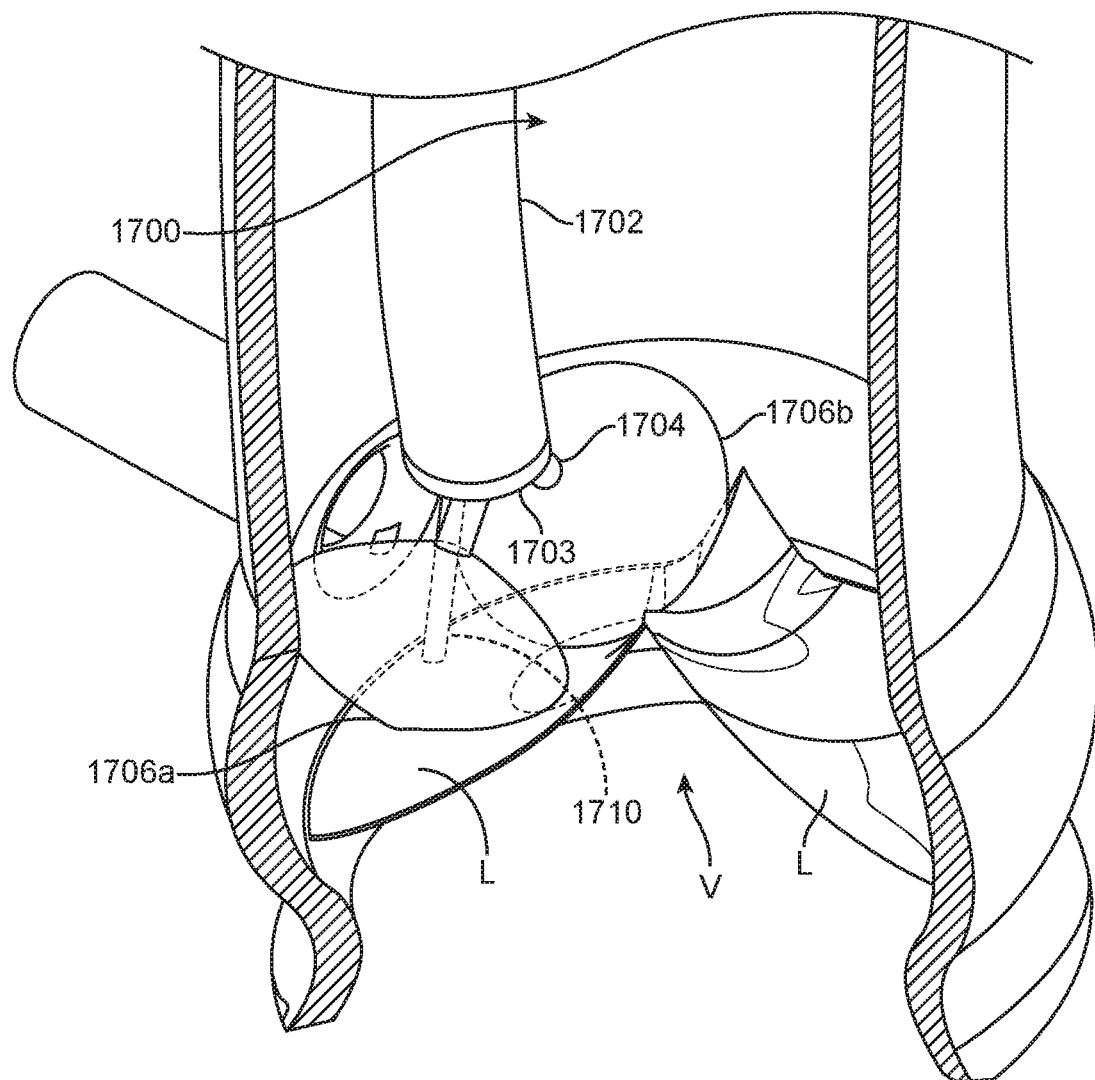
FIG. 60 is a partial, perspective view of a positioning device.

Referring now in addition to FIG. 60, which illustrate a positioning device 1700 that is largely similar in configuration and use as compared to that of FIGS. 57-59 except as explicitly stated. The positioning device 1700 includes a positioning catheter 1702 having a distal end 1704. In this embodiment, the positioning device 1700 includes first and second positioning balloons 1706a, 1706b, positioned adjacent each other. Each positioning balloon 1706a, 1706b can be similarly configured and operate as compared to positioning balloon 1606 described above. In one example, the positioning balloons 1706a, 1706b are located 180 degrees from each other. In one example, the catheter 1702 includes a semi-rigid extension tube 1703 extending from the distal end 1704 guide a wire 1710, which is the equivalent of wire 1610 described above.

Figure 61:
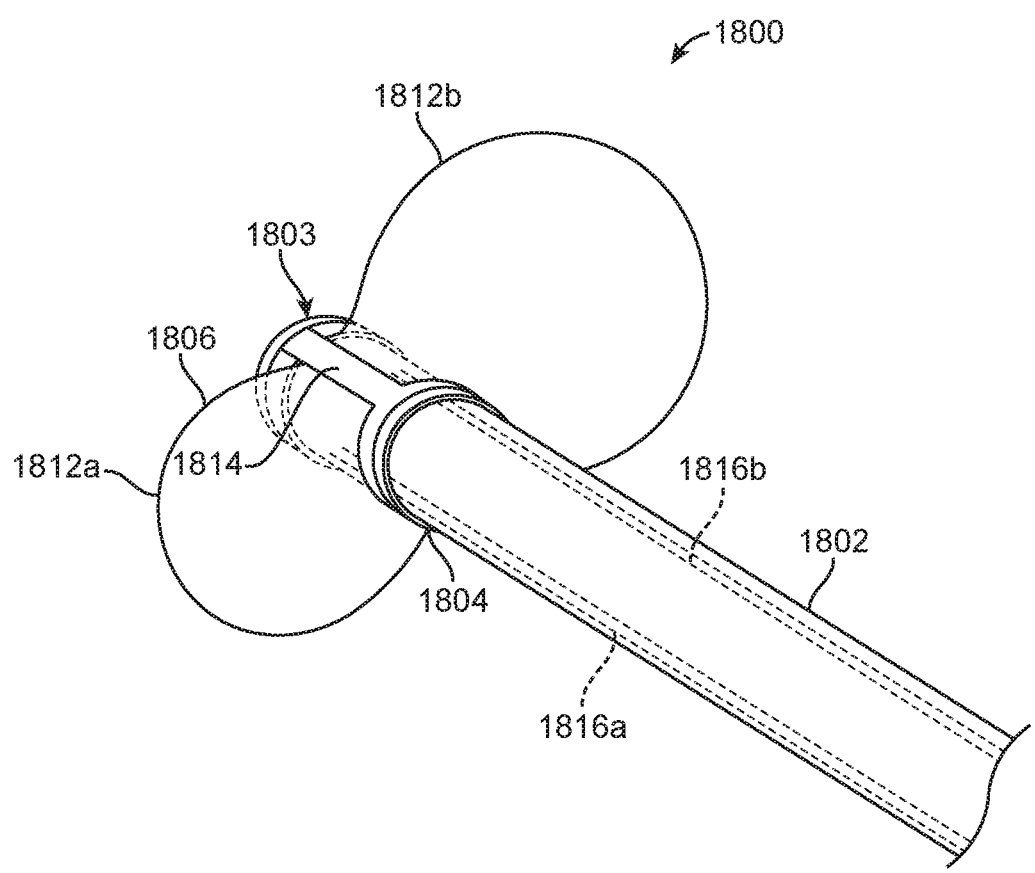
FIG. 61 is a partial, perspective view of an alternate positioning device.

Referring now in addition to FIG. 61, which illustrate a positioning device 1800 that is largely similar in configuration and use as compared to that of FIGS. 57-60 except as explicitly stated. The positioning device 1800 includes a positioning catheter 1802 having a distal end 1804. At the distal end 1804, a frame 1803 supports a positioning balloon 1806 defining two segments 1812a, 1812b separated by a strip of adhesive 1814 at opposite quadrants at the distal end 1804 of the catheter 1802, which would operate in a similar way to the embodiment of FIG. 60. In one example, the catheter 1802 provides separated first and second lumens 1816a, 1816b in order to deliver saline or another inflation medium to the balloon segments 1812a, 1812b separately. One advantage of the segmented balloon configuration is that a clinician can align a puncture point with the coronary even if the coronary is not centered with a belly of the respective leaflet.

Figure 62:
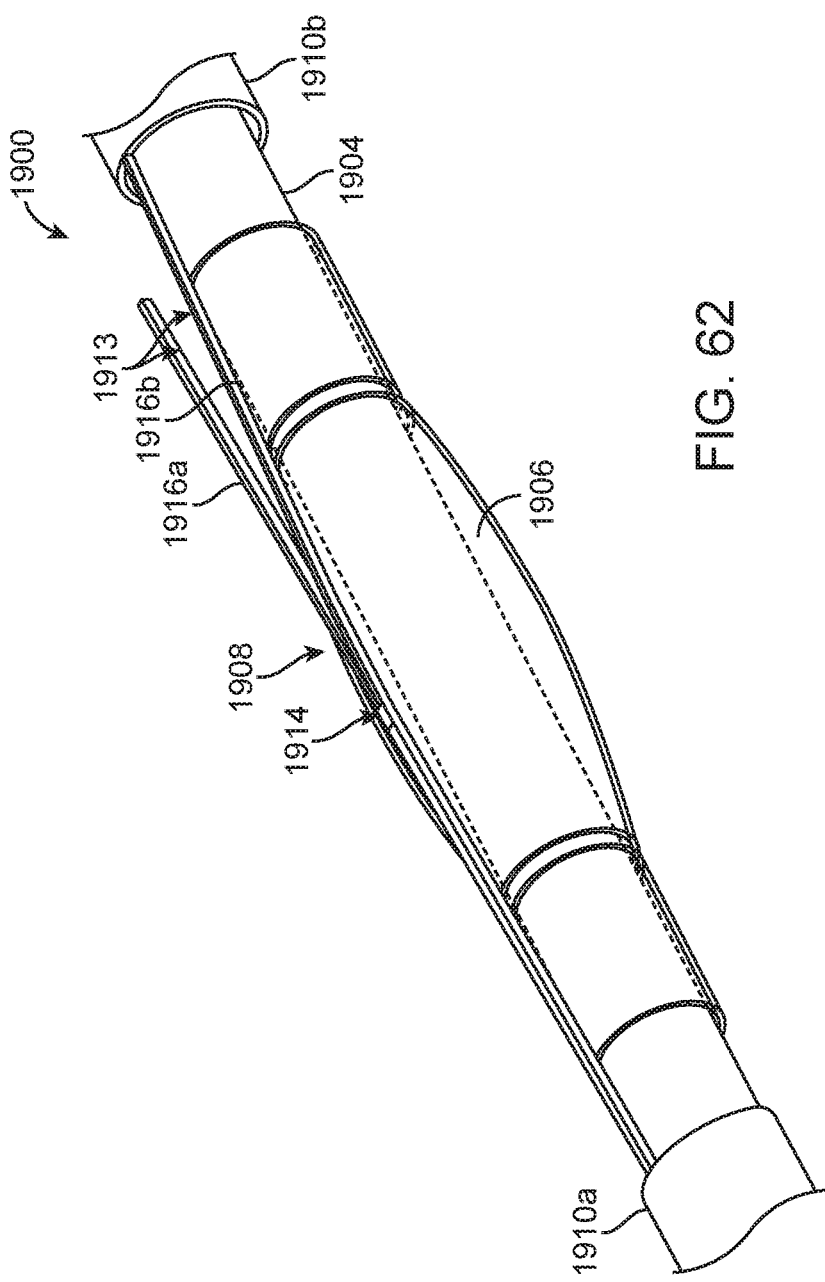
FIG. 62 is a partial, perspective view of an alternate device including a balloon and an electrode.
Figure 63:
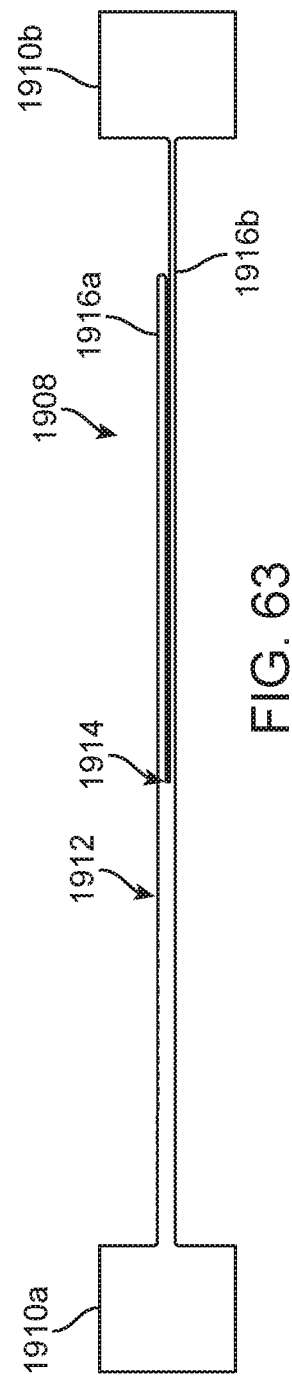
FIG. 63 is a schematic representation of the electrode of FIG. 62.

Referring now in addition to FIGS. 62-67, which collectively illustrate a valve preparation or disabling device 1900 that can be used in the aforementioned procedures. The device 1900 includes an outer catheter 1902 (FIG. 64) having an inner catheter 1904 slidably disposed therein. The inner catheter 1904 supports a balloon 1906 made of a compliant material. A severing element 1908 is positioned over, but may not directly be connected to the balloon 1906. In one implementation, the severing element 1908 is an electrode. The severing element 1908 has a delivery configuration (FIG. 66) in which the severing element 1908 is collapsed against the balloon 1906 and generally parallel to the inner catheter 1904 and the severing element also has a deployed configuration (FIG. 67), which is activated by inflation of the balloon 1906. In the deployed configuration, the severing element 1908 at least partially extends away from (i.e. protrudes from) the balloon 1906 and extends at an angle with respect to the inner catheter 1904. In one embodiment, the severing element 1908 includes a distal ring 1910a and a proximal ring 1910b interconnected by a body 1912. the body 1912 includes a split junction 1914 defining first and second portions 1916a, 1916b, the first portion 1916a being the portion of the severing element 1908 that extends outwardly from the balloon 1906 in the deployed position. The proximal ring 1910b is immovably fixed to the inner catheter 1904 and the distal ring 1910a can be slidably connected to the inner catheter 1904 to account for the shortening of the severing element 1908 when in the deployed position. In one embodiment, the severing element 1908 is made of an elastic material so that the distal ring 1910a can be immovably fixed to the inner catheter. In instances where the severing element 1908 is an electrode, the electrode can be at least partially coated with a non-conductive material to limit the area of the electrode that can be activated. In one example, all surfaces of the severing element 1908 are coated with an insulating material except for those designed at 1913. These surfaces 1913 are those that both touch in the delivery configuration (see, FIG. 63) and are separated in the deployed configuration (FIG. 62). The split junction 1914 is located closer to a distal end of the balloon 1906 for the electrode 1908 to separate as illustrated.

Figure 64:
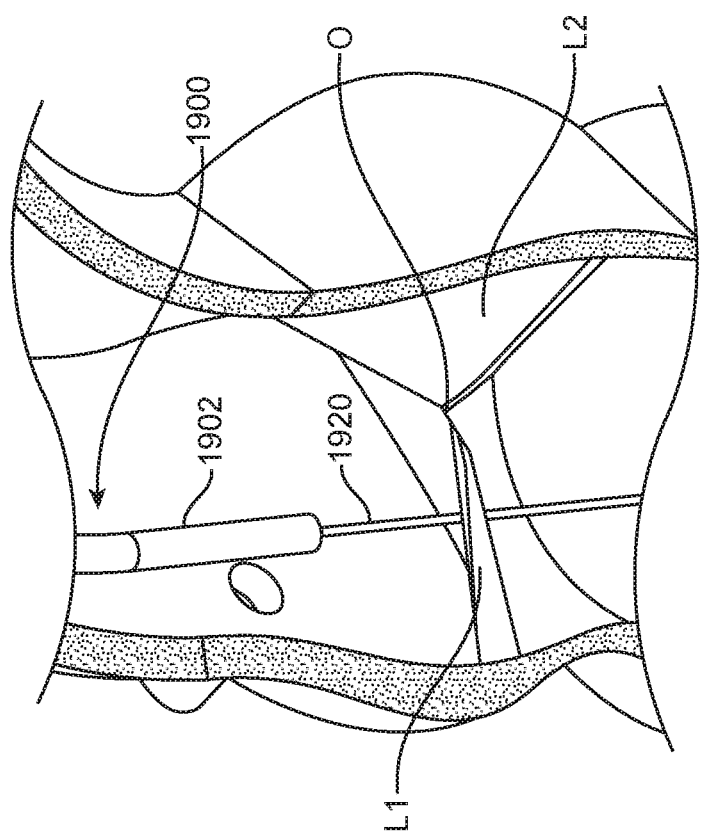
FIGS. 64-67 illustrate one example method of using the device of FIG. 62.
Figure 65:
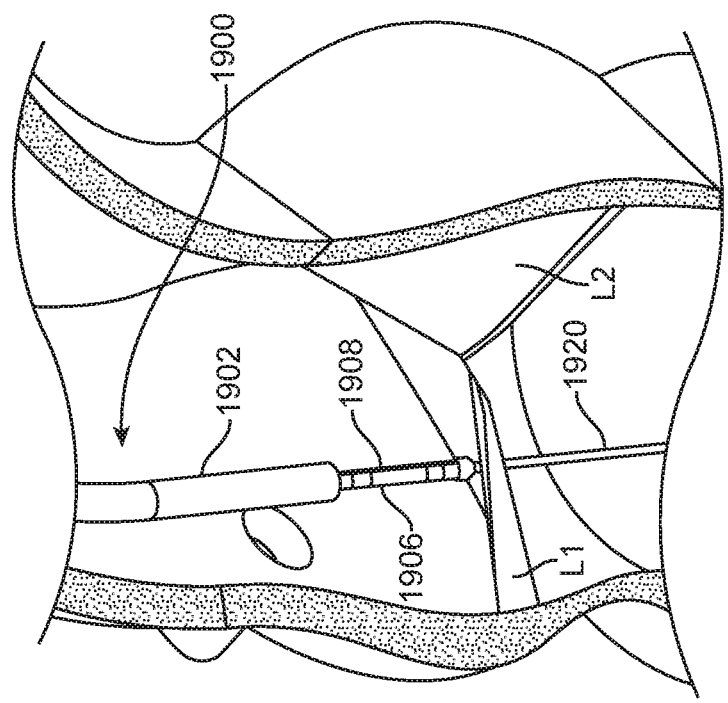
Figure 66:
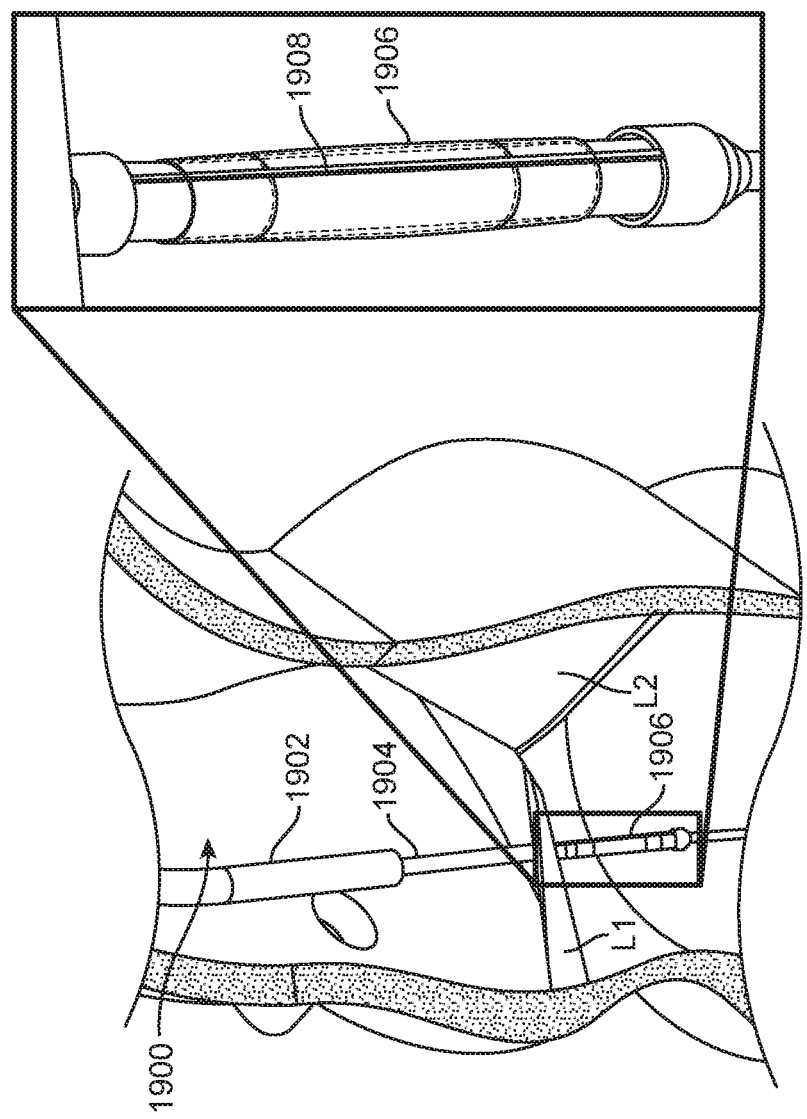
Figure 67:
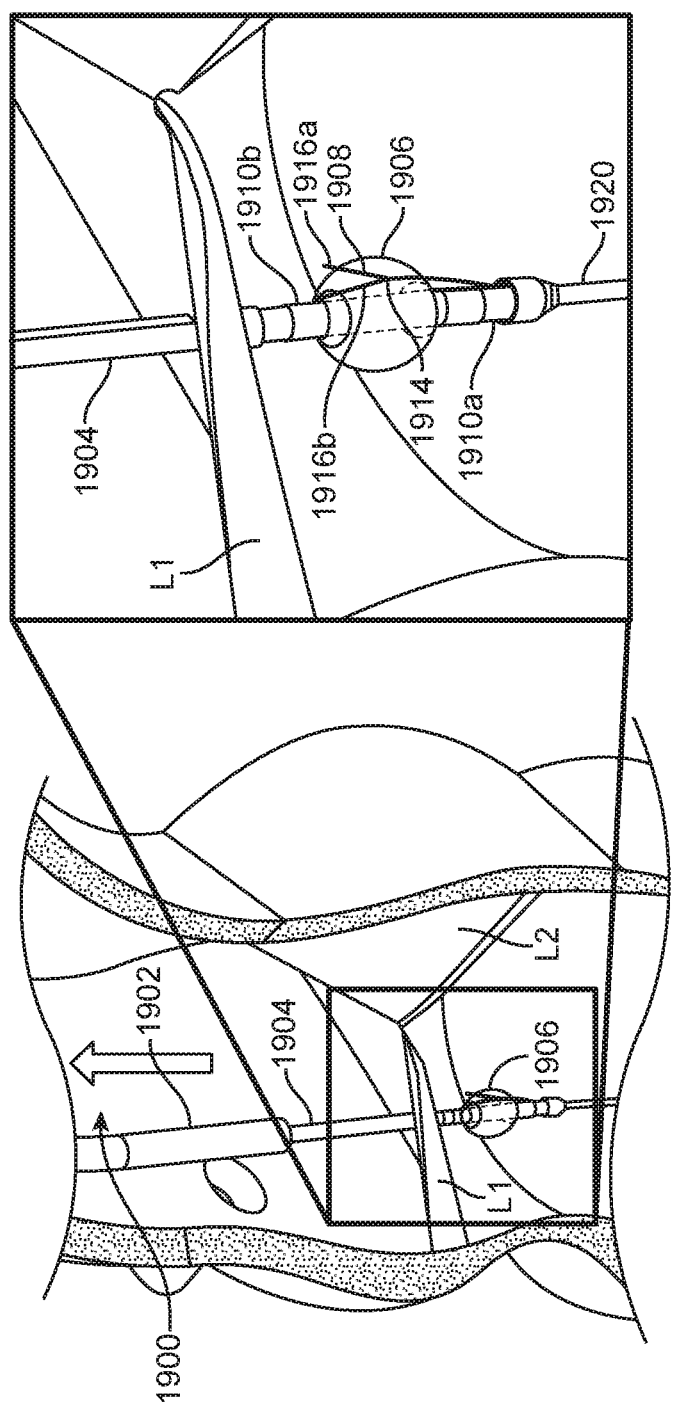

One example method of using the device 1900 is described as follows as is illustrated in FIGS. 64-67. A hole is punctured through one leaflet L1 (by whatever means is preferred, examples which are disclosed herein). A guidewire 1920 is placed through the hole in the leaflet L1 (FIG. 64). The outer catheter 1902 is tracked around the aortic arch to a location in the ascending aorta. In a deflated state, the balloon 1906 is advanced out of the outer catheter 1902 via the inner catheter 1904 as is shown in FIG. 65. Then, the balloon 1906 is advanced through the hole as shown in FIG. 66. When the balloon is below the leaflet L1, the balloon 1906, the inner catheter 1904 can optionally be rotated so the severing element 1908 is oriented in the direction of the desired leaflet cut (this can be done either before or after the severing element 1908 is moved to the deployed position). The balloon 1906 is inflated (FIG. 67), which forces the severing element 1908 to transition to the deployed arrangement so that the first portion 1916a extends away from the balloon 1906. The severing element 1908 can be activated and the balloon 1906 can be pulled proximally in order to create the cut in the leaflet L1. The process can be repeated until all desired cuts are formed in all desired leaflets.

One aspect of the disclosure includes a valve preparation device including an outer catheter, an inner catheter coaxially slidable within the outer catheter, a balloon secured to the inner catheter and an electrode extending along a length of the balloon. In one embodiment, the device further includes a plurality of electrodes extending along a length of the balloon. In one embodiment, the electrode is segmented. In one implementation, the device further includes a first attachment ring interconnecting the electrode to the inner catheter and a second attachment ring interconnecting the electrode to the inner catheter. In one embodiment, the first and second attachment rings are slidable along the inner catheter. Optionally, the valve preparation device further includes a positioning device configured to align a puncturing element in front of a coronary ostium. In some embodiments, the positioning device includes a positioning catheter and a positioning balloon; wherein the valve preparation device can be delivered through the positioning catheter. The electrode includes a first portion and a second portion that interconnect at a split junction; wherein, when the balloon is inflated, the first portion is configured to extend away from the second portion at the split junction. In one embodiment, the electrode includes an insulator spanning a portion of a circumference of the electrode.

Aspects of the disclosure further include a method of preparing a heart valve having a plurality of leaflets and a valve opening. The method includes providing a valve preparation device including an outer catheter, an inner catheter coaxially slidable within the outer catheter, a balloon secured to the inner catheter, and an electrode extending along a length of the balloon. The method includes delivering the valve preparation device to a first leaflet of the plurality of leaflets and aligning the electrode with an area of the first leaflet to be severed. The balloon is at least partially inflated and the electrode is actuated to create a first slit in the first leaflet. The method can further include providing a positioning device and using the positioning device to guide the valve preparation device to the first leaflet. In some embodiments, the positioning device includes a positioning catheter and a positioning balloon. In some variations the method includes guiding the positioning catheter to the first leaflet, inflating the positioning balloon and guiding the valve preparation device through the positioning catheter to the first leaflet. In some embodiments, the positioning device includes first and second guide wires; wherein the first guide wire is inserted within one of a right or left coronary and the second guide wire is inserted within a left ventricle of the heart. In some embodiments, the balloon is delivered through a puncture in the first leaflet prior to being inflated. In some embodiments, the electrode includes a first portion and a second portion that interconnect at a split junction; wherein, as the balloon is at least partially inflated, the first portion is extends away from the second portion at the split junction. In some methods, as the balloon is at least partially inflated, the electrode slides with respect to the inner catheter. In some embodiments, a second slit is created in the first leaflet to define a flap in the first leaflet. In some embodiments, the balloon is inserted within the valve opening. In some implementations, the device includes a plurality of electrodes spaced around a circumference of the balloon and the method includes creating a plurality of slits in the plurality of leaflets with the plurality of electrodes. The method can optionally include stabilizing the plurality of leaflets with a frame positioned in the valve opening during the step of actuating the electrode.

Another aspect of the disclosure includes a valve preparation device including an inner catheter coaxially aligned and positioned at least partially within the outer catheter and a first jaw pivotally connected to a second jaw. The first and second jaws extend from the inner catheter. Each jaw defines an edge. The first and second jaws have a closed arrangement in which the edges are in contact and an open arrangement in which the first and second jaws are splayed open with respect to each other. The device further includes a first severing element connected to the second jaw. In one implementation, the first jaw includes a second severing element. In one embodiment, the first and second severing elements is selected from the group consisting of an electrode, plasma electrode, high frequency ultrasound, resistive heating element, cryoablation element, microwave energy element or a mechanical cutter. In one embodiment, the first severing element is positioned within a receiving area between the first and second jaws. Optionally, the device further includes a positioning device on which the outer catheter slides. In some embodiments, the first jaw is configured to receive a first guide wire and the second jaw is configured to receive a second guide wire. In various embodiments, the first severing element is a rotary cutter. In one implementation, the outer catheter can be positioned over the first and second jaws to collapse the first and second jaws into a cylindrical configuration. In one embodiment, the first severing element includes an electrode that is biased into a position away from the second jaw. In some embodiments, the electrode defines a cutting edge. In some embodiments, the first severing element includes a blade. In various embodiments, an inner arm is positioned between the first and second jaws. In one embodiment, the inner arm includes a slot through which the first severing element extends.

Aspects of the disclosure further include a method of preparing a heart valve of a patient, the heart valve having a plurality of leaflets and a valve opening. The method includes providing a valve preparation device including an outer catheter, an inner catheter coaxially aligned and positioned at least partially within the outer catheter and a first jaw pivotally connected to a second jaw. The first and second jaws extending from the inner and each jaw defining an edge. The first and second jaws have a closed arrangement in which the edges are in contact and an open arrangement in which the first and second jaws are splayed open with respect to each other. The device further includes a severing element connected to the second jaw. The method further includes delivering the valve preparation device to the heart valve and then proximally retracting the outer catheter and transitioning the first and second jaws to the open arrangement. The method includes inserting one of the first and second jaws into the valve opening to position a first leaflet of the plurality of leaflets between the first and second jaws and severing at least a portion of the first leaflet with the severing element. In one embodiment, the method includes closing the first and second jaws and removing the severed leaflet from the patient. In one embodiment, the step of transitioning the first and second jaws to the open arrangement includes pushing a wire interconnected to the first jaw in a distal direction. In one embodiment, the method includes rotating the severing element from a folded position to an unfolded position prior to the step of severing. In one embodiment, the step of rotating includes pushing a wire interconnected to the severing element in a distal direction. In one embodiment, the valve preparation device includes a middle arm positioned between the first jaw and the second jaw; wherein the method includes positioning the first leaflet between the middle arm and the first jaw. In one embodiment, the severing element includes an electrode.

One aspect of the disclosure includes a delivery device for delivering a stented prosthesis to a target site. The delivery device has at least one elongate tension member that can compressively retain the stented prosthesis to the delivery device and a shaft assembly having a lumen and a cutting assembly positioned within the lumen. In one implementation, the cutting assembly includes a blade that is configured to selectively sever the at least one elongate tension member. In one example, the blade is flexible. In one example, the cutting assembly includes a blade holder defining a jog through which the blade can travel. In one implementation the delivery device further includes a handle assembly and the cutting assembly actuates movement of the cutting assembly. In some embodiments, each of the elongate tension members includes first and second ends; wherein the first and second ends are connected to the cutting assembly. In some embodiments, each of the elongate tension members are interconnected with a loop that can be severed by the cutting assembly. In one implementation, the blade is a circular blade circumscribing an aperture in the cutting assembly. In some embodiments, the elongate tension members are positioned within an aperture prior to being severed. In one embodiment, the cutting assembly can move within the lumen. In one example, the cutting assembly includes a pin through which the elongate tension members are threaded and also a cutting blade that is fixed to the lumen; wherein the pin can move with respect to the cutting blade. In another example, the cutting assembly includes a cutting blade and a cord looped around the elongate tension members that is configured to draw the elongate tension members toward the cutting blade. In one embodiment, the cutting blade can be actuated to extend out of the lumen to sever the elongate tension members.

In one example, the cutting assembly includes a pair of resilient blades extending out of a hollow shaft; wherein the blades are configured to be actuated by compressing the blades against the hollow shaft. Optionally, the shaft is hollow and the elongate tension members are threaded through the hollow shaft. In one implementation, the delivery device has a loaded state in which a stented prosthetic heart valve is loaded thereto; wherein the blade is positioned distal to the elongate tension members in the loaded state. In one example, the cutting assembly includes a pull pin positioned within the lumen; wherein the blade is secured to the pull pin. In one example, the cutting assembly includes a sleeve having a plurality of windows; wherein the blade is positioned at an edge of at least one of the plurality of windows; wherein the sleeve can move along the shaft assembly. In one implementation, the cutting assembly includes a plurality of blades such that each window edge includes blade. In one example, the blade can travel along a path defined by an inner diameter of the lumen. In one embodiment, movement of the blade is restricted by a separator. In one example, the blade rotates within the shaft assembly. In one example, the blade rotates around a central axis of the shaft assembly. In one embodiment, the cutting assembly includes a torque shaft, a stationary disk and an interface disk; wherein the blade is positioned on an edge of an aperture in one of the stationary disk or the interface disk. In one embodiment, the cutting assembly includes a pull pin including a plurality of protrusions on which one blade is positioned; the protrusions being arranged and configured to engage and sever the elongate tension members at the blades. In one example, the cutting assembly includes a pull pin and the blade extends from a distal end of the pull pin; wherein actuation of the blade is accomplished with movement of the pull pin. In one implementation, the shaft assembly includes first, second and third lumens; wherein the at least one tension member is routed through the first and second lumens and the cutting assembly is at least partially positioned within the third lumen; wherein a gap interconnects the second and third lumens and a blade of the cutting assembly can travel through the gap to the second lumen.

Another aspect of the disclosure includes a valve preparation device including a catheter having distal and proximal ends. The catheter further includes an inflation lumen and a balloon positioned at the distal end of the catheter and in fluid communication with the inflation lumen. The balloon including an electrode. In one embodiment, the balloon includes a plurality of electrodes. In one implementation, the plurality of electrodes are circumferentially spaced around the balloon. In one implementation, each electrode is longitudinally subdivided into separately powered elements. In one embodiment, the catheter includes a guide wire lumen and a blood flow lumen. In one embodiment, the balloon has a helical spiral shape when in an inflated arrangement. In one embodiment, an insulator is provided between the balloon each the electrode. In one implementation, the electrode is biased outwardly from an outer surface of the balloon.

Aspects of the disclosure include a method of treating calcified aortic leaflets including providing a valve preparation device including a catheter having distal and proximal ends. The catheter further including an inflation lumen and a balloon positioned at the distal end of the catheter and in fluid communication with the inflation lumen. The balloon including an electrode. The method further including delivering the balloon in a deflated arrangement to an aortic valve, at least partially inflating the balloon, and energizing the electrode to create a slit in at least one leaflet of the aortic valve. In one embodiment, the method comprises the step of rotationally aligning the balloon prior to the step of energizing the electrode. In one embodiment, the step of energizing the electrode is conducted when the balloon is in a partially inflated arrangement and the method further comprises further inflating the balloon during the step of energizing the electrode. In one embodiment, the balloon includes a plurality of electrodes and the step of energizing the electrode includes selectively energizing one of a plurality of electrodes. In one embodiment, the catheter includes a lumen that allows for perfusion during the steps of inflating the balloon and energizing the electrode. In one embodiment, the electrode is biased outwardly with respect to an outer surface of the balloon. In one embodiment, the electrode includes an insulator positioned between the balloon and the electrode.

Aspects of the disclosure include a disabling device including a catheter including a first lumen, second lumen, third lumen and fourth lumen. The device further includes a first positioning arm extending within the first lumen and distally out of the catheter, a second positioning arm extending within the second lumen and distally out of the catheter, and a wire extending through both of the second and third lumens, wherein the lumen maintains an electrode positioned distal to the catheter. In one embodiment, the first lumen and the second lumen are on opposing sides of the catheter. In one implementation, the device includes a fifth lumen in the catheter and tongs extending from the fifth lumen. In one implementation, the grasper includes two arms that are each associated with a guide wire; wherein the catheter slides on the two arms. Optionally, the fifth lumen is sized to receive a ligating device. In one embodiment, the device includes a sheath coaxially aligned with and slidably positioned over the catheter. Optionally, the electrode has a semi-lunar shape. In one embodiment, the electrode spans approximately 360 degrees.

Embodiments of the disclosure further include a method of treating a patient having a ligating device interconnecting an anterior mitral leaflet and a posterior mitral leaflet of a mitral valve and thereby obstructing an opening of the mitral valve. The method includes providing a disabling device including a first catheter from which a severing element extends and directing the severing element proximate the ligating device. The method further includes severing the mitral valve proximate the clip until the ligating device no longer obstructs the opening. In one example, the anterior mitral leaflet is severed. In one embodiment, after the step of severing, the ligating device remains within the patient. Some embodiments include removing a plurality of ligating device from the mitral valve. Some embodiments include the step of implanting a prosthetic heart valve within the opening. In one example, the disabling device further includes a guide provided within a lumen of the first catheter, the guide including first and second arms. In one embodiment, the first catheter includes a first lumen, second lumen, third lumen and fourth lumen as well as a first positioning arm extending within the first lumen and distally out of the first catheter; a second positioning arm extending within the second lumen and distally out of the first catheter; and a wire extending through both of the second and third lumens, wherein the lumen maintains an electrode positioned distal to the first catheter. In one example, the step of directing the severing element includes advancing the first catheter to a left atrium, rotating the catheter to align the first and second positioning arms with the anterior mitral leaflet and the posterior leaflet and advancing the first catheter distally so that the first and second positioning arms penetrate the anterior mitral leaflet and the posterior leaflet on either side of the ligating device. In one embodiment, the device includes tongs and the method further comprising grasping the ligating device with the tongs. In one example, the method includes removing the ligating device from the patient with the tongs. In one embodiment, the device further includes a sheath coaxially aligned with and slidably positioned over the first catheter, wherein the sheath is slid distally over the ligating device after the ligating device is captured by the tongs. Optionally, the tongs are provided in a fifth lumen. In one embodiment, the fifth lumen is sized to receive the ligating device. In one embodiment, the device further includes a second catheter positioned within the first catheter, wherein the second catheter includes first and second jaws. In one embodiment, the method includes capturing the ligating device in the first and second jaws. In one example, the ligating device is severed with the disabling device. In one embodiment, the ligating device is a suture. In another embodiment, the ligating device is a clip. In one example, the severing element has a semi-lunar shape. In one embodiment, the severing element spans approximately 360 degrees.

In view of the present disclosure, it will be generally understood that any "cutting" or "severing" to create a cut or slit will typically be through an entire thickness of one or more leaflets AL, PL so that the ligation device C is sufficiently disabled and/or capable of removal by the disabling device. If a ligation device, however, does not extend through an entire thickness of one or more leaflets AL, PL, the "severing" or "cutting" may not necessarily have to extend through an entire thickness of the leaflet(s) to effectively disable and/or remove the ligation device.

If not specifically mentioned above, any of the aforementioned devices can optionally include radiopaque markers (e.g., markers 815 of FIG. 24A) to assist in confirming positioning of the device via fluoroscopy techniques. In one example, inner and/or outer catheters include one or more radiopaque markers. The markers 815 can, in some embodiments, be positioned adjacent beginning and ends of respective severing elements.

Any of the aforementioned devices can also be configured such that the inner catheter and/or outer catheters are torqueable to assist with alignment of the respective device. Torqueing can be accomplished by, for example, rotating a handle assembly at the proximal end of the respective catheter or by selectively actuating one or more catheter shafts via a rotating mechanism in the handle assembly (e.g., if it is only desired to rotate the inner catheter and not the outer catheter).

Any of the aforementioned devices can also be configured with a steering mechanism, such as a pull wire to assist in the positioning of the distal end of the inner and/or outer catheter.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A valve preparation device comprising:
   an outer catheter;
   an inner catheter coaxially slidable within the outer catheter;
   a balloon secured to the inner catheter;

an electrode extending along a length of the balloon, the electrode including a first portion and a second portion, the second portion having first and second ends, each end positioned on the inner catheter, wherein the first portion interconnects with the second portion at a split junction located between the first and second ends; wherein, when the balloon is inflated, the first portion is configured to transition away from both of the balloon and the second portion at the split junction; and a first attachment ring interconnecting the electrode to the inner catheter; wherein the first attachment ring can slide along a length of the inner catheter.

2. The valve preparation device of claim 1, further comprising a plurality of electrodes extending along the length of the balloon.

3. The valve preparation device of claim 1, wherein the electrode is segmented.

4. The valve preparation device of claim 1, further comprising a second attachment ring interconnecting the electrode to the inner catheter.

5. The valve preparation device of claim 1, wherein the valve preparation device further includes a positioning device configured to align a puncturing element in front of a coronary ostium.

6. The valve preparation device of claim 5, wherein the positioning device includes a positioning catheter and a positioning balloon; wherein the valve preparation device can be delivered through the positioning catheter.

7. The valve preparation device of claim 1, wherein the electrode includes an insulator spanning a portion of a circumference of the electrode.

8. A method of preparing a heart valve having a plurality of leaflets and a valve opening, the method comprising:
providing a valve preparation device including:
an outer catheter,
an inner catheter coaxially slidable within the outer catheter,
a balloon secured to the inner catheter, and
an electrode extending along a length of the balloon, the electrode including a first portion and a second portion, the second portion having first and second ends, each end positioned on the inner catheter, wherein the first portion interconnects with the second portion at a split junction located between the first and second ends; further wherein the first and second portions are aligned with the inner catheter when the balloon is in a deflated configuration;
delivering the valve preparation device to a first leaflet of the plurality of leaflets with the balloon in the deflated configuration such that opposing surfaces of the first and second portions touch each other;
aligning the electrode with an area of the first leaflet to be severed;
at least partially inflating the balloon so that the first portion extends away from both of the balloon and the second portion at the split junction so that the opposing surfaces no longer touch; and actuating the electrode to create a first slit in the first leaflet.

9. The method of claim 8, further comprising providing a positioning device and using the positioning device to guide the valve preparation device to the first leaflet.

10. The method of claim 9, wherein the positioning device includes a positioning catheter and a positioning balloon; wherein the method includes guiding the positioning catheter to the first leaflet, inflating the positioning balloon and guiding the valve preparation device through the positioning catheter to the first leaflet.

11. The method of claim 9, wherein the positioning device includes first and second guide wires; wherein the first guide wire is inserted within one of a right or left coronary and the second guide wire is inserted within a left ventricle of the heart.

12. The method of claim 8, wherein the balloon is delivered through a puncture in the first leaflet prior to being inflated.

13. The method of claim 8, wherein, as the balloon is at least partially inflated, the electrode slides with respect to the inner catheter.

14. The method of claim 8, wherein the electrode includes an insulator spanning a portion of a circumference of the electrode.

15. The method of claim 8, wherein the balloon is inserted within the valve opening.

16. The method of claim 15, wherein the device includes a plurality of electrodes spaced around a circumference of the balloon and the method includes creating a plurality of slits in the plurality of leaflets with the plurality of electrodes.

17. The method of claim 8, further comprising stabilizing the plurality of leaflets with a frame positioned in the valve opening during the step of actuating the electrode.

18. A valve preparation device comprising:
an outer catheter;
an inner catheter coaxially slidable within the outer catheter;
an electrode balloon secured to the inner catheter; and
an electrode extending along a length of the electrode balloon; wherein the valve preparation device further includes a positioning device configured to align a puncturing element in front of a coronary ostium; further wherein the positioning device includes a positioning catheter and a positioning balloon having a first inflatable segment and a second inflatable segment positioned proximal to a distal end of the positioning catheter and on opposing sides of the positioning catheter; wherein the valve preparation device can be delivered through the positioning catheter.

19. The valve preparation device of claim 18, wherein the first inflatable segment and the second inflatable segment are separated by a strip of adhesive.

* * * * *